(12) United States Patent
Hayes et al.

(10) Patent No.: US 11,457,978 B2
(45) Date of Patent: Oct. 4, 2022

(54) RADIOFREQUENCY PROBE AND METHODS OF USE AND MANUFACTURE OF SAME

(71) Applicant: Stryker Corporation, Kalamazoo, MI (US)

(72) Inventors: James Hayes, San Jose, CA (US); Brian Fouts, Morgan Hill, CA (US); Conrad Smith, Hollister, CA (US)

(73) Assignee: Stryker Corporation, Kalamazoo, MI (US)

( * ) Notice: Subject to any disclaimer, the term of this patent is extended or adjusted under 35 U.S.C. 154(b) by 620 days.

(21) Appl. No.: 16/444,986

(22) Filed: Jun. 18, 2019

(65) Prior Publication Data
US 2019/0380774 A1    Dec. 19, 2019

Related U.S. Application Data

(60) Provisional application No. 62/744,326, filed on Oct. 11, 2018, provisional application No. 62/686,404, filed on Jun. 18, 2018.

(51) Int. Cl.
*A61B 18/14* (2006.01)
*A61B 18/00* (2006.01)

(52) U.S. Cl.
CPC .............. *A61B 18/1492* (2013.01); *A61B 2018/00107* (2013.01); *A61B 2018/00577* (2013.01); *A61B 2018/00702* (2013.01); *A61B 2018/00791* (2013.01); *A61B 2018/1405* (2013.01)

(58) Field of Classification Search
CPC .... A61B 2018/1405; A61B 2018/1472; A61B 18/148; A61B 2218/007; A61B 2018/1253; A61N 1/044; A61N 1/0424
See application file for complete search history.

(56) References Cited

U.S. PATENT DOCUMENTS

| | | | |
|---|---|---|---|
| 4,785,807 | A | 11/1988 | Blanch |
| 5,944,715 | A | 8/1999 | Goble et al. |
| 6,030,381 | A | 2/2000 | Jones et al. |
| 6,210,405 | B1 | 4/2001 | Goble et al. |
| 6,238,393 | B1 | 5/2001 | Mulier et al. |
| 6,293,946 | B1 | 9/2001 | Thorne |
| 6,336,926 | B1 | 1/2002 | Goble |
| 6,482,202 | B1 | 11/2002 | Goble et al. |

(Continued)

*Primary Examiner* — Thomas A Giuliani
*Assistant Examiner* — Christine A Dedoulis
(74) *Attorney, Agent, or Firm* — Lerner, David, Littenberg, Krumholz & Mentlik, LLP

(57) ABSTRACT

In one embodiment, the present disclosure relates to an electrosurgical device that includes an outer body, an inner body disposed partially within the outer body, three plates and an insulator. A first plate of the three plates includes a plurality of apertures and is positioned so that each of two projections extending from the inner body extend through a respective aperture of the plurality of apertures of the first plate. A second plate and a third plate of the three plates are both disposed on the first plate such that each of the two projections extends through an aperture of the second plate or the third plate, the second and third plates being fixed to a respective projection. The insulator is disposed around the inner body and is attached to the outer body at a first end and abuts the first plate at a second end opposite the first end.

12 Claims, 40 Drawing Sheets

(56) References Cited

U.S. PATENT DOCUMENTS

| | | | |
|---|---|---|---|
| 6,491,690 B1 | 12/2002 | Goble et al. |
| 6,565,560 B1 | 5/2003 | Goble et al. |
| 6,565,561 B1 | 5/2003 | Goble et al. |
| 6,692,492 B2 | 2/2004 | Simpson et al. |
| 6,706,039 B2 | 3/2004 | Mulier et al. |
| 6,757,565 B2 | 6/2004 | Sharkey |
| 6,814,731 B2 | 11/2004 | Swanson |
| 6,851,453 B2 | 2/2005 | Lipscomb et al. |
| 6,852,091 B2 | 2/2005 | Edwards et al. |
| 6,869,430 B2 | 3/2005 | Balbierz et al. |
| 6,923,803 B2 | 8/2005 | Goble |
| 6,962,589 B2 | 11/2005 | Mulier et al. |
| 7,001,380 B2 | 2/2006 | Goble |
| 7,150,746 B2 | 12/2006 | DeCesare et al. |
| 7,156,845 B2 | 1/2007 | Mulier et al. |
| 7,241,293 B2 | 7/2007 | Davison |
| 7,244,256 B2 | 7/2007 | DeCesare et al. |
| 7,261,711 B2 | 8/2007 | Mulier et al. |
| 7,278,994 B2 | 10/2007 | Goble |
| 7,481,807 B2 | 1/2009 | Knudsen et al. |
| 7,837,683 B2 | 11/2010 | Carmel et al. |
| 7,892,230 B2 | 2/2011 | Woloszko |
| 8,066,704 B2 | 11/2011 | DeCesare et al. |
| 8,187,270 B2 | 5/2012 | Auth et al. |
| 8,382,753 B2 | 2/2013 | Truckai |
| 8,425,506 B2 | 4/2013 | Gallo, Sr. et al. |
| 8,840,610 B2 | 9/2014 | Humble |
| 8,979,838 B2 | 3/2015 | Woloszko et al. |
| 8,998,895 B2 | 4/2015 | Besch et al. |
| 9,011,428 B2 | 4/2015 | Nguyen et al. |
| 9,113,896 B2 | 8/2015 | Mulier et al. |
| 9,168,082 B2 | 10/2015 | Evans et al. |
| 9,204,918 B2 | 12/2015 | Germain et al. |
| 9,254,166 B2 | 2/2016 | Mum et al. |
| 9,271,784 B2 | 3/2016 | Evans et al. |
| 9,283,032 B2 | 3/2016 | Thomas et al. |
| 9,326,809 B2 | 5/2016 | Williams et al. |
| 9,456,865 B2 | 10/2016 | Woloszko et al. |
| 9,474,571 B2 | 10/2016 | Rioux et al. |
| 9,526,556 B2 | 12/2016 | Goode et al. |
| 9,526,559 B2 | 12/2016 | Benamou et al. |
| 9,549,754 B2 | 1/2017 | Shadduck et al. |
| 9,597,149 B2 | 3/2017 | Germain et al. |
| 9,649,148 B2 | 5/2017 | Woloszko et al. |
| 9,693,818 B2 | 7/2017 | Woloszko et al. |
| 9,700,371 B2 | 7/2017 | Brewer et al. |
| 9,737,362 B2 | 8/2017 | Germain et al. |
| 9,757,188 B2 | 9/2017 | Garabedian et al. |
| 9,820,809 B2 | 11/2017 | Hoodless et al. |
| 9,839,468 B2 | 12/2017 | Nguyen et al. |
| 2007/0260234 A1 | 11/2007 | McCullagh et al. |
| 2008/0221567 A1 | 9/2008 | Sixto et al. |
| 2010/0042095 A1 | 2/2010 | Bigley et al. |
| 2010/0204690 A1* | 8/2010 | Bigley ............... A61B 18/148 606/41 |
| 2014/0257277 A1* | 9/2014 | Woloszko ............ A61B 18/14 606/41 |
| 2017/0071616 A1* | 3/2017 | Sims ................. A61B 18/1442 |

\* cited by examiner

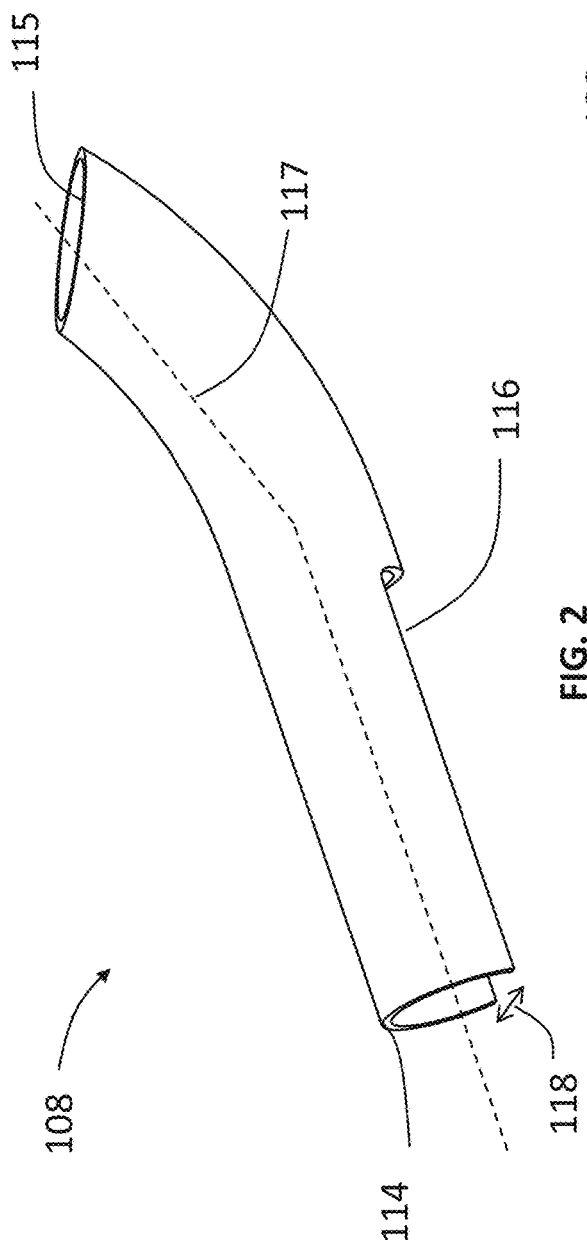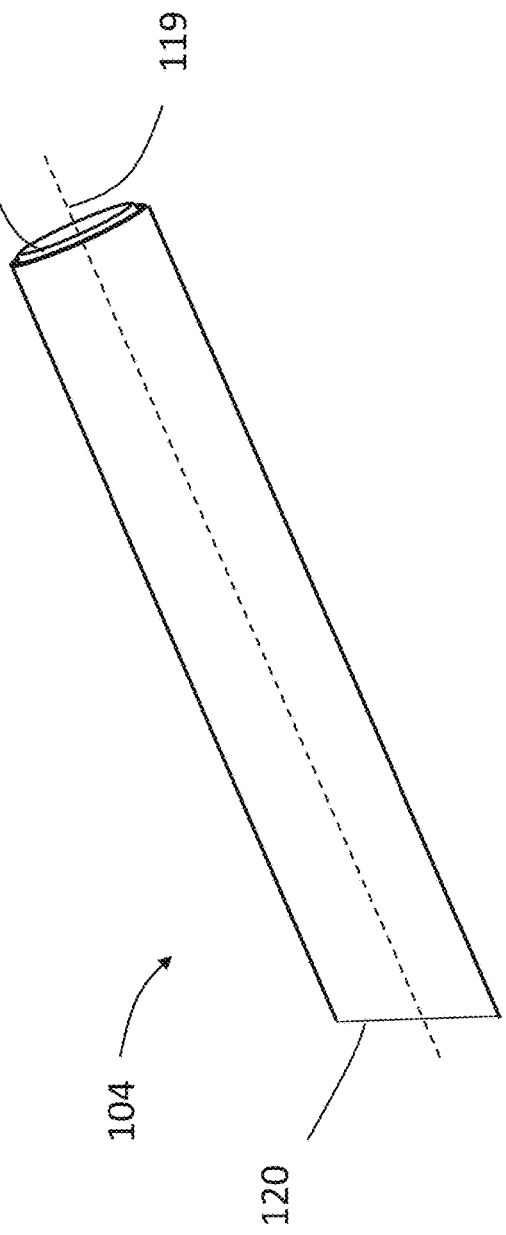
FIG. 2
FIG. 3

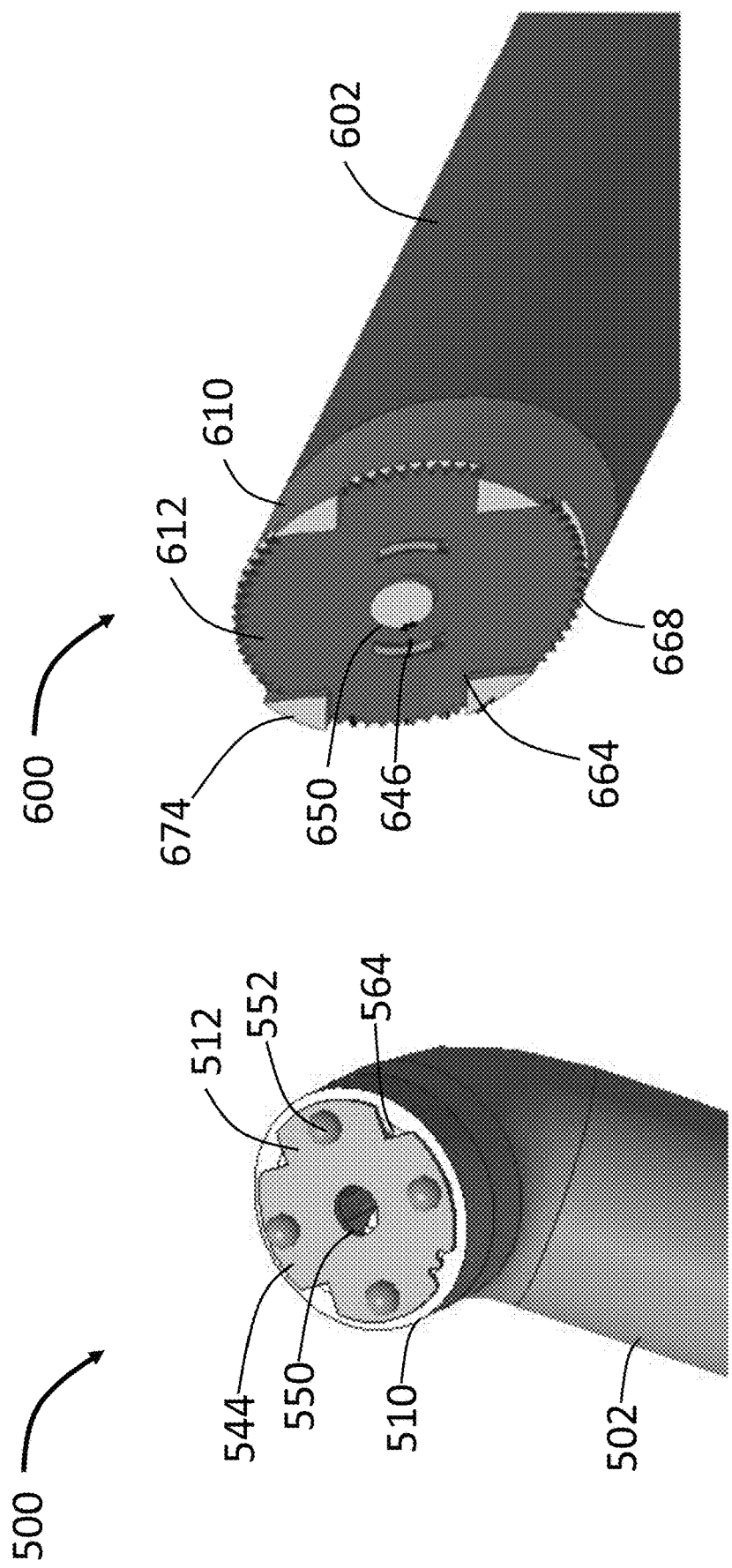

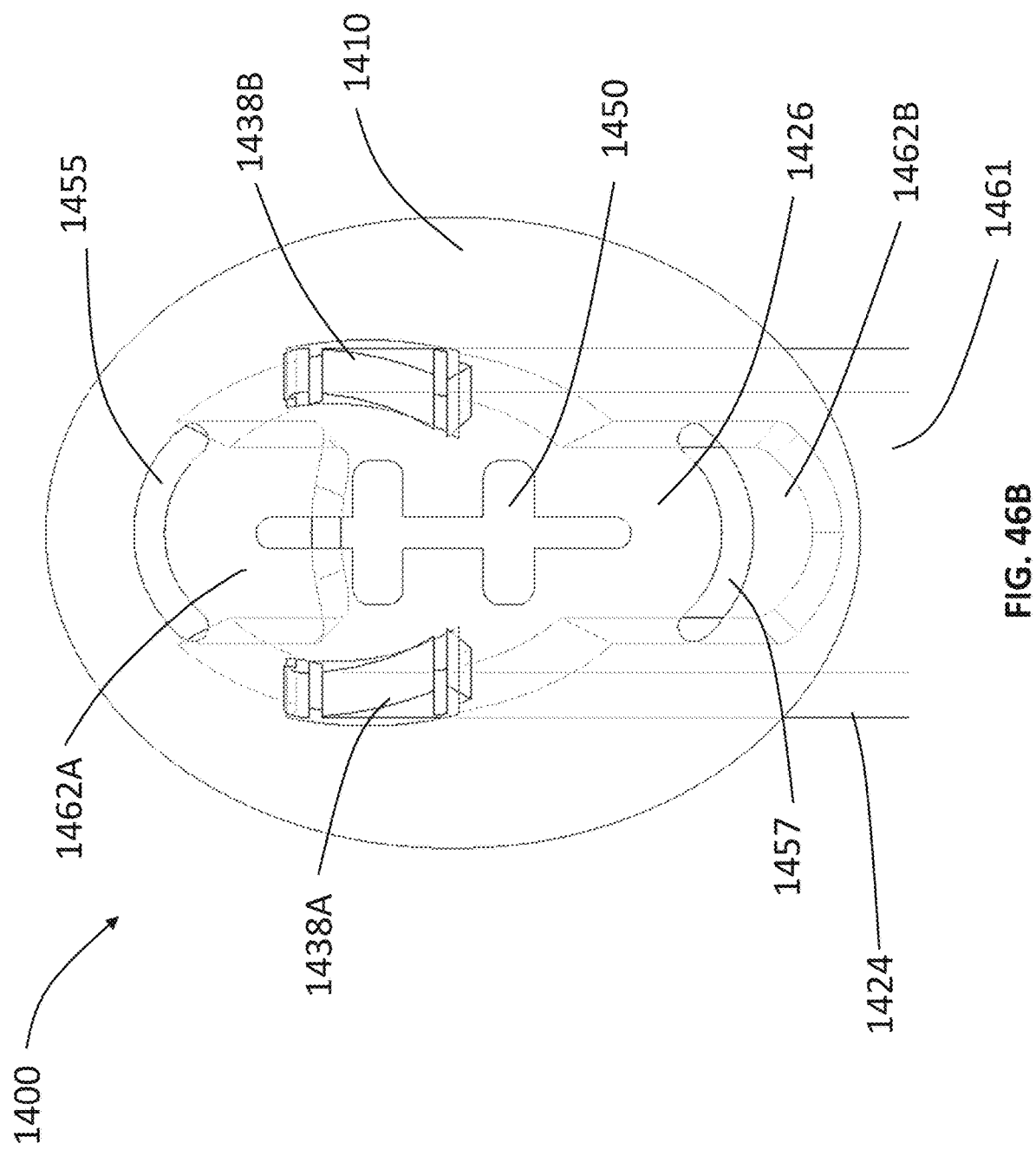

RADIOFREQUENCY PROBE AND METHODS OF USE AND MANUFACTURE OF SAME

CROSS-REFERENCE TO RELATED APPLICATIONS

The present application claims the benefit of the filing date of commonly owned U.S. Provisional Application Nos. 62/744,326 and 62/686,404, filed on Oct. 11, 2018 and Jun. 18, 2018, respectively, the disclosures of which are hereby incorporated by reference herein in their entirety.

FIELD OF INVENTION

The present disclosure relates generally to radiofrequency probes and methods of manufacture of same.

BACKGROUND OF THE INVENTION

Radiofrequency ("RF") ablation probes are generally used in ablation and removal of soft tissue. Surgical procedures utilizing RF ablation probes rely on rapid heat and plasma generation at a focused area to precisely excise tissue. In the context of orthopedic surgery, RF probes are typically used to quickly and effectively remove damaged soft tissue to prepare an anatomical site for a repair of the remaining soft tissue and/or bone.

Continuing with their use in orthopedic applications, RF probes typically have a generally linear shape extending to a distal tip which includes an electrode(s) for performing the tissue removal. Commonly, in order to reach certain tissues within the tight confines of, for example, a bone joint, the distal end of the probe must have a particular shape. One particularly beneficial shape for these applications is where the distal end has a tight bend such that the electrode is at a distinct angle relative to the rest of the shaft of the probe. The tight bend at the distal end, however, creates certain issues such as, for example, difficulties in manufacturing a device that is sufficiently malleable to be shaped into a tight bend, while still having sufficient strength to maintain the inner structure of the shaft. Further, due to the properties of these materials and the forces exerted on the probe during ablation, the distal end may be vulnerable to breakage or deformation if the material used is too malleable or brittle, particularly following the bending process in manufacture.

Thus, the probe should be relatively easy and cost-effective to manufacture, be able to include a tight distal bend and a small shaft diameter without limiting the shaft's flow path cross section, and the distal end should maintain sufficient shaft strength during use of the probe. To achieve sufficient shaft strength, the outer diameter of the shaft may either be increased beyond what is ideally desired—resulting in a larger incision site—or, alternatively, a material of greater stiffness may be utilized. A stiffer material, however, limits the arc of the distal bend. Furthermore, bending a stiffer material to the desired arc increases the degree of cross sectional deformation due to buckling. Such ovalization and kinking of the shaft's cross section restricts the flow path. Alternatively a softer, heat treatable material could be used, of which the desired distal bend could be formed before the material is hardened so as to achieve the desired mechanical properties. However, such heat treatment process may reduce tooling and machining precision leading to manufacturing inconsistencies.

Further, RF probes can include an aspiration port to remove ablated tissue and debris from the tissue site. An active flow of a working fluid, such as saline or the like as commonly used in arthroscopic surgery, can reduce the electrode surface temperature during the RF probe operation and thereby minimizing the chance of the RF probe damaging surrounding tissues. Aspiration ports are formed on the electrode surface by removing electrode material, which results in less electrode material and more electrode "edges" which could be subject to additional wear. Therefore, the inlet area of the aspiration port is limited in order to preserve electrode material to extend the life of the RF probe. However, such small aspiration ports may be clogged by large particles of tissues and debris, or be blocked by the tissue being treated (e.g., while the electrode is positioned against tissue being treated) which may severely restrict or prevent aspiration through the RF probe.

Therefore, an improved manufacturing technique is desirable for an RF ablation probe which can maintain its form without limiting the flow path cross section or increasing its diameter, and which results in an improved RF probe capable of reliable use under the various forces experienced during orthopedic applications.

Additionally, an RF ablation probe with improved aspiration capability is desirable for superior ablation performance during orthopedic applications.

BRIEF SUMMARY OF THE INVENTION

Disclosed herein are electrosurgical devices, commonly referred to as RF probes, and methods for manufacturing the same.

In a first aspect of the present disclosure, an electrosurgical device for use in arthroscopic procedures is provided. The electrosurgical device may include an elongated outer body, an elongated inner body, a plate and an insulator. The elongated outer body may have a proximal portion with a proximal opening and a distal portion with a distal opening. The distal portion may be engaged with the proximal portion. The proximal portion may have a proximal stiffness and the distal portion may have a distal stiffness. The proximal stiffness may be greater than the distal stiffness. The elongated inner body may be disposed partially within the outer body and may extend from a distal inner body opening to a proximal inner body opening. The plate may have a proximal surface and a distal surface. The plate may be disposed on the inner body, at or adjacent to the distal inner body opening. The insulator may be disposed between the inner body and the plate such that the plate may be configured as a first electrode and the outer body may be configured as a second electrode of the electrosurgical device.

In accordance with the first aspect, a first outer body may include the proximal portion and a second outer body may include the distal portion. The first outer body may overlap at least a portion of the second outer body along a central axis of the outer body.

The inner body may include a flexible region disposed between the proximal inner body opening and the distal inner body opening. The flexible region may include one or more cut-outs. The one or more cut-outs may be u-shaped, circumferential slots extending transversely across the inner body.

In accordance with the first aspect, in one alternative, the plate may include at least one serrated edge.

In another alternative or in addition, the insulator may include an insulator aperture extending through the insulator. The plate may include at least one plate aperture in fluid communication with the insulator aperture and the distal inner body opening. The plate aperture may be an inlet to transport fluids from a surgical site and into the inner body. The plate aperture may extend through the distal surface to the proximal surface. The plate aperture may extend along a side wall of the plate between the distal and proximal surfaces.

In accordance with this first aspect, the distal inner body opening may include at least one projection extending away from the distal inner body opening. The plate may include at least one recess extending between the proximal surface and the distal surface such that the at least one projection may be received in the at least one recess when the plate is disposed on the inner body.

In a second aspect of the present disclosure, an electrosurgical device for use in arthroscopic procedures is provided. The electrosurgical device according to this second aspect may include an elongated outer body, an elongated inner body, a plate and an insulator. The elongated outer body may have a proximal portion with a proximal opening and a distal portion with a distal opening. The proximal portion and the distal portion may be separate but connectable pieces. The distal portion may be engaged with the proximal portion. The distal portion may have a slot extending from a proximal end of the distal portion along the distal portion. The slot may define a first dimension transverse to the distal portion. The elongated inner body may be disposed within the outer body and may extend from a distal inner body opening to a proximal inner body opening. The inner body may define a second dimension transverse to the inner body. The second dimension may be less than the first dimension such that the inner body may traverse transversely through the u-shaped slot. The plate may have a proximal surface and a distal surface. The plate may be disposed on the inner body. The insulator may be disposed between the inner body and the plate such that the plate may be configured as a first electrode and the outer body may be configured as a second electrode of the electrosurgical device.

In accordance with this second aspect, a first outer body may include the proximal portion and a second outer body may include the distal portion. The first outer body may overlap at least a portion of the second outer body along a central axis of the outer body, and in one example, the u-shaped slot may be overlapped by the first outer body. The inner body may include a flexible region disposed between the proximal inner body opening and the distal inner body opening. The flexible region may include one or more cut-outs. The one or more cut-outs may be u-shaped, circumferential slots extending transversely across the inner body. The slot may be a u-shaped slot.

In accordance with a third aspect of the present disclosure, an electrosurgical device for use in arthroscopic procedures is provided. The electrosurgical device according to this aspect may include an elongated outer body, an elongated inner body, a plate and an insulator. The elongated outer body may extend between a proximal end and a distal opening and may have a first portion, a second portion and a flexible portion. The flexible portion may be disposed between the first and second portions. The flexible portion may have a stiffness less than both a first stiffness of the first portion and a second stiffness of the second portion. The first and second stiffnesses may be the same or different. The elongated inner body may be disposed within the outer body and may extend from a distal inner body opening to a proximal inner body end. The plate may have a proximal surface and a distal surface. The plate may be disposed on the inner body. The insulator may be disposed between the inner body and the plate such that the plate may be configured as a first electrode and the outer body may be configured as a second electrode of the electrosurgical device.

In accordance with the third aspect, the distal inner body opening may include at least one projection extending away from the distal inner body opening. The plate may include at least one recess extending between the proximal surface and the distal surface such that the at least one projection may be received in the at least one recess when the plate is disposed on the inner body.

In accordance with a fourth aspect of the present disclosure, a method for manufacturing an electrosurgical device is provided. A method according to this aspect may include the steps of placing an insulator over a distal end of an elongated inner body, attaching a plate having a recess extending therethrough to the distal end of the elongated body such that a projection extending from the distal end may be received within the recess, sliding a distal portion of an elongated outer body over the inner body, engaging the distal outer end of the outer body with the insulator, and bending the inner body by engaging the distal portion of the elongated body with a proximal portion of the outer body. The insulator may separate the outer body from the plate. The proximal portion may have a proximal stiffness and the distal portion may have a distal stiffness. The proximal stiffness may be greater than the distal stiffness.

In accordance with a fifth aspect of the present disclosure, a method for manufacturing an electrosurgical device is provided. A method according to this aspect may include the steps of placing an insulator over a distal end of an elongated inner body, attaching a plate having a recess extending therethrough to the distal end of the elongated inner body such that a projection extending from the distal end may be received within the recess, and bending a flexible portion of an elongated outer body to an outer contour by sliding a distal portion of the outer body over the inner body and the insulator such that a distal outer end of the outer body may contact the insulator. The insulator may separate the outer body from the plate. The insulator may define the outer contour. The flexible portion may be disposed between a first and a second portion of the distal portion. The flexible portion may have a stiffness less than both a first stiffness of the first portion and a second stiffness of the second portion.

In accordance with a sixth aspect of the present disclosure, an electrosurgical device for use in arthroscopic procedures is provided. An electrosurgical device in accordance with this aspect may include an elongated upper outer body, an elongated inner body, a first plate, a second plate and an insulator. The elongated outer body may have a proximal portion with a proximal opening and a distal portion with a distal opening. The distal portion may be engaged with the proximal portion. The elongated inner body may be disposed partially within the outer body and may extend from a distal inner body opening to a proximal inner body opening. The first plate may have a first proximal surface and a first distal surface. The first plate may be disposed on the inner body. The second plate may have a second proximal surface and a second distal surface. The second proximal surface may be disposed on the first proximal surface. The insulator may be disposed between the inner body and the first and second plates such that the first and second plates may be configured as a first electrode and the outer body may be configured as a second electrode of the electrosurgical device.

In accordance with the sixth aspect, a first material of the first plate may be different from a second material of the second plate. The first plate may be made of tungsten and the second plate may be made of stainless steel.

In accordance with a seventh aspect of the present disclosure, an electrosurgical device for arthroscopic procedures is provided. An electrosurgical device according to this aspect may include an elongated outer body, an elongated inner body, a plate and an insulator. The elongated outer body may have a proximal portion with a proximal opening and a distal portion with a distal opening. The distal portion may be engaged with the proximal portion. The elongated inner body may be disposed partially within the outer body and may extend from a distal inner body opening to a proximal inner body opening. The plate may have a proximal surface and a distal surface. The plate may be disposed on the inner body. The insulator may be disposed between the inner body and the first and second plates such that the first and second plates may be configured as a first electrode and the outer body may be configured as a second electrode of the electrosurgical device. An inlet area for fluid flow to the inner body may be defined by a gap between the plate and the insulator. The inlet area may be configured to remain constant during plate erosion.

In accordance with an eight aspect of the present disclosure, a method for ablating tissue with an electrosurgical device is provided. A method in accordance with this aspect may include the steps of positioning a distal end of an electrosurgical device at a target surgical site and delivering ablative energy through the distal end to a target tissue at the target surgical site without contacting a plate with the target tissue. The electrosurgical device may have an inner body disposed within an outer body, an insulator between the inner body and the plate. The plate may be configured as a first electrode and the outer body may be configured as a second electrode. The insulator may include a pad extending distally such that a distal surface of the plate may be proximal to a distal surface of the pad to prevent contact between the plate and the target tissue.

In accordance with a ninth aspect of the present disclosure, a method for ablating tissue with an electrosurgical device is provided. A method in accordance with this aspect may include the steps of positioning a distal end of an electrosurgical device at a target surgical site, delivering ablating energy through the distal end to a target tissue at the target surgical site, providing a suction force to a fluid channel to remove a fluid from the target surgical site, and maintaining a constant inlet area during the ablation process to provide a constant flow rate through the fluid channel. The electrosurgical device may have an inner body disposed within an outer body, an insulator between the inner body and a plate. The plate may be configured as a first electrode and the outer body being configured as a second electrode. The inner body may have the fluid channel in communication with an inlet. The inlet may have an inlet area being defined by a gap between the plate and the insulator. The suction force may remove the fluid from the target surgical site through the inlet. The erosion of the plate during the ablation process may not change the inlet area between the electrode and the insulator.

In accordance with a tenth aspect of the present disclosure, any of the electrosurgical devices described above may be used in robotic applications. Any of the electrosurgical devices may be used in combination with an imaging procedure. The imaging procedure may include a fluorescence imaging procedure. The fluorescence imaging procedure may include the use of a fluorescence imaging agent. The fluorescence imaging agent may include indocyanine green ("ICG"), conjugates thereof and derivatives thereof.

In accordance with an eleventh aspect of the present disclosure, a kit for orthopaedic procedure is provided. The kit may include any of the electrosurgical devices described above and a fluorescence imaging agent. The orthopaedic procedure may include an arthroscopic procedure.

In accordance with a twelfth aspect of the present disclosure, an electrosurgical device for use in arthroscopic procedures is provided. An electroscopic device according to this aspect may include an elongated outer body, an elongated inner body, a plate and an insulator. The elongated outer body may have a proximal portion with a proximal opening and a distal portion with a distal opening. The distal portion may be engaged with the proximal portion. The distal portion may have a central longitudinal axis extending from a first portion to a second portion defining a bend angle therebetween. The elongated inner body may be disposed within the outer body and may extend from a distal inner body opening to a proximal inner body opening. The inner body may be straight and define a dimension such that the inner body may extend through the first and second portions of the distal portion. The plate may have a proximal surface and a distal surface. The plate may be disposed on the inner body. The insulator may be disposed between the inner body and the plate such that the plate may be configured as a first electrode and the outer body may be configured as a second electrode of the electrosurgical device.

In accordance with a thirteenth aspect of the present disclosure, an electrosurgical device for use in arthroscopic procedures is provided. An electrosurgical device according to this aspect may include an elongated outer body, an elongated inner body, a plate and an insulator. The elongated outer body may extend between a proximal end and a distal end. The elongated inner body may be disposed partially within the outer body, a distal portion of the elongated inner body may at least partially extend from the distal end of the elongated outer body. The plate may have a proximal surface and a distal surface, the plate may be connected to the distal portion of the inner body. The insulator may separate the inner body and the plate from the outer body such that the plate is configured as a first electrode and the outer body is configured as a second electrode of the electrosurgical device. A first aperture may extend through the plate to provide fluid connection between the first aperture and the elongated inner body. The first aperture may define a first open area. A second aperture may be defined by a proximal surface of the plate and a distal surface of the insulator. The second aperture may be transverse to the first aperture and provide a fluid connection to the elongated inner body. A second open area may be defined by the second aperture and may be greater than the first open area. The second open area may be less than or equal to the first open area.

In accordance with the thirteenth aspect, the elongated outer body may include a first outer body and a second outer body. The first outer body may include a proximal portion and the second outer body may include a distal portion such that the first outer body may overlap at least a portion of the second outer body along a central axis of the elongated outer body. The inner body may include a flexible region disposed between a proximal inner body opening and a distal inner body opening. The flexible region may include one or more cut-outs. The one or more cut-outs may be u-shaped slots extending transversely across the inner body.

Still further in accordance with the thirteenth aspect, the plate may include at least one serrated edge. The first and second apertures may be inlets to transport fluids from a surgical site to the inner body. The distal inner body opening may include at least one projection extending away from the distal inner body opening and the plate may include at least one recess extending between the proximal surface and the distal surface such that the at least one projection may be received in the at least one recess when the plate is disposed on the inner body. The second open area may be defined by a distance between the proximal surface of the plate and the distal surface of the insulator. The insulator may have an insulator aperture extending through the insulator. The insulator aperture may have an insulator aperture cross-sectional area. The plate may define a plate cross-sectional area greater than the insulator aperture cross-sectional area. The plate may define a plate cross-sectional area less than or equal to the insulator aperture cross-sectional area.

In accordance with a fourteenth aspect of the present disclosure, an electrosurgical device for use in arthroscopic procedures is provided. An electrosurgical device according to this aspect may include an elongated outer body, an elongated inner body, a plate and an insulator. The elongated outer body may extend between a proximal end and a distal end. The elongated inner body may be disposed partially within the outer body. A distal portion of the elongated inner body may include at least one prong partially extending from the distal end of the elongated outer body. The plate may have a proximal surface and a distal surface. The plate may be connected to the at least one prong of the inner body. The insulator may separate the inner body and the plate from the outer body such that the plate may be configured as a first electrode and the outer body may be configured as a second electrode of the electrosurgical device. A first aperture may extend through the plate to provide fluid connection between the first aperture and the elongated inner body. The first aperture may define a first open area. A second aperture may be defined by a gap between a proximal surface of the plate and a distal surface of the insulator. The second aperture may provide a fluid connection to the elongated inner body. The plate and the insulator may not contact one another.

In accordance with the fourteenth aspect, at least a peripheral surface of the plate may extend past a peripheral surface of an insulator aperture, the insulation aperture may be in fluid communication with the inner body and the first aperture. At least a peripheral surface of an insulator aperture may extend past a peripheral surface of the plate, the insulation aperture being in fluid communication with the inner body and the first aperture.

In accordance with a fifteenth aspect of the present disclosure, an electrosurgical device includes an elongated outer body extending between a proximal end and a distal end; an elongated inner body disposed partially within the outer body, a distal portion of the elongated inner body at least partially extending from the distal end of the elongated outer body; a plate having a proximal surface and a distal surface, the plate being connected to the distal portion of the inner body; and an insulator separating the plate from the outer body such that the plate is configured as a first electrode and the outer body is configured as a second electrode of the electrosurgical device. The first electrode is separated from and does not contact the insulator, such that an aperture is present proximal of the electrode and distal of the spacer. Another aperture may be positioned through the plate. Both apertures may be in fluid communication with the inner body. Further, the distal portion of the inner body may include at least one prong, and the plate may be connected to the at least one prong, for example, the end of the at least one prong may connect to an at least one respective recess in the plate.

In accordance with a sixteenth aspect of the present disclosure, a method for ablating tissue with an electrosurgical device is provided. A method in accordance with this aspect may include the steps of positioning a distal end of an electrosurgical device at a target surgical site, delivering ablating energy through the distal end to a target tissue at the target surgical site and providing a suction force to a fluid channel to remove a fluid from the target surgical site. The electrosurgical device may have an inner body disposed within an outer body, an insulator between the inner body and a plate. The plate may be configured as a first electrode and the outer body being configured as a second electrode. The inner body may have the fluid channel in communication with first and second inlets. The first inlet having an inlet area defined by a gap between a proximal surface of the plate and a distal surface of the insulator. The second inlet being defined by an aperture extending through the plate. The suction force may remove the fluid from the target surgical site through any of the first and second inlets. Further, the first inlet may provide sufficient fluid flow for continued operation of the electrosurgical device even in instances where the plate, and thus the second inlet, is positioned against tissue such that minimal or no suction flow exists through the second inlet.

In accordance with a seventeenth aspect of the present disclosure, an electrosurgical device for use in arthroscopic procedures is provided. An electrosurgical device according to this aspect may include an elongated outer body, an elongated inner body, a plate and an insulator. The elongated outer body may extend between a proximal end and a distal end. The elongated inner body may be disposed partially within the outer body. A distal portion of the elongated inner body may include at least one prong partially extending from the distal end of the elongated outer body. The plate may have a proximal surface and a distal surface. The plate may be connected to the at least one prong of the inner body. The insulator may separate the inner body and the plate from the outer body such that the plate may be configured as a first electrode and the outer body may be configured as a second electrode of the electrosurgical device. A first aperture may extend through the plate to provide fluid connection between the first aperture and the elongated inner body. The first aperture may define a first open area. A second aperture may be defined by a gap between a proximal surface of the plate and a distal surface of the insulator. The second aperture may provide a fluid connection to the elongated inner body. The gap may completely separate the plate from the insulator.

In accordance with an eighteenth aspect of the present disclosure, a method for ablating tissue with an electrosurgical device is provided. A method in accordance with this aspect may include the steps of positioning a distal end of an electrosurgical device at a target surgical site, contacting a target tissue with a distal surface of a plate, delivering ablating energy through the distal end to a target tissue at the target surgical site and providing a suction force to a fluid channel to remove a fluid from the target surgical site. The electrosurgical device may have an inner body disposed within an outer body, an insulator between the inner body and a plate. The plate may be configured as a first electrode and the outer body being configured as a second electrode. The inner body may have the fluid channel in communication with a first inlet. The first inlet may have an inlet area defined by a gap between a proximal surface of the plate and a distal surface of the insulator. The suction force may remove at least a portion of the fluid from the target surgical site through the first inlet.

In accordance with a nineteenth aspect of the present disclosure, an electrosurgical device for use in arthroscopic procedures is provided. The device may include an elongate outer body, an elongate inner body, a first plate, a second plate, a third plate and an insulator. The elongate inner body may have a cannulated portion with a proximal end and a distal end and may further include two projections that each extend distally from the distal end of the cannulated portion. The elongate inner body may be disposed partially within the elongate outer body. The first plate may have a plurality of apertures therethrough. The first plate may be positioned such that each of the two projections extends through a respective aperture of the plurality of apertures of the first plate. The second plate may have at least one aperture and may be disposed on the first plate such that one of the two projections extends through the at least one aperture of the second plate. Further, the second plate may be fixed to the at least one projection. The third plate may have at least one aperture and may be disposed on the first plate such that one of the two projections extends through the at least one aperture of the third plate. The third plate may be fixed to the at least one projection. The insulator may be disposed around the elongate inner body. The insulator may abut the elongate outer body at a first end and abut the first plate at a second end opposite the first end. The second plate and the third plate may be separated by a distance and at least one of the plurality of apertures of the first plate may be spaced from the second plate and the third plate. When electricity is supplied to the elongate inner body and a conductor is present at a distal end of the electrosurgical device, a closed circuit is formed and the first plate is a first electrode of the electrosurgical device and the elongate outer body is a second electrode of the electrosurgical device.

In some examples, the first, second and third plates, as a combination, may be symmetrical about a central longitudinal axis on a plane through the first plate that passes between the second plate and the third plate. In some examples, the plurality of apertures of the first plate may be include a first aperture, a second aperture and a third aperture directly between the first and second apertures. In some examples, the third aperture of the first plate may be defined by an internal edge of the first plate, the internal edge being spaced apart from the second plate and the third plate. In some examples, the first plate may be tungsten and the second and third plates may be stainless steel. In some examples, the first plate, the second plate and the third plate may be stainless steel. In some examples, each of the two projections may be welded, brazed or soldered to one of the second plate and the third plate and the first plate is held in place by its position in between the second plate and the insulator. In some examples, the first, second and third plates may together constitute the first electrode. In some examples, the two projections may each include a distal end that protrudes relative to a distal surface of the second plate and the third plate, respectively. In some examples, each of the second plate and the third plate may have a proximal surface perimeter that abuts the first plate in its entirety. In some examples, each of the second plate and the third plate may include four sides, the second plate and the third plate being symmetrical to one another about a central longitudinal axis on a plane through the first plate. In some examples, each of the second plate and the third plate may have a first distally facing surface area and the first plate may have a second distally facing surface area, the first distally facing surface area being less than 50% of the second distally facing surface area, or preferably, less than 25% of the second distally facing surface area.

In accordance with a twentieth aspect of the present disclosure, an electrosurgical device for use in arthroscopic procedures is provided. The device may include an elongate outer body, an elongate inner body, a first plate, a second plate and an insulator. The elongate inner body may have a cannulated portion with a proximal end and a distal end. At least one projection may extend distally from the distal end of the cannulated portion. The elongate inner body may be disposed partially within the elongate outer body. The first plate may have a first aperture and a second aperture therethrough. The second aperture of the first plate may include a first, second and third segment. The first segment may have a first length and the second and third segments may each be shorter than the first segment and be transverse to the first segment. The first plate may be positioned such that the at least one projection extends through the first aperture of the first plate. The second plate may have at least one aperture and may be disposed on the first plate such that the at least one projection extends through the at least one aperture of the second plate. The second plate may be fixed to the at least one projection. The insulator may be disposed around the elongate inner body and may abut the elongate outer body at a first end and abut the first plate at a second end opposite the first end. When electricity is supplied to the elongate inner body and a conductor is present at a distal end of the electrosurgical device, a closed circuit is formed and the first plate is a first electrode of the electrosurgical device and the elongate outer body is a second electrode of the electrosurgical device.

In some examples, the first, second and third segments of the second aperture may be entirely linear and the first segment may be perpendicular to each of the second segment and the third segment. In some examples, the first plate may include third and fourth apertures separated by the second aperture, each of the third and fourth apertures being single arcuate shaped segments. In some examples, the third and fourth apertures of the first plate may be positioned directly over a lumen of the insulator and the second aperture may be positioned directly over a lumen of the elongate inner body. In some examples, the first plate may be tungsten and the second plate may be stainless steel.

In accordance with a twenty-first aspect of the present disclosure, an electrosurgical device for use in arthroscopic procedures is provided. The device may include an elongate outer body, an elongate inner body, a first plate, a second plate and an insulator. The elongate inner body may have a cannulated portion with a proximal end and a distal end and a projection extending distally from the distal end of the cannulated portion. The elongate inner body may be disposed partially within the elongate outer body. The first plate may have a first aperture and a second aperture therethrough. The second aperture may be positioned closer to a center of the first plate than the first aperture. The first plate may be positioned such that the projection extends through the first aperture. The second plate may have at least one aperture and may be disposed on the first plate. The projection may extend through the at least one aperture of the second plate, the second plate being fixed to the projection. The insulator may be disposed around the elongate inner body and may be positioned such that the insulator and the elongate inner body are on a single side of the first plate. The projection may protrude from a distal end surface of the second plate. The first plate may be tungsten and the second plate may be stainless steel. When electricity is supplied to the elongate inner body and a conductor is present at a distal end of the electrosurgical device, a closed circuit is formed and the first plate is a first electrode of the electrosurgical device and the elongate outer body is a second electrode of the electrosurgical device.

In some examples, the second plate may include a proximal surface perimeter edge that abuts the first plate in its entirety. In some examples, the projection may not be fixed to the first plate.

In accordance with a twenty-second aspect of the present disclosure, an electrosurgical device for use in arthroscopic procedures is provided. The device may include an elongate outer body, an elongate inner body, a first plate and an insulator. The elongate inner body may have a cannulated portion extending from a proximal end to a distal end and at least one projection, or preferably, two projections. Each of the projections may extend distally from the distal end of the cannulated portion. The elongate inner body may be disposed partially within the elongate outer body. The first plate may have at least one passage therethrough, and preferably, a plurality of passages therethrough. The first plate may be positioned such that each of the projections extends through a respective passage of the plurality of passages of the first plate. The insulator may be disposed around the elongate inner body. The insulator may abut the elongate outer body at a first end and abut the first plate at a second end opposite the first end. A closed circuit may be formed and the first plate is a first electrode of the electrosurgical device and the elongate outer body is a second electrode of the electrosurgical device when electricity is supplied to the elongate inner body and a conductor is present at a distal end of the electrosurgical device.

In accordance with the twenty-second aspect, at least one of the projections, and preferably the two projections, extending through a respective passage of the plurality of passages of the first plate may be welded to the first plate to prevent pullout of the first plate from the elongate inner body.

In accordance with the twenty-second aspect, at least one of the projections, and preferably the two projections, extending through a respective passage of the plurality of passages of the first plate may be deformed to prevent pullout of the first plate from the elongate inner body. The projection or projections may be deformed by thermal staking.

Further in accordance with the twenty-second aspect, the electrosurgical device may include a second plate and a third plate. The second plate may be disposed on the first plate and fixed to the at least one projection. The third plate may be disposed on the first plate and fixed to the at least one projection. The first plate may be a first material and the second and third plates may be a second material with a melting temperature and corrosion resistance lower than that of the first material. The first material may be tungsten and the second material may be stainless steel.

Still further in accordance with the twenty-second aspect, the plurality of passages of the first plate may include a first aperture, a second aperture and a third aperture. A projected area of the first aperture on the distal end of the inner body may be entirely within the inner body such that fluid entering the plate via the first aperture may directly enter the inner body through a distal opening of the inner body. A projected area of the second aperture on the distal end of the inner body may be entirely outside the inner body such that fluid entering the plate via the second aperture may enter the inner body through a side opening of the inner body. A projected area of the third aperture on the distal end of the inner body may be partially inside and partially outside the inner body such that fluid entering the plate via the third aperture may partially enter the inner body through a side opening of the inner body and may partially enter the inner body directly through the distal opening of the inner body. Any combinations or variations are also envisioned, such as where the first, second, and third apertures are one single, large aperture that projects an area on the distal end of the inner body that is at least partially within the inner body and at least partially outside the inner body.

BRIEF DESCRIPTION OF THE DRAWINGS

A more complete appreciation of the subject matter of the present disclosure and the various advantages thereof may be realized by reference to the following detailed description, in which reference is made to the following accompanying drawings:

FIG. 2 is side perspective view of a distal portion of an outer body of the RF probe of FIG. 1;

FIG. 3 is a side perspective view of a proximal portion of the outer body of the RF probe of FIG. 1;

FIG. 18 is a side perspective view of an RF probe according to another embodiment of the present disclosure;

FIG. 19 is a side perspective view of an RF probe according to another embodiment of the present disclosure;

FIGS. 46A and 46B are close up partial perspective views of the RF probe of FIG. 43;

DETAILED DESCRIPTION

Reference will now be made in detail to the various embodiments of the present disclosure illustrated in the accompanying drawings. Wherever possible, the same or like reference numbers will be used throughout the drawings to refer to the same or like features. It should be noted that the drawings are in simplified form and are not drawn to precise scale. Additionally, the term "a," as used in the specification, means "at least one." The terminology includes the words above specifically mentioned, derivatives thereof, and words of similar import. Although at least two variations are described herein, other variations may include aspects described herein combined in any suitable manner having combinations of all or some of the aspects described.

As used herein, the terms "RF probes" and "electrosurgical devices" will be used interchangeably and as such, unless otherwise stated, the explicit use of either term is inclusive of the other term. The term "RF probe" is used to denote the RF probe distal tip, variations of which are described in the present disclosure.

In describing preferred embodiments of the disclosure, reference will be made to directional nomenclature used in describing the human body. It is noted that this nomenclature is used only for convenience and that it is not intended to be limiting with respect to the scope of the invention. For example, as used herein, when referring to RF probe, the term "distal" means toward the human body and/or away from the operator, and the term "proximal" means away from the human body and/or towards the operator.

Figure 1:
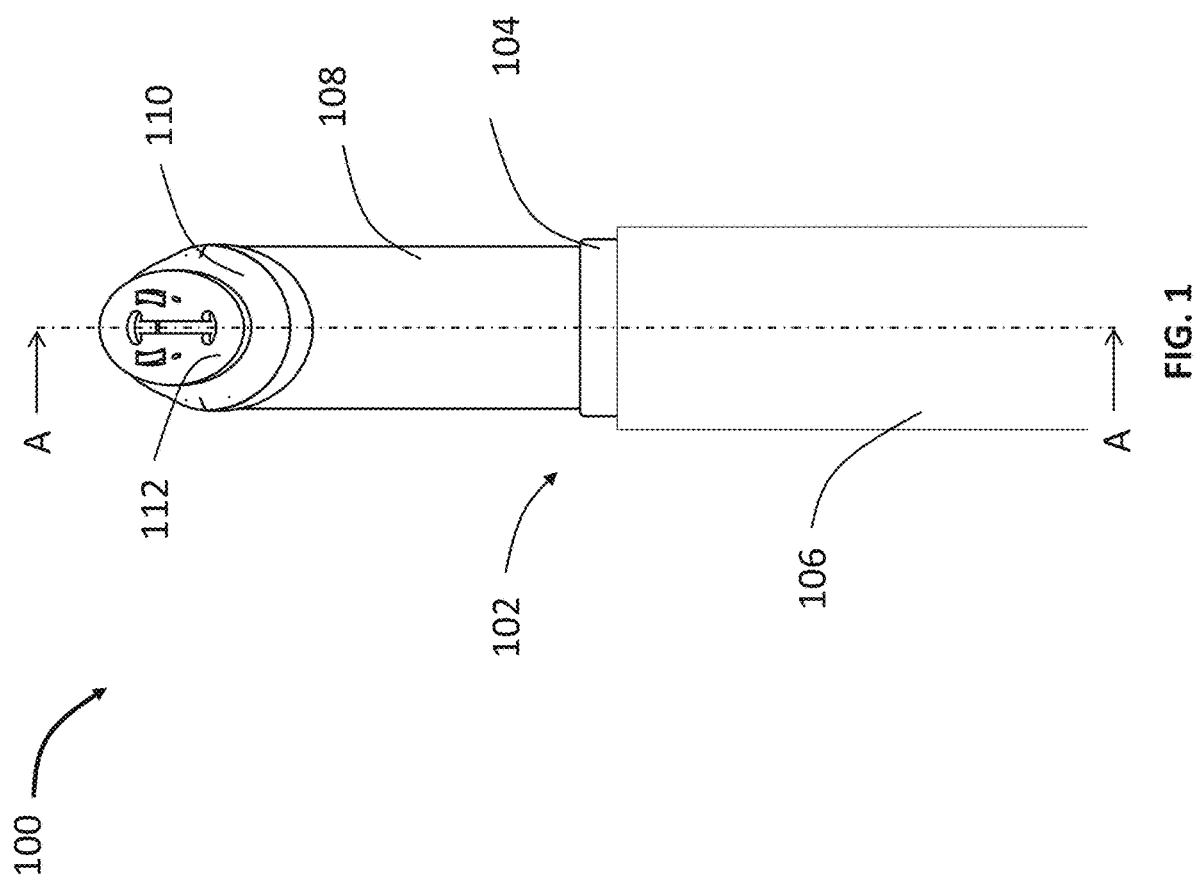
FIG. 1 is a front view of an electrosurgical device, such as an RF probe, according to one embodiment of the present disclosure.

Referring to FIG. 1, there is shown an RF probe 100 according to one embodiment of the present disclosure. RF probe 100 includes an outer body 102 having a distal portion 108 and a proximal portion 104. A handle (not shown) can be joined to a proximal end of proximal portion 104. The handle may be any as known in the art. The handle can include controls to allow a user to operate RF probe 100. An insulator sleeve, e.g., heat shrink tubing 106, can be positioned around proximal portion 104 to provide insulation and abrasion resistance during RF probe use. A distal end of probe 100 includes an insulator 110 and a plate 112. The materials of construction of probe 100 may be any desired or useful materials to manufacturing and use of probe 100, as discussed in greater detail below. For example, in an embodiment, the proximal portion 104 may be made from heat treated precipitation-hardened stainless steel such as 17-7PH stainless steel or other similar materials to provide for a strong and stiff shaft, which may be useful when using the probe in certain orthopedic applications where forces exerted on the probe are relatively high, such as hip arthroscopy. Further, for example, in an embodiment, the distal portion 108 may be made of 304 stainless steel tube, which is more malleable than 17-7PH stainless steel, which allows the distal portion to be bent without collapsing an inner diameter of the distal portion. Insulator 110 can be a ceramic insulator or other similar type of insulator. Plate 112 may be made of, for example, 316 stainless steel in this embodiment. An outer perimeter of plate 112 can be less than an outer perimeter of distal portion 108 as shown in FIG. 1. In another embodiment, the outer perimeter of plate 112 can be equal to or greater than an outer perimeter of distal portion 108.

Details of distal portion 108 are shown in FIG. 2. Distal portion 108 includes a proximal opening 114 and a distal opening 115. A central longitudinal axis 117 extending from proximal opening 114 to distal opening 115 is angled at the distal end with respect to the proximal end. As explained above, a malleable material is selected for distal portion to allow for bending during manufacture while maintaining the inner diameter of distal portion 108 as shown in FIG. 2. A u-shaped slot 116 extends from proximal opening 114 along axis 117. The u-shaped slot has a width 118 sized to allow for passage of inner body 124 as more fully explained below. While a u-shaped slot is shown in this embodiment, other embodiments can have differently shaped slots such as a v-shaped slot, a circular slot, etc. to allow passage of the inner body through same. In other embodiments, the distal opening may be configured to have a small bend angle with respect to the proximal end such that a straight inner body may pass through the distal portion.

FIG. 3 shows details of proximal portion 104. Proximal portion 104 includes a proximal opening 120 and a distal opening 122. A central longitudinal axis 119 extends along the length of the proximal portion. Distal opening 122 has a larger inner diameter than distal portion 108 at proximal opening 114 to allow the proximal portion to fit over the distal portion. As illustrated, the proximal portion fitting over the distal portion allows for the u-shaped slot 116 to be covered, which results in a continuous, enclosed outer body 102.

Figure 4:
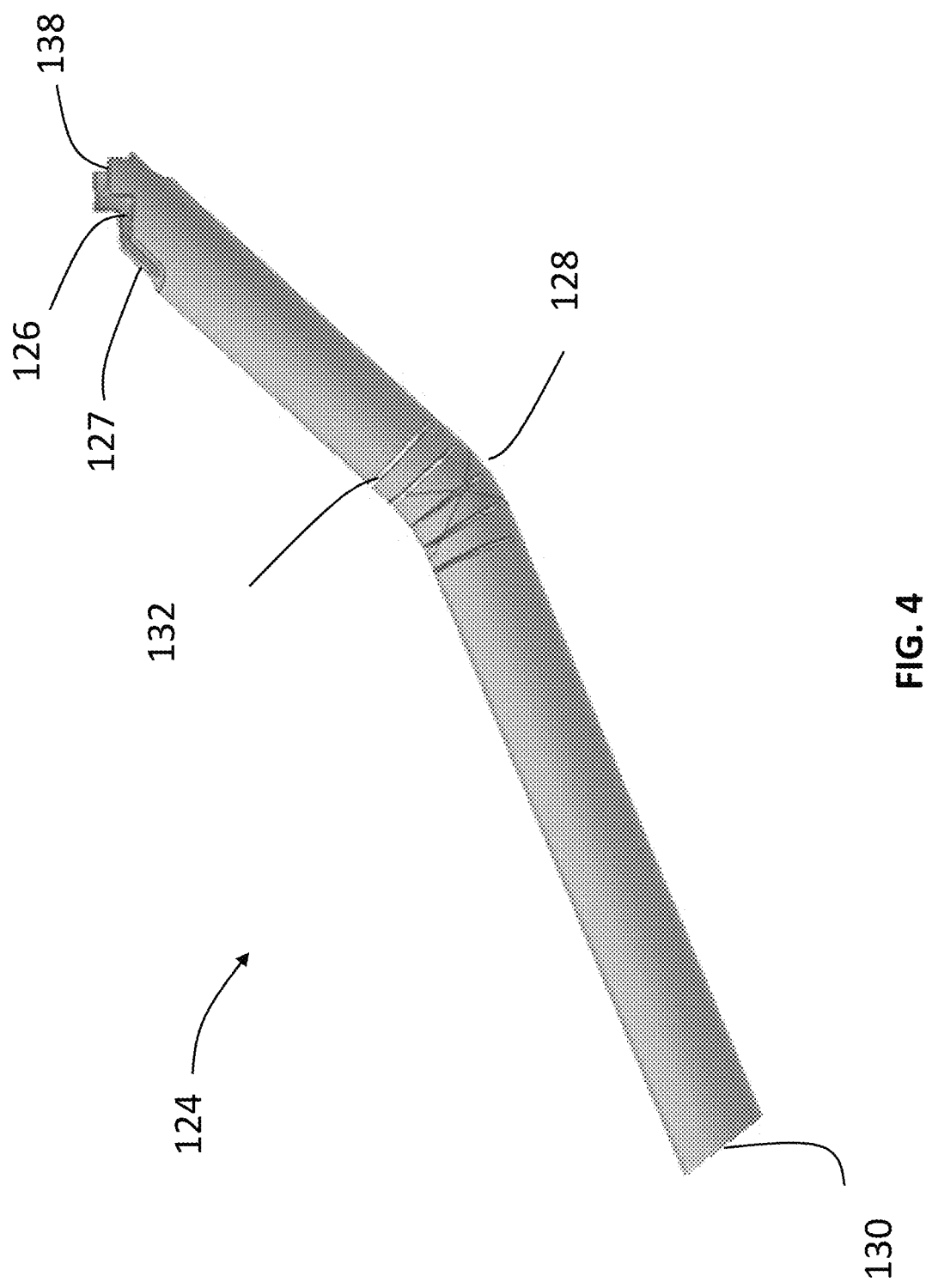
FIG. 4 is a side perspective view of an inner body of the RF probe of FIG. 1.
Figure 5:
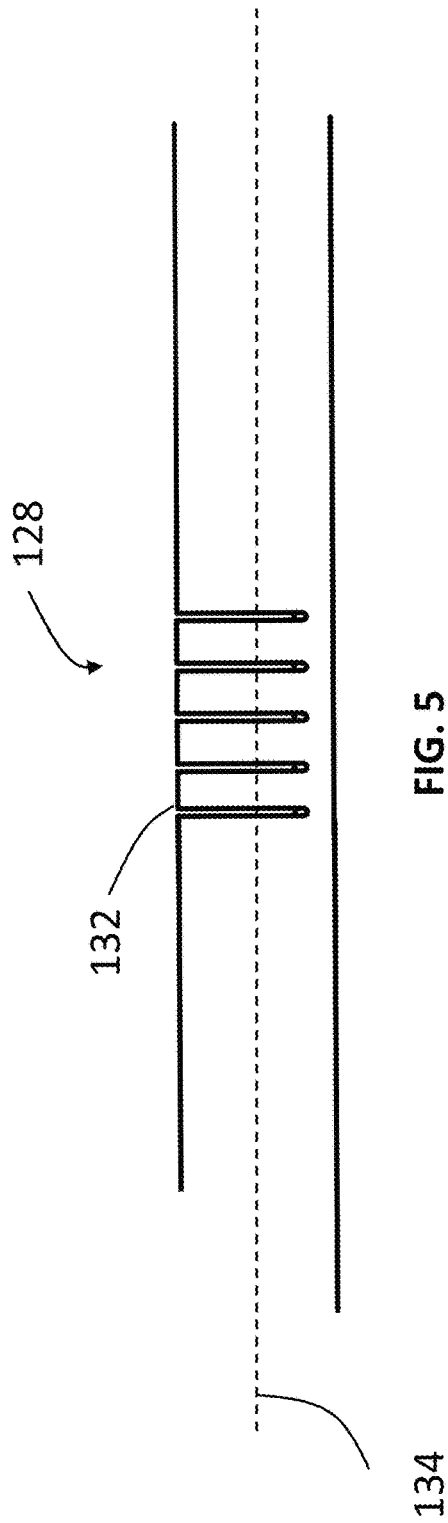
FIG. 5 is a side view of a flexible region of the inner body of FIGS. 1 and 4 in a first position.
Figure 6:
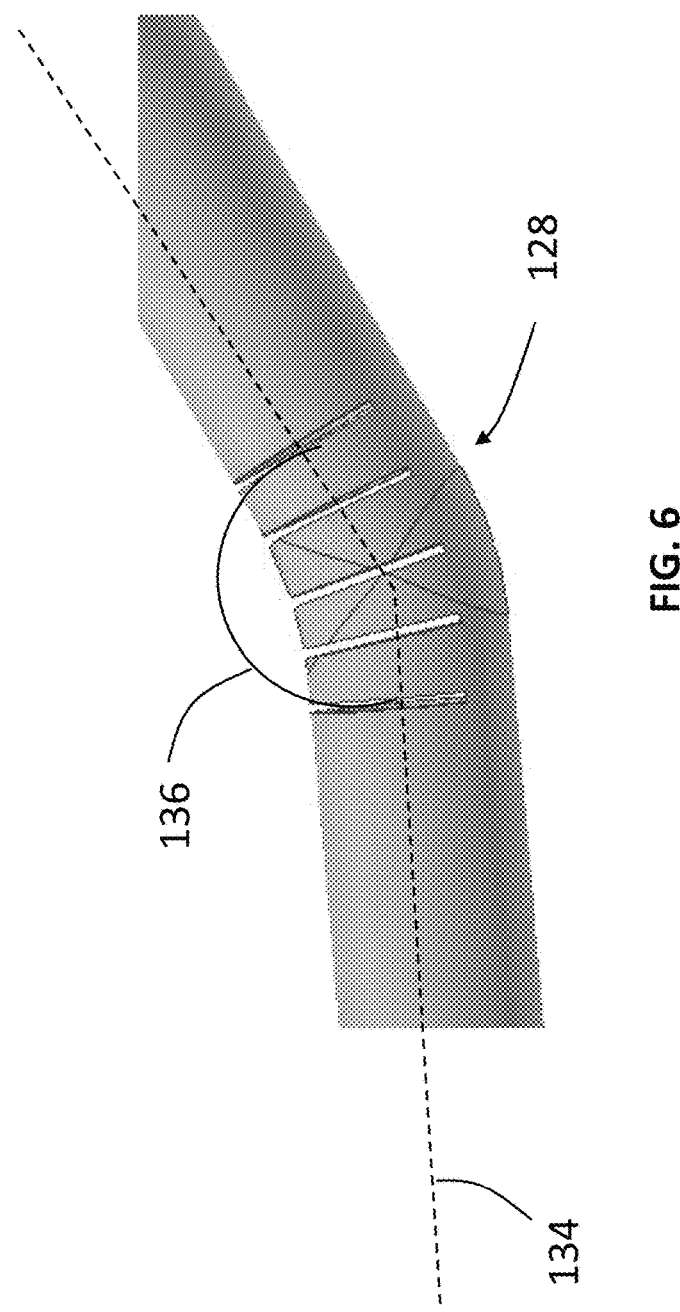
FIG. 6 is a side view of the flexible region of the inner body of FIG. 5 in a second position.

Referring now to FIG. 4, there are shown details of inner body 124. Inner body 124 includes a proximal opening 130 and a distal opening 126. Two side slots 127 (only one visible in FIG. 4) extend from distal opening 126 toward proximal opening 130. Side slots 127 provide additional fluid pathways to remove fluid from the surgical site as more fully explained below. Distal opening 126 includes at least one prong 138 (two prongs, as illustrated) extending away from the distal opening. Inner body 124 is made of 316L stainless steel tube in this embodiment. A flexible section 128 is disposed between proximal opening 130 and distal opening 126. As shown in FIGS. 5 and 6, flexible section 108 includes a plurality of cut-outs 132 shaped as u-slots extending transverse to a central longitudinal axis 134 of inner body 124. As illustrated, the slots are generally circumferential, though they could be positioned at an angle other than perpendicular as to the axis of inner body 124. The shape, number, and/or positioning of cut-outs 132 is based on the bending requirement of the inner body during assembly to ensure that the inner radius of the inner body remains constant. The inner body serves as the fluid conduit to remove fluid from the surgical site and therefore any reduction in the inner diameter of the inner body will impede or clog fluid flow during the RF probe ablation procedure. Tight bends at the distal end of the RF probes are often required to allow for proper access to various surgical sites. By way of example, a tight, large bend angle would require more cut-outs and/or wider cut-outs, whereas a gentler, smaller bend angle would require a smaller flexible portion with fewer cut-outs and/or thinner cut-outs. As best shown in FIG. 6, flexible portion 128 allows proper flexing and bending of inner body 124 without reduction in the inner diameter of the inner body.

Figure 7:
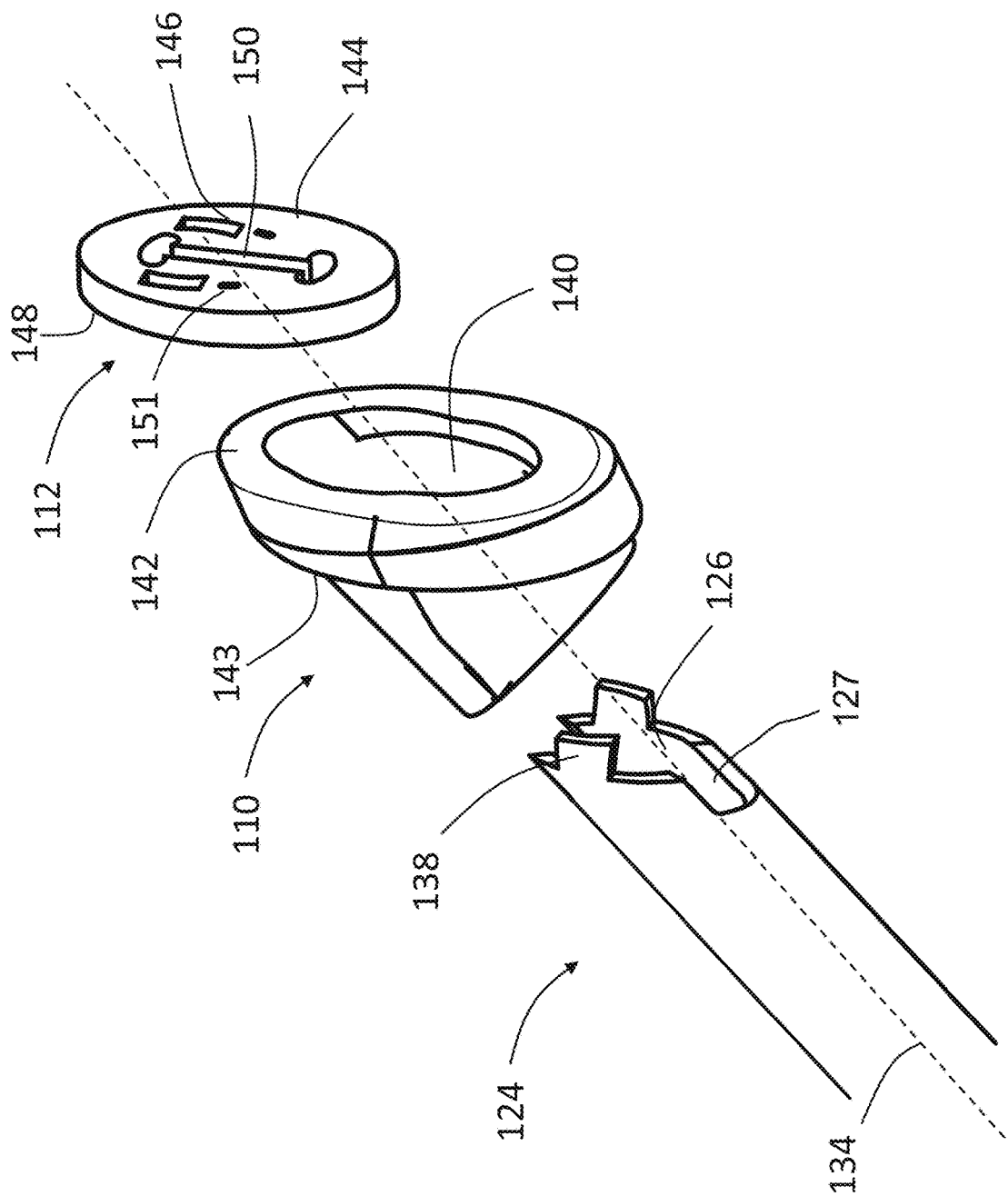
FIG. 7 is an exploded perspective view of the inner body, an insulator and a plate of the RF probe of FIG. 1.
Figure 8:
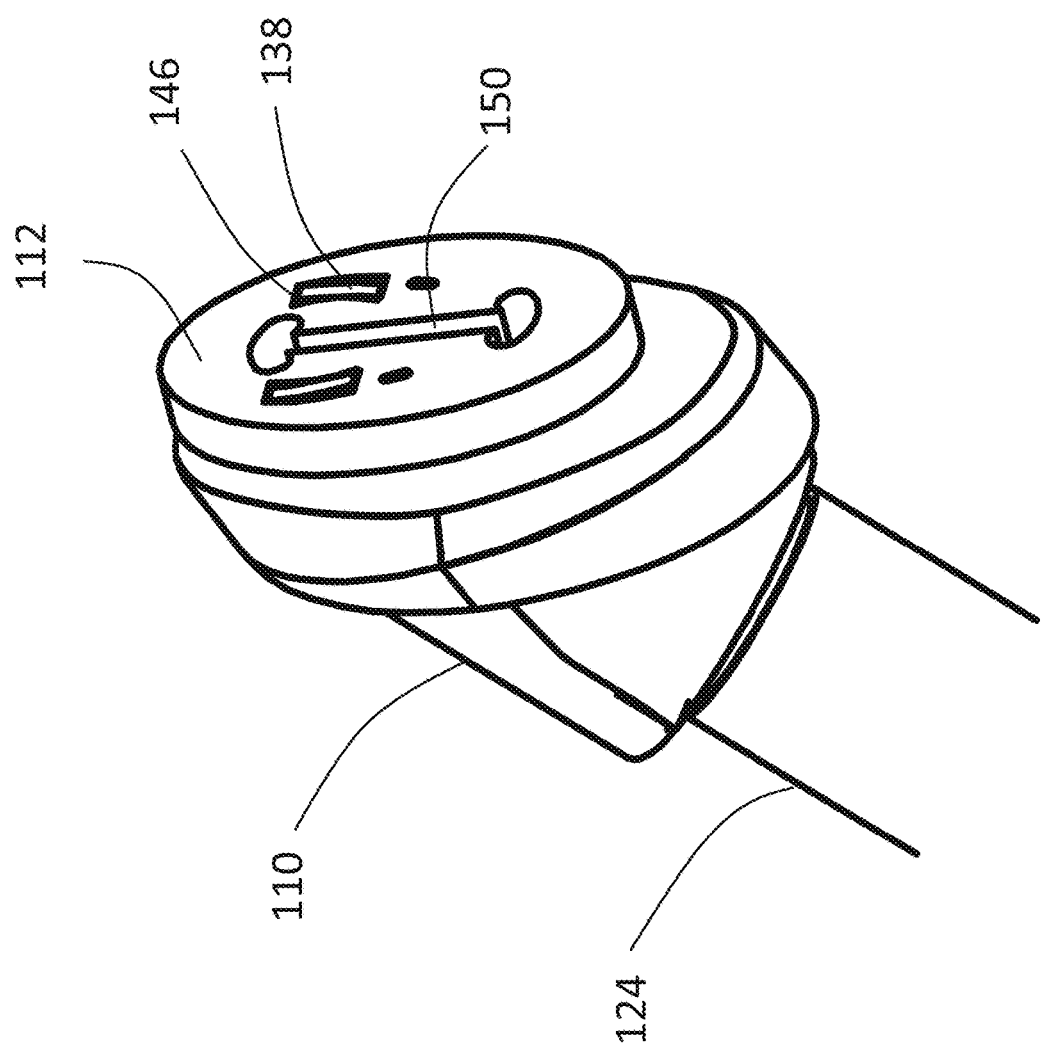
FIG. 8 is a side perspective view of the inner body, the insulator and the plate of the RF probe of FIG. 1.

FIGS. 7 and 8 show an exploded view and an assembled view of the distal end of RF probe 100 respectively. Insulator 110 includes an aperture 140 and a distal face 142. A center of aperture 140 is aligned with axis 134 of inner body in this embodiment. Plate 112 includes a distal surface 144 and a proximal surface 148. Two recesses 146 extending through plate 112 are configured to receive prongs 138 of inner body 124. Therefore, a continuous electric pathway between inner body 124 and plate 112 extending through aperture 140 of insulator 110 is created as best shown in FIG. 8. Plate 112 has a central aperture 150 aligned with axis 134 of inner body 124. Weld slots 151, along with recesses 146, on plate 112 facilitate attachment of inner tube 124 with the plate as more fully described below. When inner body 124, insulator 110 and plate 112 are assembled as shown in FIG. 8, a fluid path 125 with aperture 150 as the inlet is formed as shown in the cross-section of FIG. 9. While aperture 150 is illustrated as a single aperture with an I-shape, the plate 112 may instead have more than one aperture, and the one or more apertures may have any shape desired. Further, the one or more apertures can be positioned elsewhere on the plate 112 than at the central location as shown.

Figure 9:
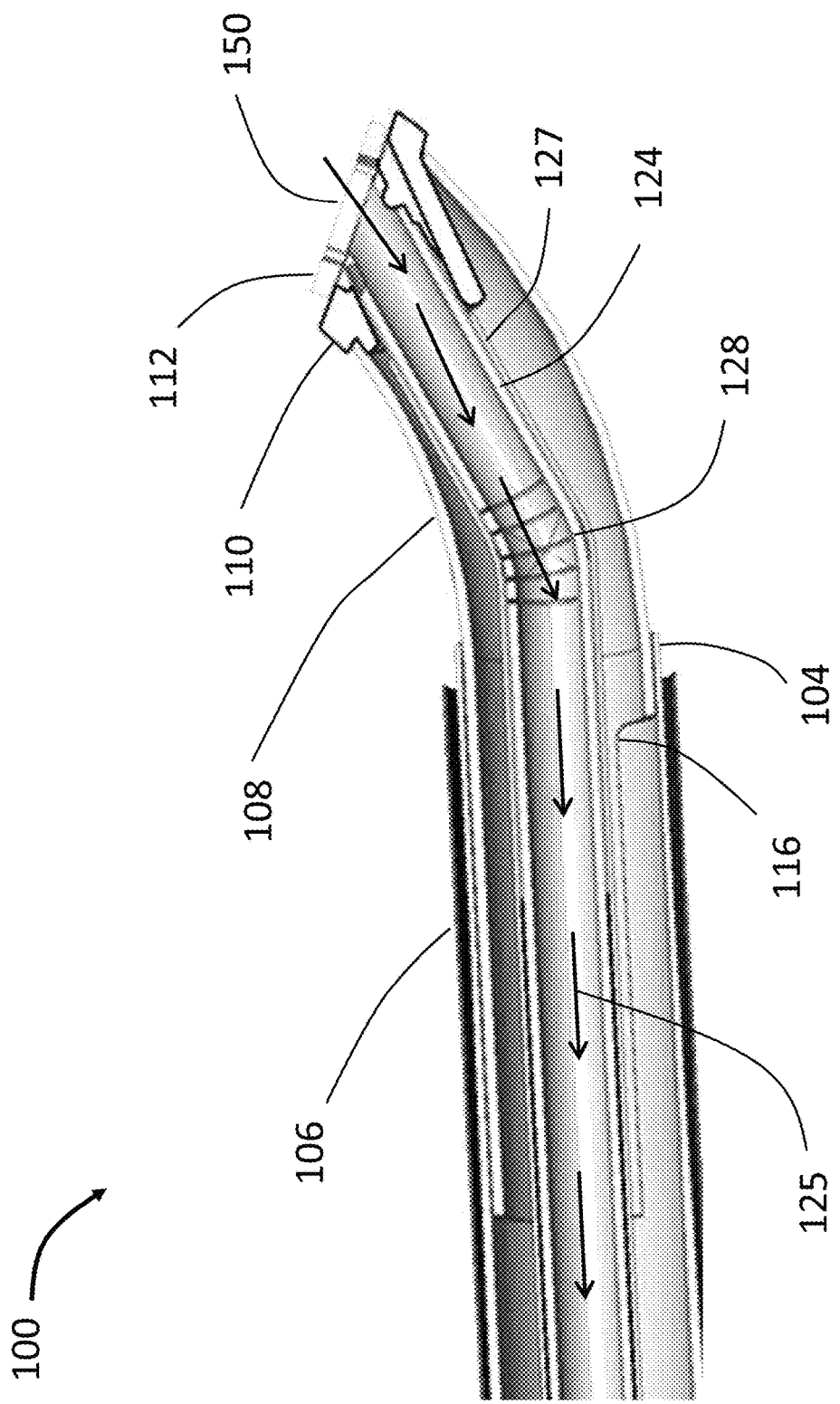
FIG. 9 is a cross-sectional view along line A-A of the RF probe of FIG. 1.
Figure 11:
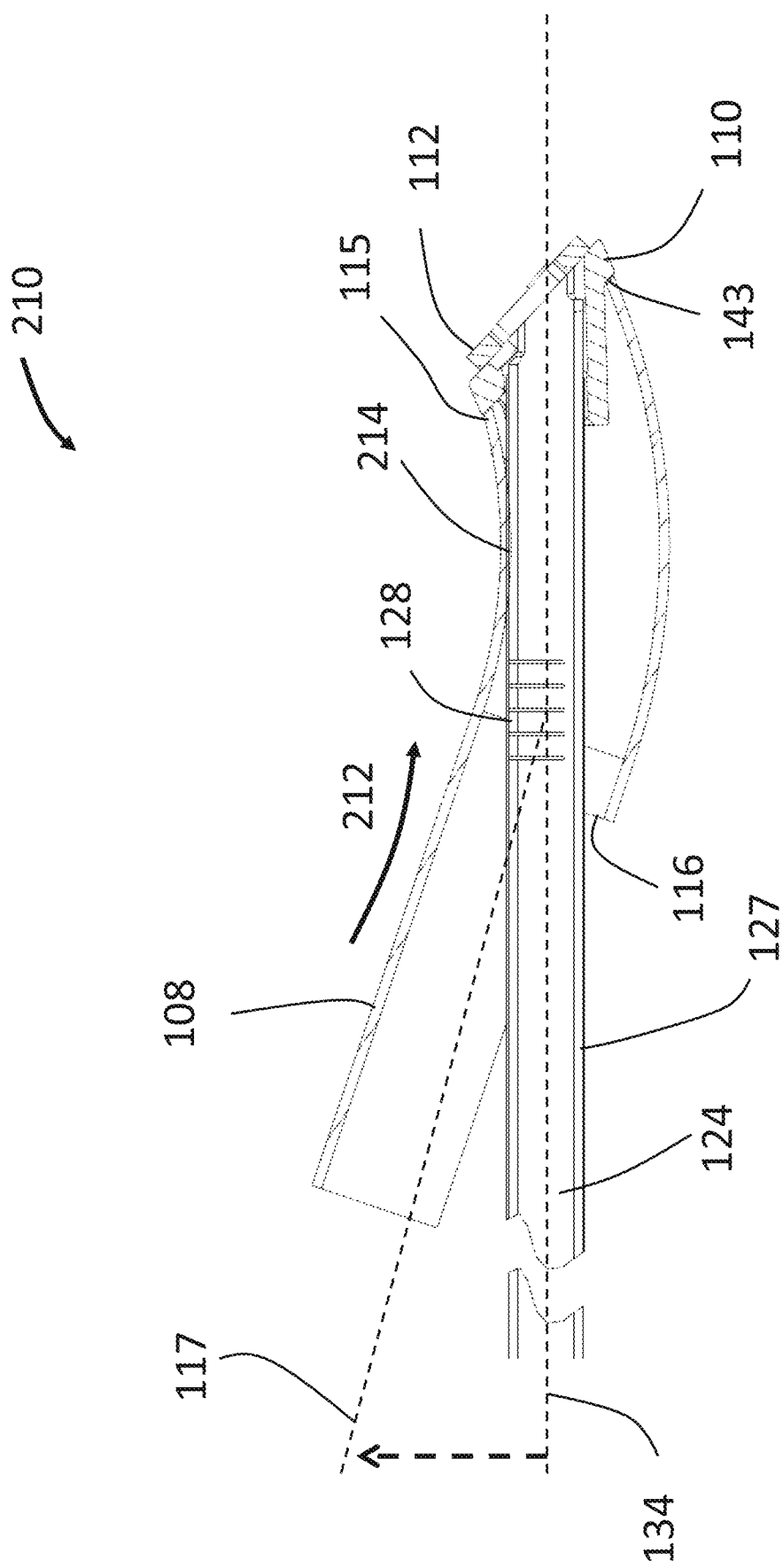
FIG. 11 is cross-sectional view of the RF probe assembly of FIG. 10B.

The continuous electric pathway between inner body 124 and plate 112 allow for the elimination of a wire or the like which is typically needed to electrify the plate (also commonly referred to as an electrode). The return electrode, which is also typically a wire, would in this embodiment be the outer body 102. As illustrated in FIGS. 9 and 11, for example, the inner body 124 and outer body 102 may, in addition to insulator 110, include another insulation layer 127 to maintain separation between inner body 124 and outer body 102 and prevent arcing. Insulation layer 127 can be made of an insulating material, such as a polymeric material or the like, which may enclose the outer surface of inner body 124 (and/or the inner surface of outer body 102) such that none of the metal body of inner body 124 directly faces the inner surface of the outer body 102. Insulation layer 127 could be, for example, heat-shrink tubing on the outer diameter of inner body 124 as best shown in FIGS. 9 and 11. Insulation layer 127 also seals fluid path 125 through inner body 124 to prevent fluid leakage. This seal may, for example, prevent fluid egress through cut-outs 132.

Figure 10A:
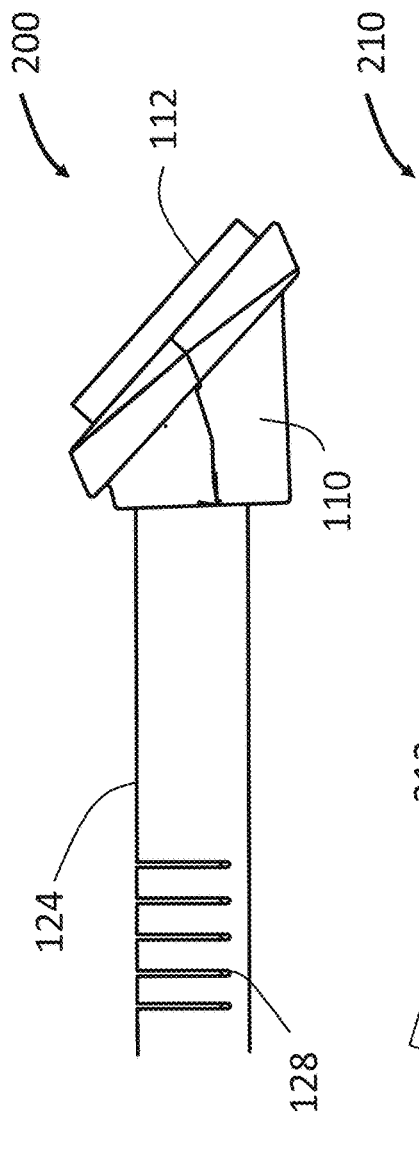
FIGS. 10A-10C show side perspective views of steps for assembling the RF probe of FIG. 1 according to another embodiment of the present disclosure.
Figure 10B:
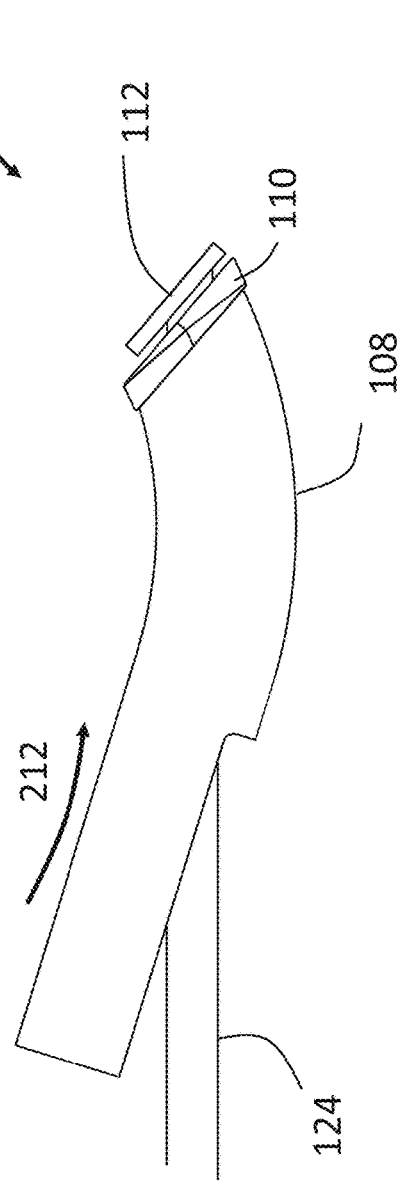
Figure 10C:
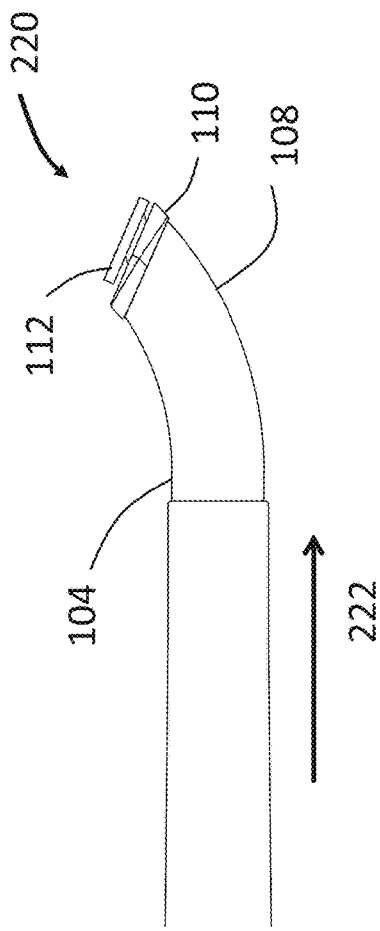

Referring now to FIGS. 10A-10C, there is shown a method for assembling RF probe 100 according to another embodiment of the present disclosure. In a first step 200, inner body 124 and plate 112 are attached through insulator 110 as shown in FIG. 10A. Insulator 110 is placed over inner body 124 by allowing the inner body to extend through aperture 140. Plate 112 is then placed over distal opening 126 of inner body 124 such that prongs 138 are within or extend through recesses 146 of the plate. Laser beam welding or any other fabrication technique can be used to attach and secure prongs 138 to plate 112. Weld slots 151 serve as markers to guide laser beam placement for precise welding of the prongs to plate 112. In addition to welding, other similar techniques may be employed, such as brazing and soldering.

FIGS. 10B and 11 show a step 210 wherein distal portion 108 of outer body 102 is placed over inner body 124 and insulator 110. Proximal opening 115 of distal portion 108 is placed over inner body 124 and advanced along a direction 212 until proximal opening 115 contacts a distal surface 143 of insulator 110 as best shown in FIG. 11. The unbent inner body 124 extends through u-slot 116 of distal portion 108 when the distal portion is advanced in step 210. The distal portion 108 and insulator 110 are secured to one another, whether through friction fit, adhesive, threaded connection, or the like.

In a step 220 shown in FIG. 10C, proximal portion 104 is placed over inner body 124 and distal portion 108 and advanced along a distal direction 222. As the proximal portion advances distally along 222, inner body 124 is bent to assume a curved shape similar to that of distal portion 108. A contact surface 214 between the inner body and proximal portion 108 serves as a support surface to bend the inner tube in conjunction with a bending force applied by the advancing proximal portion. Flexible section 128 allows for bending of inner body 124 without any reduction in internal diameter of fluid path 125. Therefore, RF probe 100 can be readily assembled by bending the inner body within the outer body and by using only the outer body, i.e., no other tooling is necessary for bending inner body.

Figure 12:
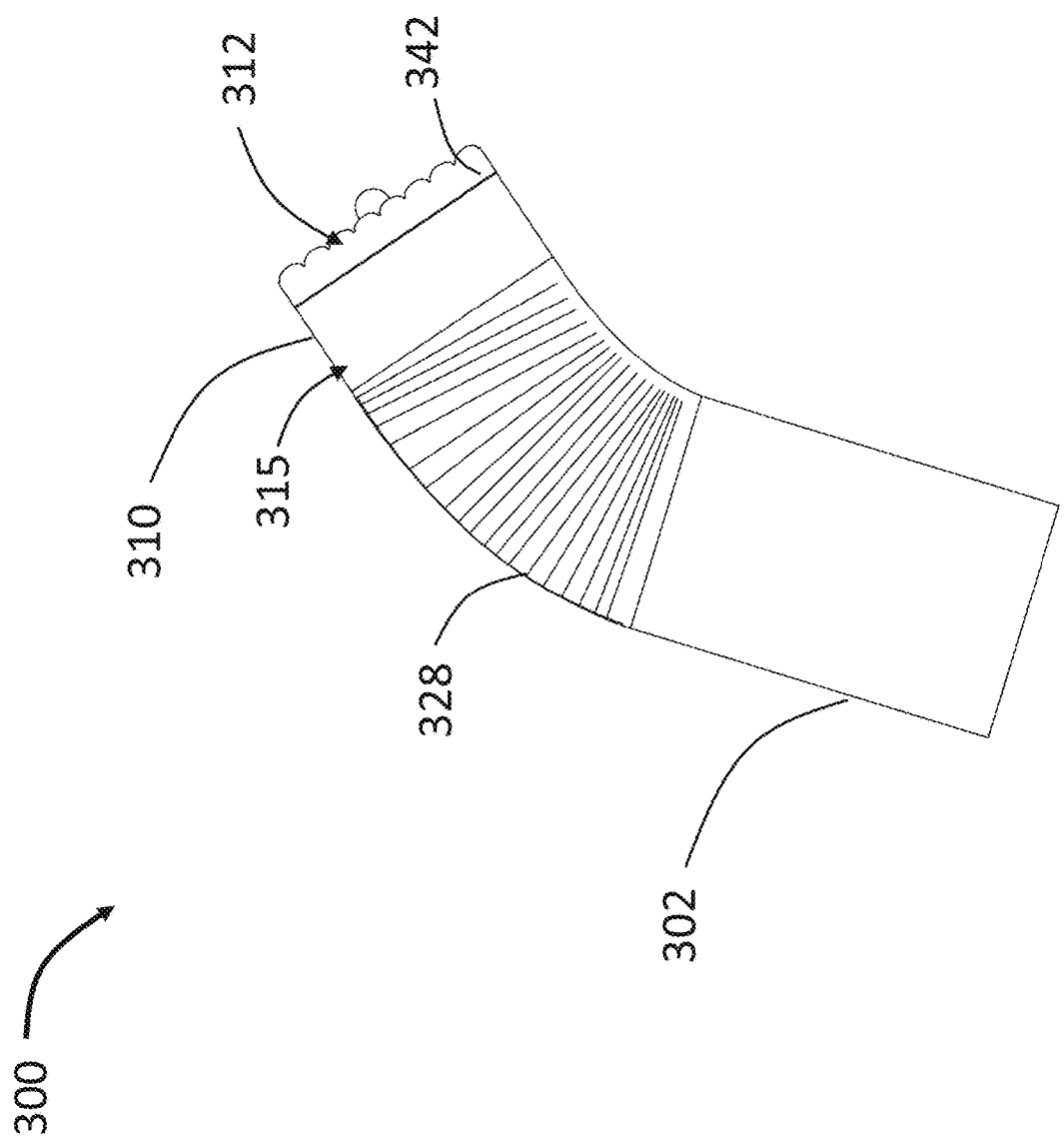
FIG. 12 is a side view of an RF probe according to another embodiment of the present disclosure.

Referring now to FIG. 12, there is shown an RF probe 300 according to another embodiment of the present disclosure. RF probe 300 is similar to RF probe 100, and therefore like elements are referred to with similar numerals within the 300-series of numbers. For example, RF probe 300 includes an outer body 302, an insulator 310 and a plate 312. However, RF probe 300 includes a flexible section 328 at the distal end of outer body 302. Flexible section 328 is positioned as close as possible to the distal end of outer body 302 while maintaining the rigidity of RF probe 300. Flexible section 328 is created by slicing, laser cutting or other similar procedures. After bending the outer body at the flexible section, the flexible section 328 may be locked in the bent position by the application of epoxy or other hardening agents to make flexible section 328 rigid. For example, the flexible section can be bent to assume the shape of a curved insulator by sliding the outer body over the insulator. Once the flexible section has assumed the required shape, the flexible portion can be made rigid by the application of hardening agents, or alternatively, can rely on the stiffness of the underlying curved insulator and/or inner body, if present.

Figure 13:
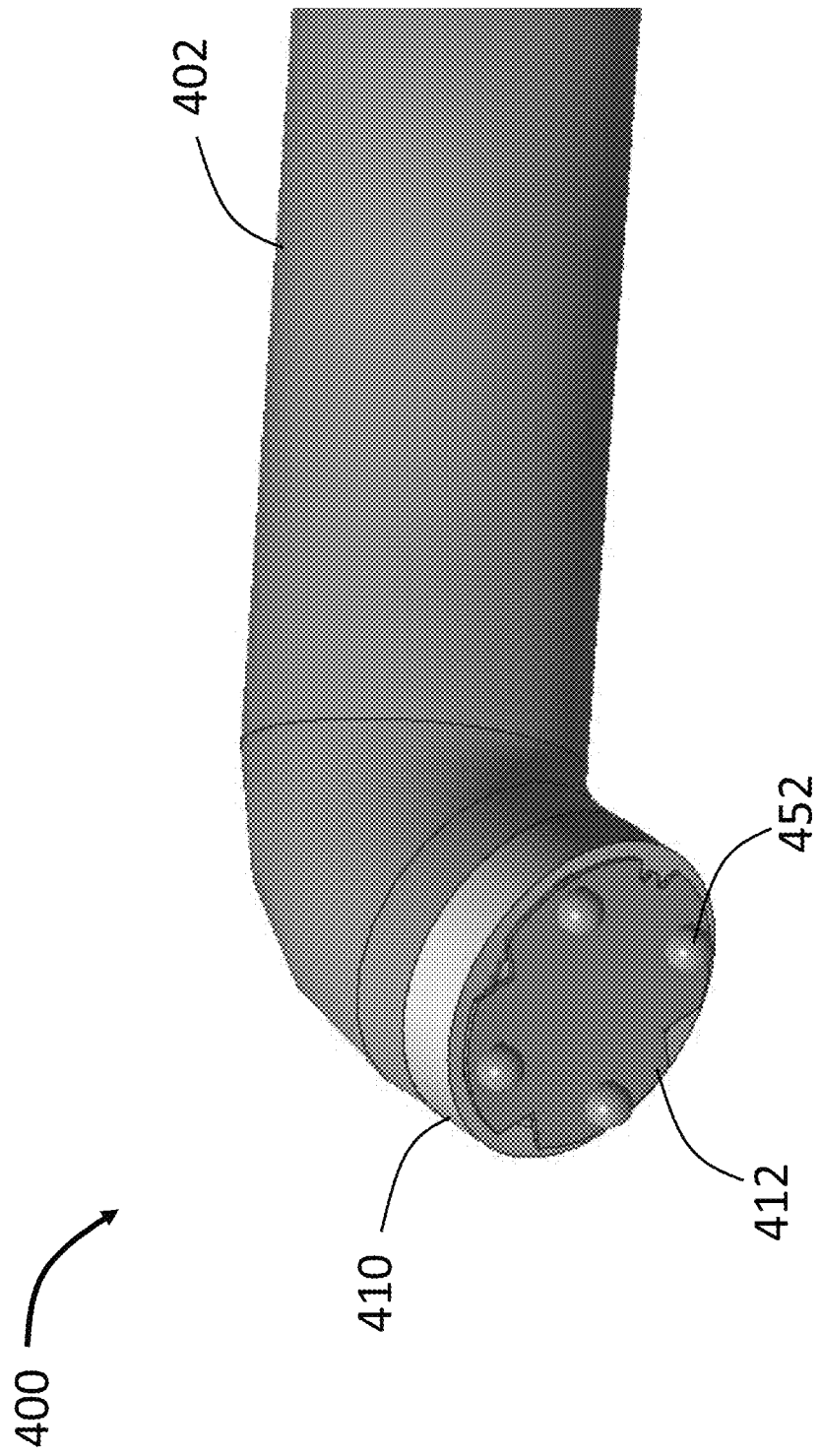
FIG. 13 is a side perspective view of an RF probe according to another embodiment of the present disclosure.
Figure 14:
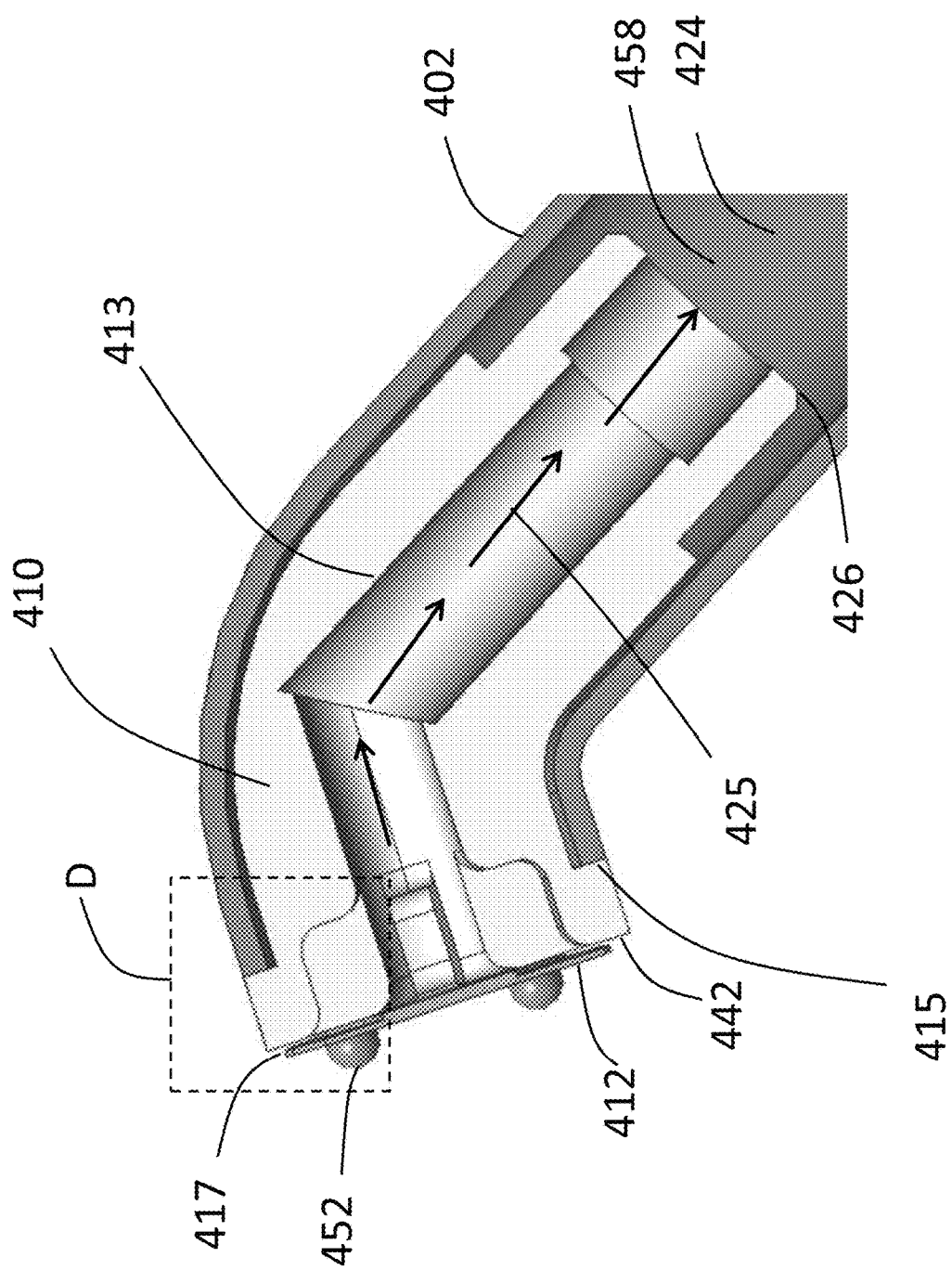
FIG. 14 is a side cross-sectional view of the RF probe of FIG. 13.
Figure 15:
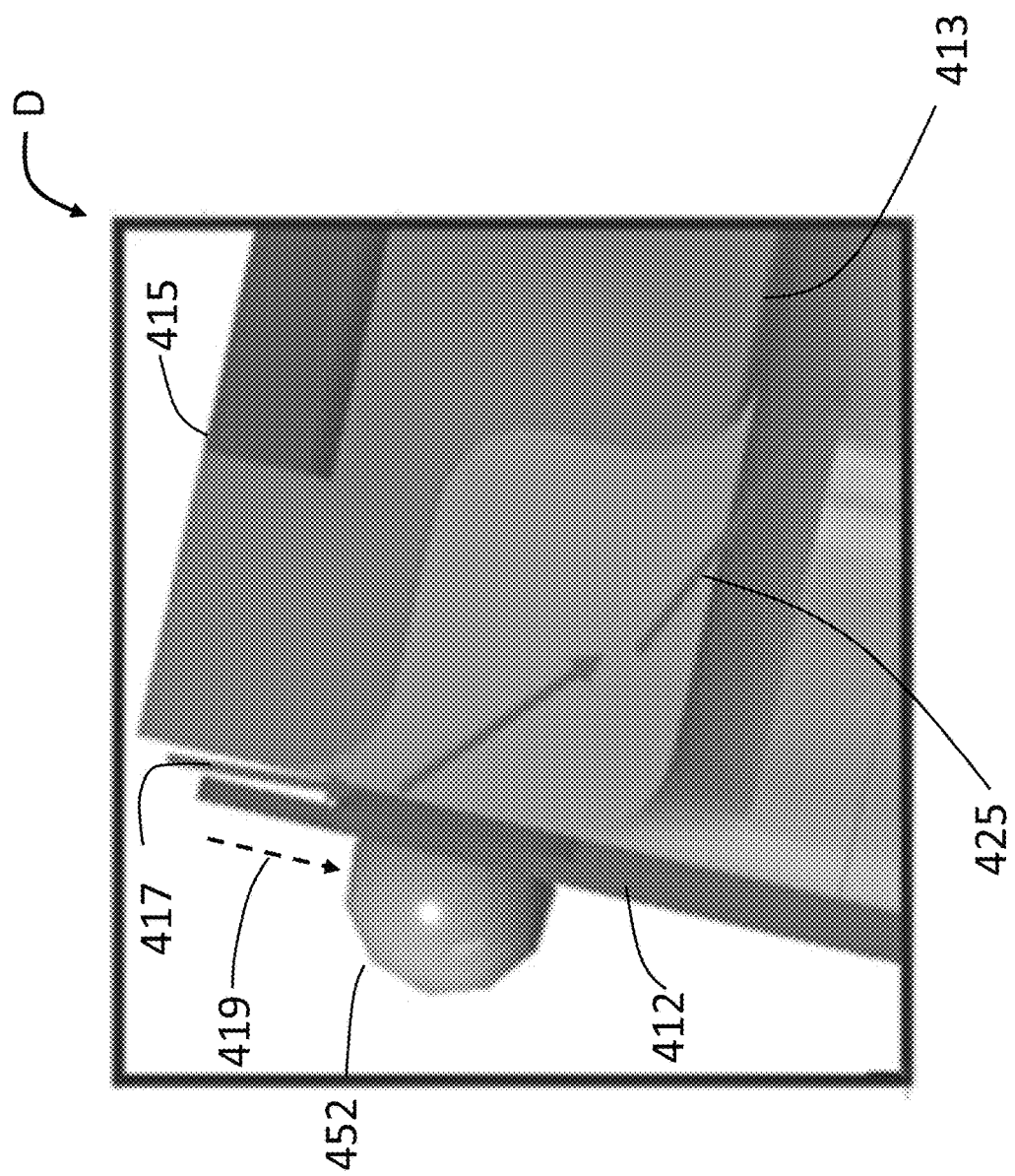
FIG. 15 is a detailed view of the RF probe of FIG. 14.

FIG. 13 shows an RF probe 400 according to another embodiment of the present disclosure. RF probe 400 is similar to RF probe 300, and therefore like elements are referred to with similar numerals within the 400-series of numbers. For example, RF probe 400 includes an outer body 402, an insulator 410 and a plate 412. However, plate 412 of RF probe 400 is attached to inner body 424 by ball wires 452. An internal channel 413 of insulator 410 forms a fluid flow channel 425 with an inlet 417. Inlet 417 formed between plate 412 and insulator 410 functions as the inlet for fluid flow channel 425 as best shown in FIGS. 14 and 15. Moving the inlet to the periphery as illustrated in this embodiment may be helpful to reduce the amount of erosion of plate 412 during active use of RF probe 400. This is due to the fact that metal will erode during active use, while insulator 410 (made of ceramic for example) will not erode. As a perimeter inlet 417 is only partially formed by plate 412, there will be less erosion than if the entire perimeter of inlet 417 were made of a metallic electrode. It should be appreciated that the inlet 417 is the gap formed between the proximal surface of plate 412 and distal surface of insulator 410. The greater the gap, the more fluid may pass into inlet 417. Moving the inlet to the periphery as illustrated in this embodiment may also helpful to provide improved flow characteristics during use. For example, this may also aid in directing fluid around the plate 412 while maintaining a stable fluid presence on the surface of the plate. Furthermore, the arrangement of plate 412 and insulator 410 to define inlet 417, ensures that plate erosion during RF probe use shown by direction arrow 419 does not impact the inlet size as best shown in FIG. 15. Thus, a constant flow through RF probe 400 can be maintained even as plate 412 erodes during probe use.

Figure 16:
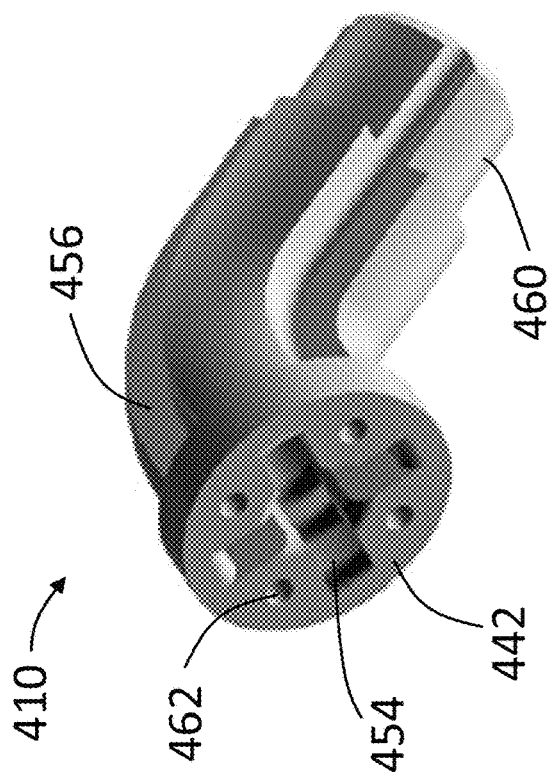
FIG. 16 is side perspective view of an insulator of the RF probe of FIG. 13.

Referring now to FIG. 16, there is shown insulator 410 of RF probe 400. Grooves 456 located on the sides of insulator 410 provide conduits for establishing electrical connectivity between ball wires 452 on plate 412 and inner body 424 through apertures 462. Fluid flow channel 425 has openings 454 on distal face 442 of insulator 410. A proximal end 460 of insulator 410 includes a setback configured to connect with inner body 424.

Figure 17:
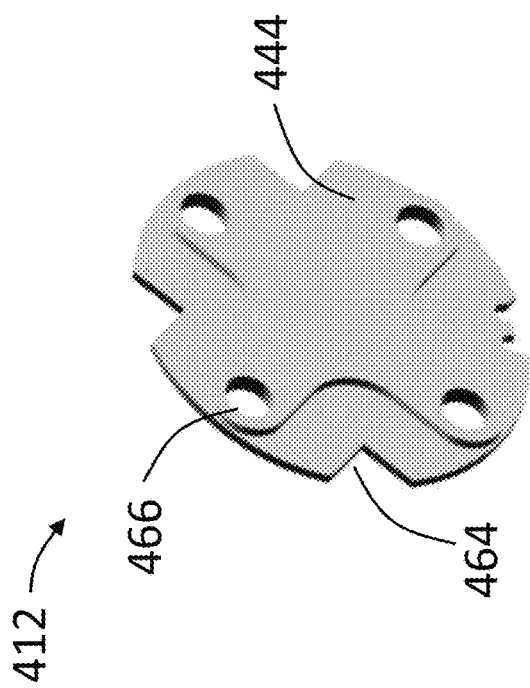
FIG. 17 is a side perspective view of a plate of the RF probe of FIG. 13.

FIG. 17 shows plate 412 of RF probe 400. Plate 412 includes apertures 416 corresponding to apertures 462 to connect ball wires 452 with inner body 424. Distal surface 444 includes cutouts 464 to channel fluid inlet to fluid flow channel 425.

Referring now to FIG. 18, there is shown an RF probe 500 according to another embodiment of the present disclosure. RF probe 500 is similar to RF probe 400, and therefore like elements are referred to with similar numerals within the 500-series of numbers. For example, RF probe 500 includes an outer body 502, an insulator 510 and a plate 512. However, RF probe 500 includes a central aperture 550 through plate 512 thereby having a distal inlet for a fluid flow channel 525 (not shown).

Figure 20:
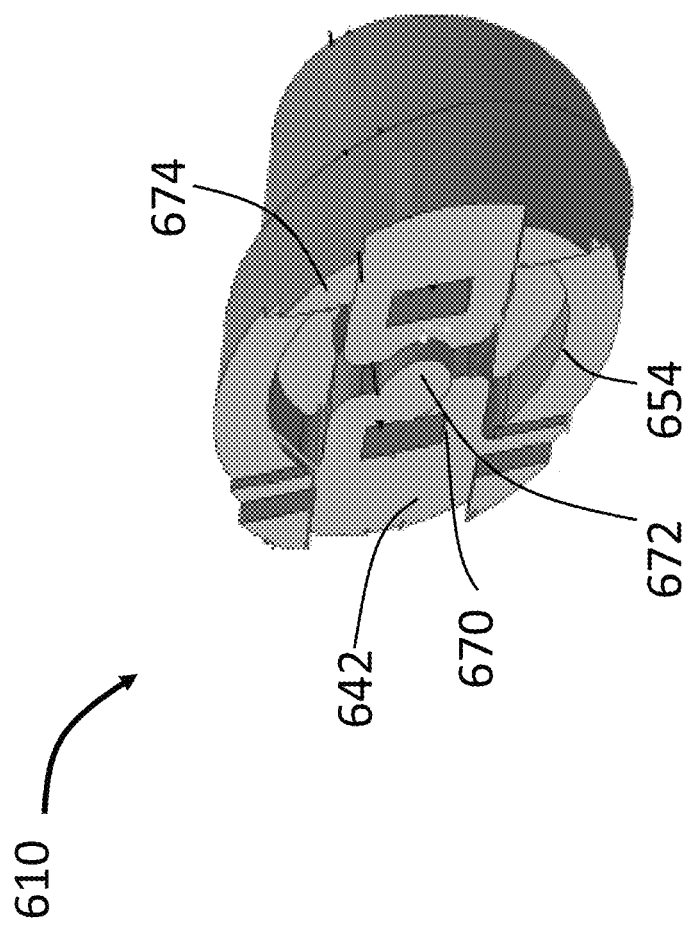
FIG. 20 is a side perspective view of an insulator of an RF probe according to another embodiment of the present disclosure.

FIG. 19 show an RF probe 600 according to another embodiment of the present disclosure. RF probe 600 is similar to RF probe 100, and therefore like elements are referred to with similar numerals within the 600 series. For example, RF probe 600 includes an outer body 602, an insulator 610 and a plate 612. However, insulator 610 of RF probe 600 includes raised offsets 674, 672 to prevent direct tissue contact with plate 612 as best shown in FIG. 20. Plate 612 includes serrations 668 around its perimeter to maximize current density at the periphery.

In addition, insulator 610 contains two windows 670 to allow prongs 638 (not shown) to extend therethrough. Windows 670 are used to adhere plate 612 to inner body 624 and provide protection to prongs 638 from electrode erosion during probe use. Enclosing prongs 638 with the ceramic material of insulator 610 reduces or prevents erosion of the prongs and the plate area adjacent to windows 670. The ceramic material can be manufactured from alumina which is impervious to erosion. Thus, it can be used to block flow and avoid or reduce erosion of the plate and inner body in specific areas. Strategic placement of insulator material in conjunction with the plate and inner body increases probe lifetime and/or reduces electrode mass. This may allow RF probe 600 to more efficiently generate plasma and improves performance. In addition, the concept could also be used to minimize wear at and/or around the suction port on the electrode to prevent the port from becoming too large (due to erosion during use) which could lead to excessive clogging.

Figure 22:
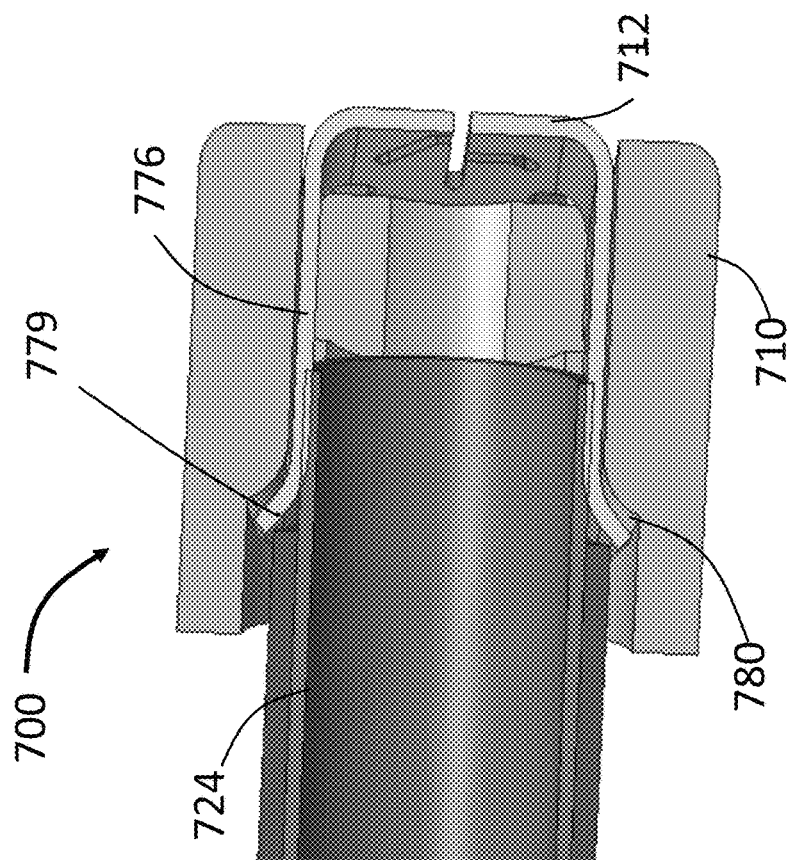
FIG. 22 is a side cross-sectional view of the RF probe of FIG. 21.
Figure 21:
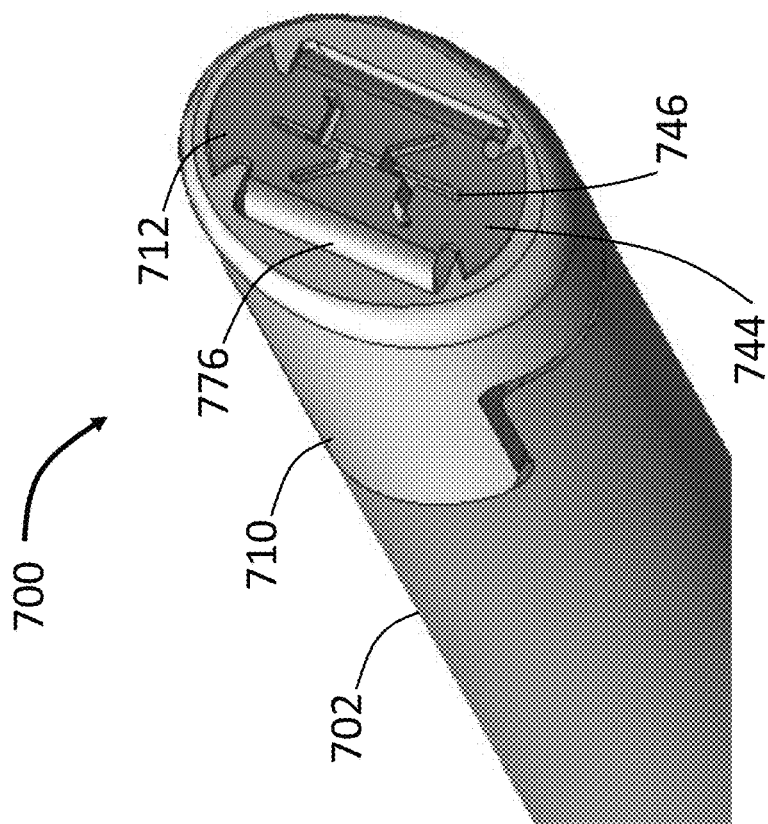
FIG. 21 is a side perspective view of an RF probe according to another embodiment of the present disclosure.

Referring now to FIG. 21, there is shown an RF probe 700 according to another embodiment of the present disclosure. RF probe 700 is similar to RF probe 100, and therefore like elements are referred to with similar numerals within the 700-series of numbers. For example, RF probe 700 includes an outer body 702, an insulator 710 and a plate 712. However, plate 712 of RF probe 700 is press-fitted to insulator 710 to be mechanically retained by the insulator. As best seen in FIG. 22, plate 712 includes flexible arms 776 with proximal ends 724 configured to engage with retaining features 780 of insulator 710. Plate 712 can be readily coupled to RF probe 700 by pushing plate 712 through the insulator until proximal ends 779 of flexible arms 776 snap fit into retaining features 780 of insulator 710. Contact between proximal ends 779 and inner body 724 establishes electrical conductivity between the plate and the inner body. Hence, no fabrication process such as welding is required to attach plate 712 to RF probe 700.

Figure 23:
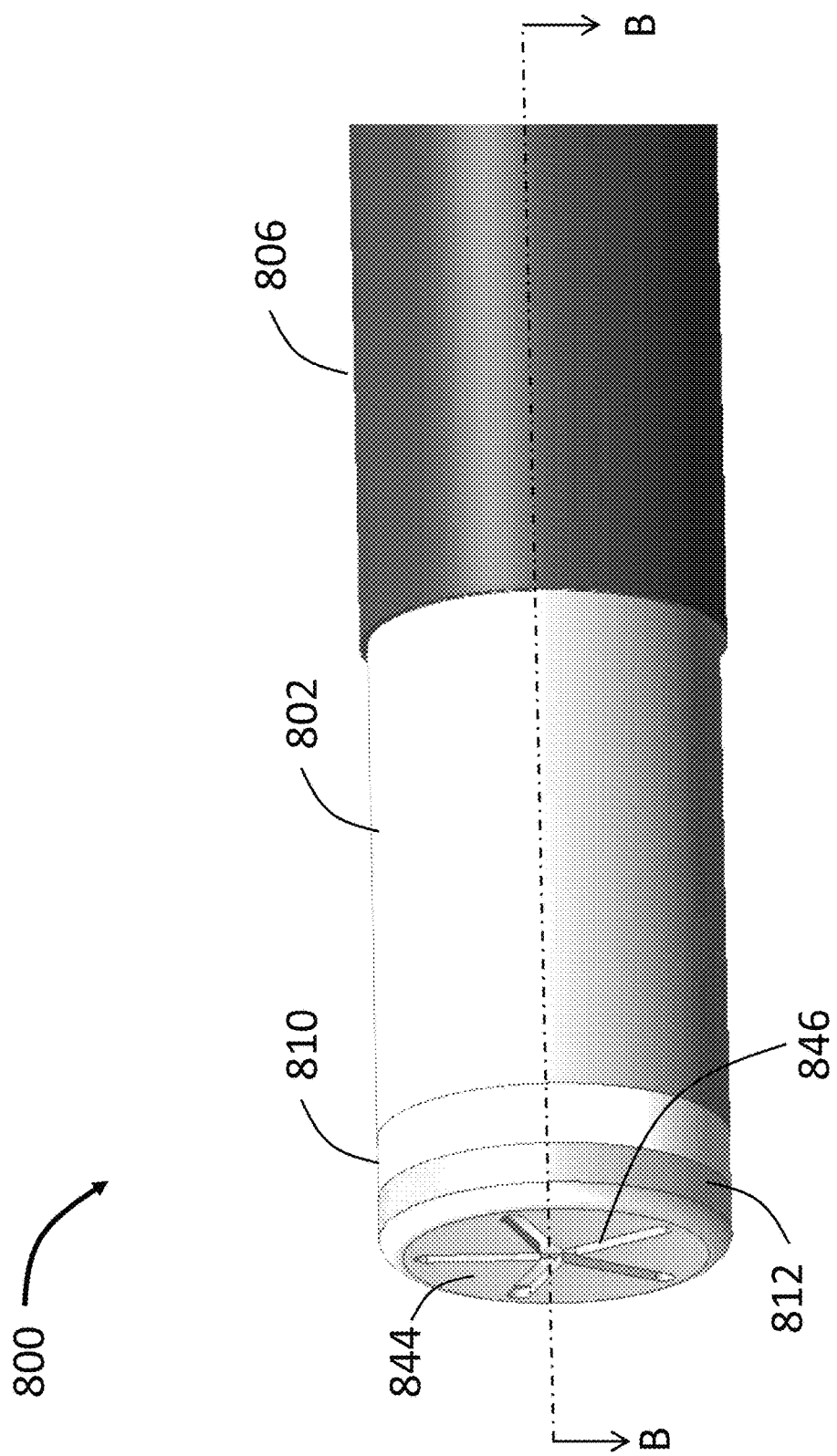
FIG. 23 is a side perspective view of an RF probe according to another embodiment of the present disclosure.
Figure 24:
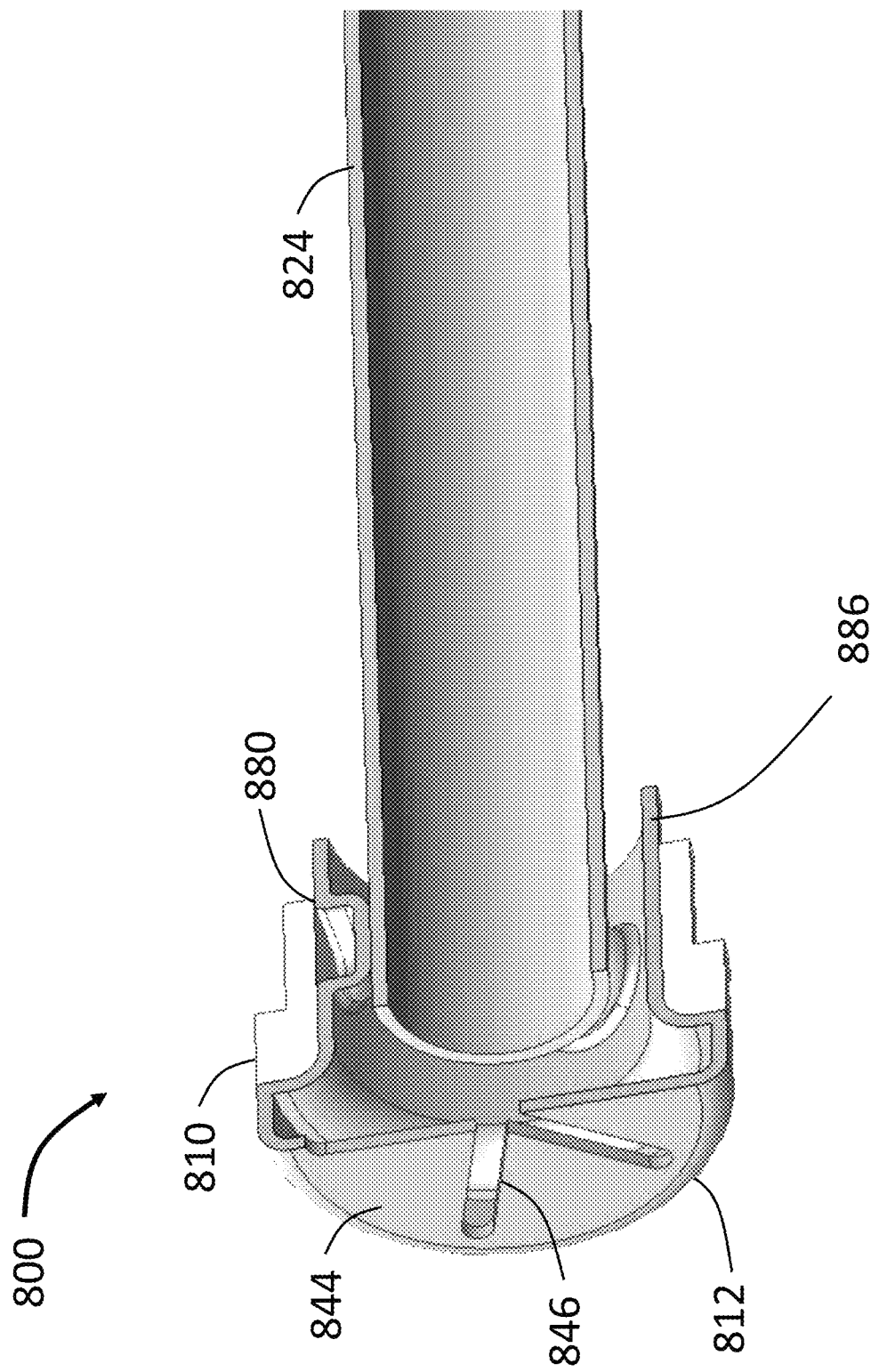
FIG. 24 is a side cross-sectional view along line B-B of the RF probe of FIG. 23.
Figure 26:
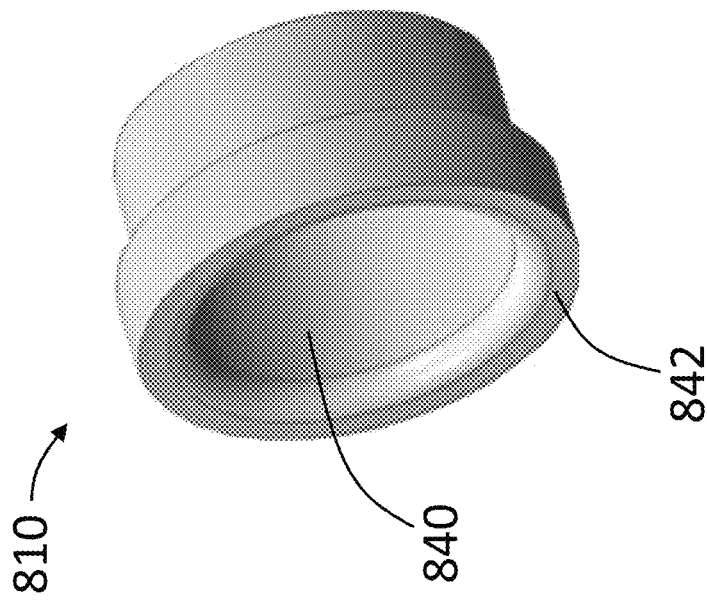
FIG. 26 is a side perspective view of an insulator of the RF probe of FIG. 23.
Figure 25:
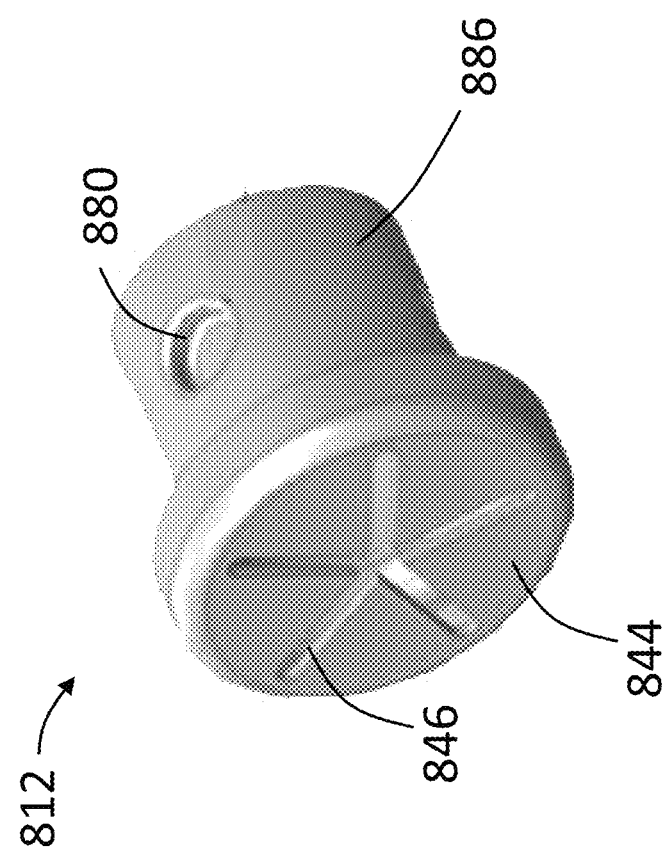
FIG. 25 is a side perspective view of a plate of the RF probe of FIG. 23.

FIG. 23 shows an RF probe 800 according to another embodiment of the present disclosure. RF probe 800 is similar to RF probe 700, and therefore like elements are referred to with similar numerals within the 800-series of numbers. For example, RF probe 800 includes an outer body 802, an insulator 810 and a plate 812. However, plate 812 includes tabs 880 as retaining features which engage with inner body 824 to secure the plate to the inner body as best shown in FIG. 24. Plate 812 shown in FIG. 25 is inserted through insulator 810 shown in FIG. 26. Insulator 810 pushes flexible surface 886 towards inner body 824 to force tabs 880 to form an interference fit with the inner body and secure plate 812 to RF probe 800. Similar to RF probe 700, attaching plate 812 to RF probe 800 requires no additional fabrication process.

Figure 27:
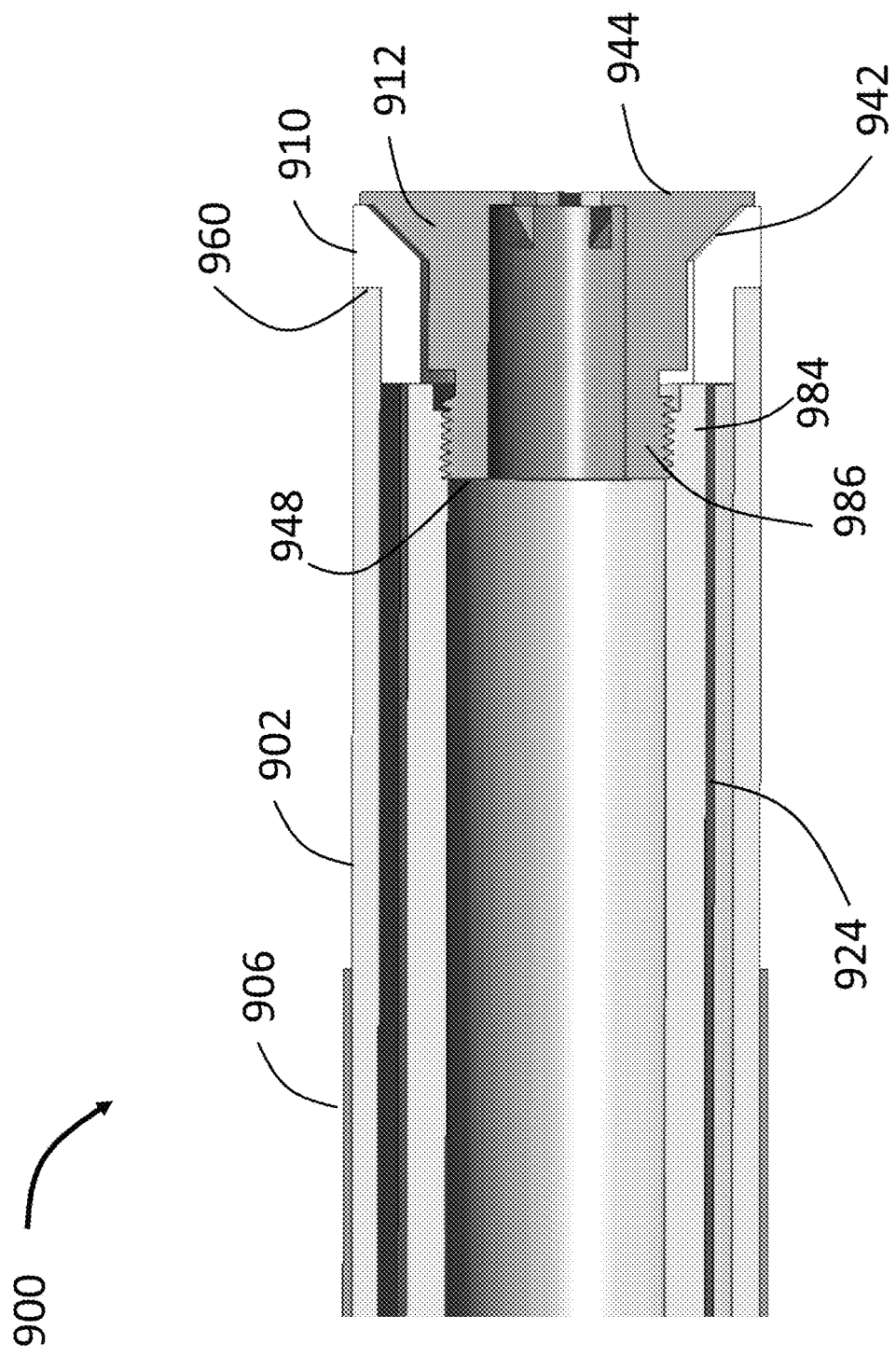
FIG. 27 is a side cross-sectional view of an RF probe according to another embodiment of the present disclosure.
Figure 29:
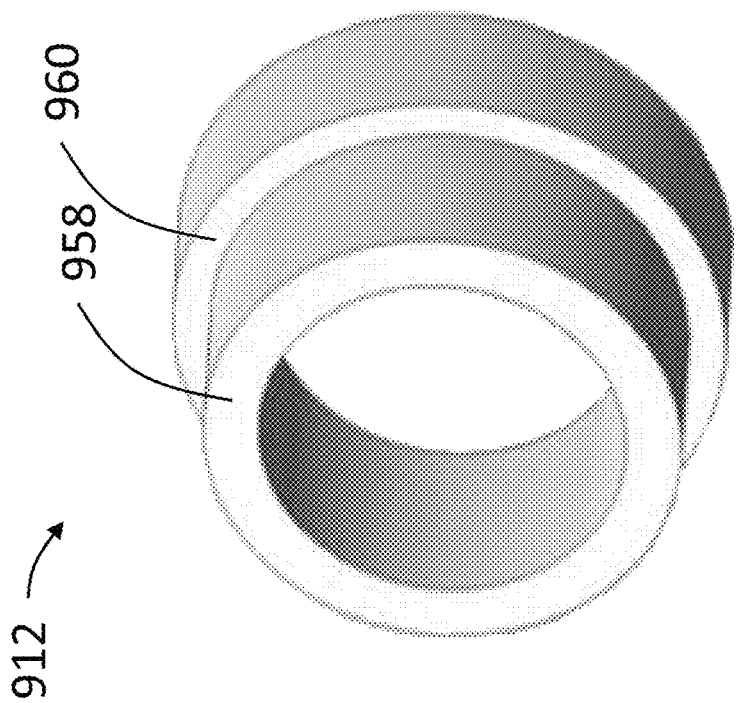
FIG. 29 is a side perspective view of an insulator of the RF probe of FIG. 27.
Figure 28:
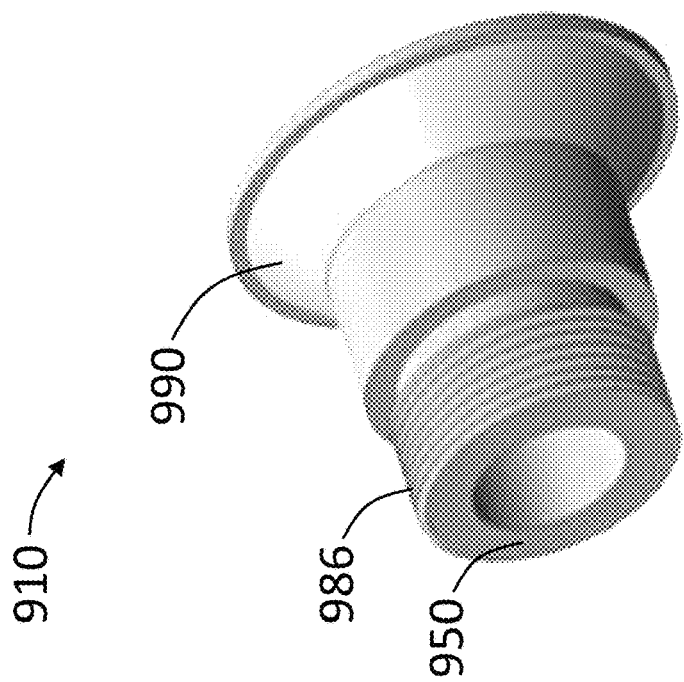
FIG. 28 is side perspective view of a plate of the RF probe of FIG. 27.

FIG. 27 shows an RF probe 900 according to another embodiment of the present disclosure. RF probe 900 is similar to RF probe 800, and therefore like elements are referred to with similar numerals within the 900-series of numbers. For example, RF probe 900 includes an outer body 902, an insulator 910 and a plate 912. However, plate 912 includes an externally threaded portion 986 which threadingly engages with an internally threaded portion of inner body 924. As shown in FIGS. 28 and 29, plate 912 is configured to be received through insulator 910 to allow a chamfer portion 990 to contact the distal surface of insulator

910. Plate 910 can be threaded onto inner body 924 to secure the plate to RF probe 900 and to establish electrical conductivity between plate 912 and inner body 924.

Figure 30:
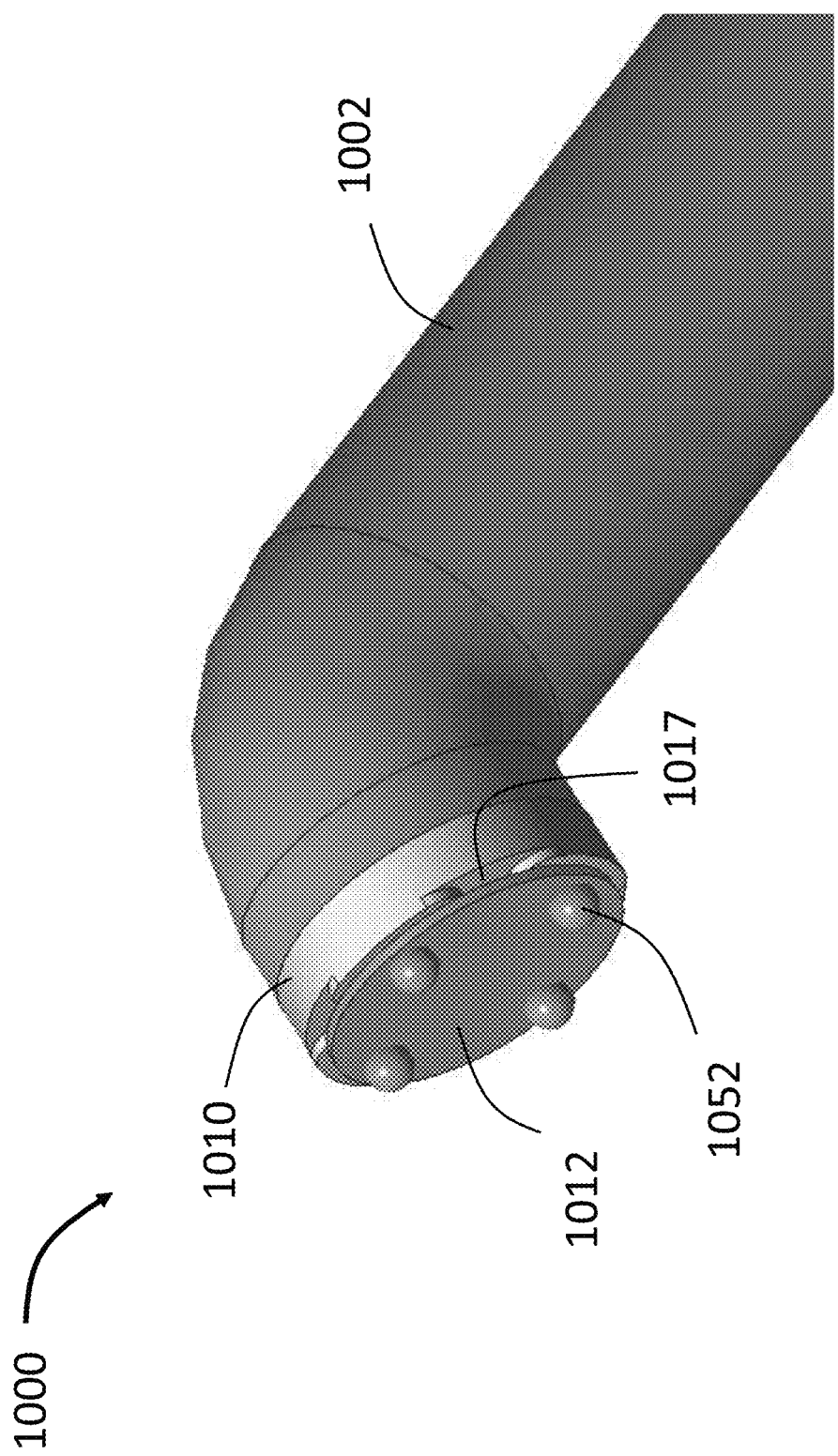
FIG. 30 is a side perspective view of an RF probe according to another embodiment of the present disclosure.
Figure 32:
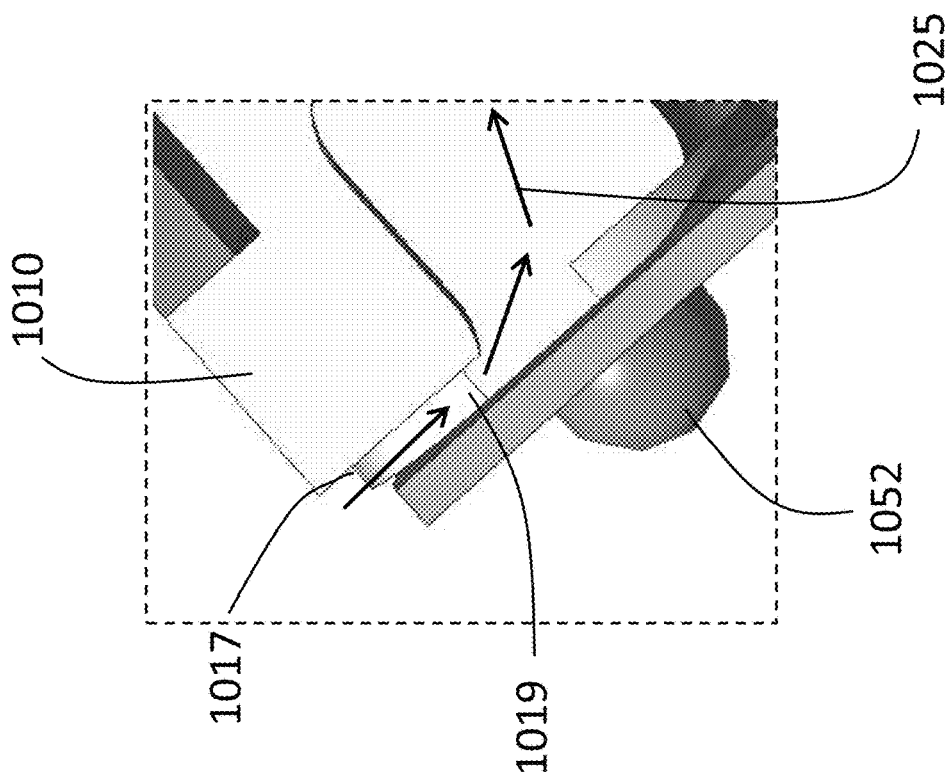
FIG. 32 is a detailed view of the RF probe of FIG. 30.
Figure 31:
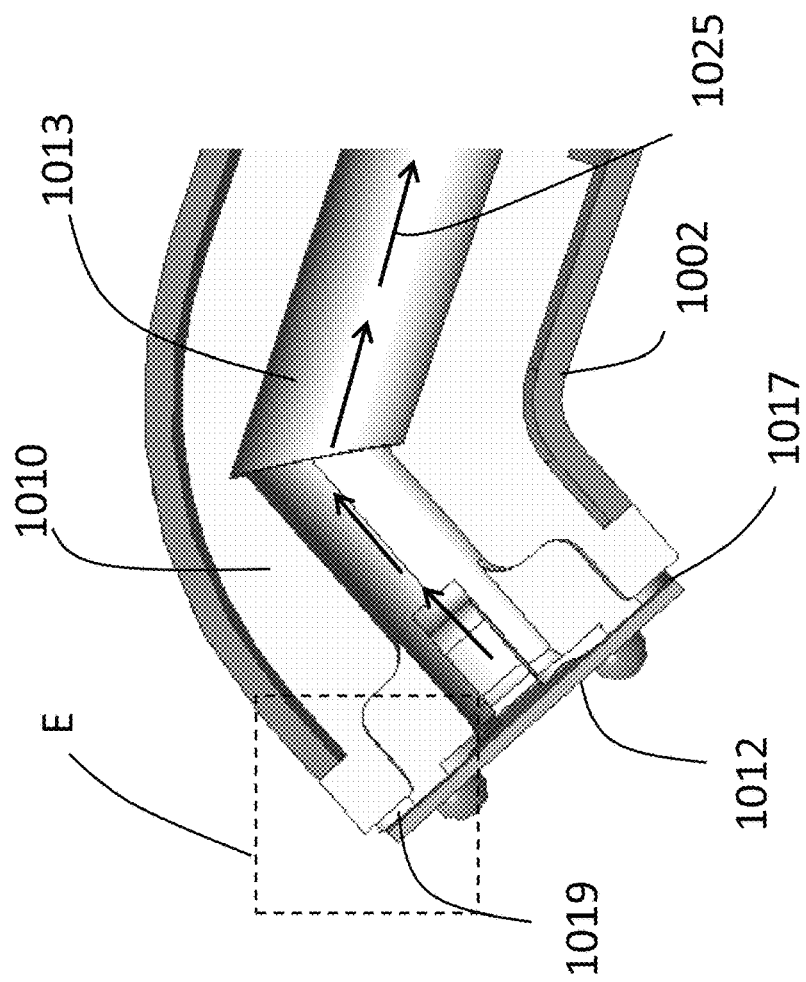
FIG. 31 is a side cross-section view of the RF probe of FIG. 30.
Figure 34:
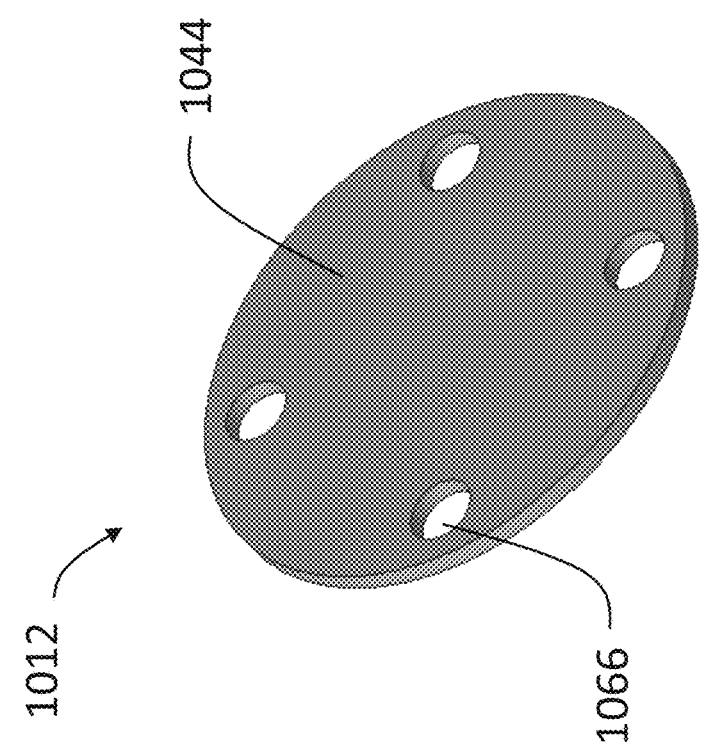
FIG. 34 is a side perspective view of a plate of the RF probe of FIG. 30.
Figure 33:
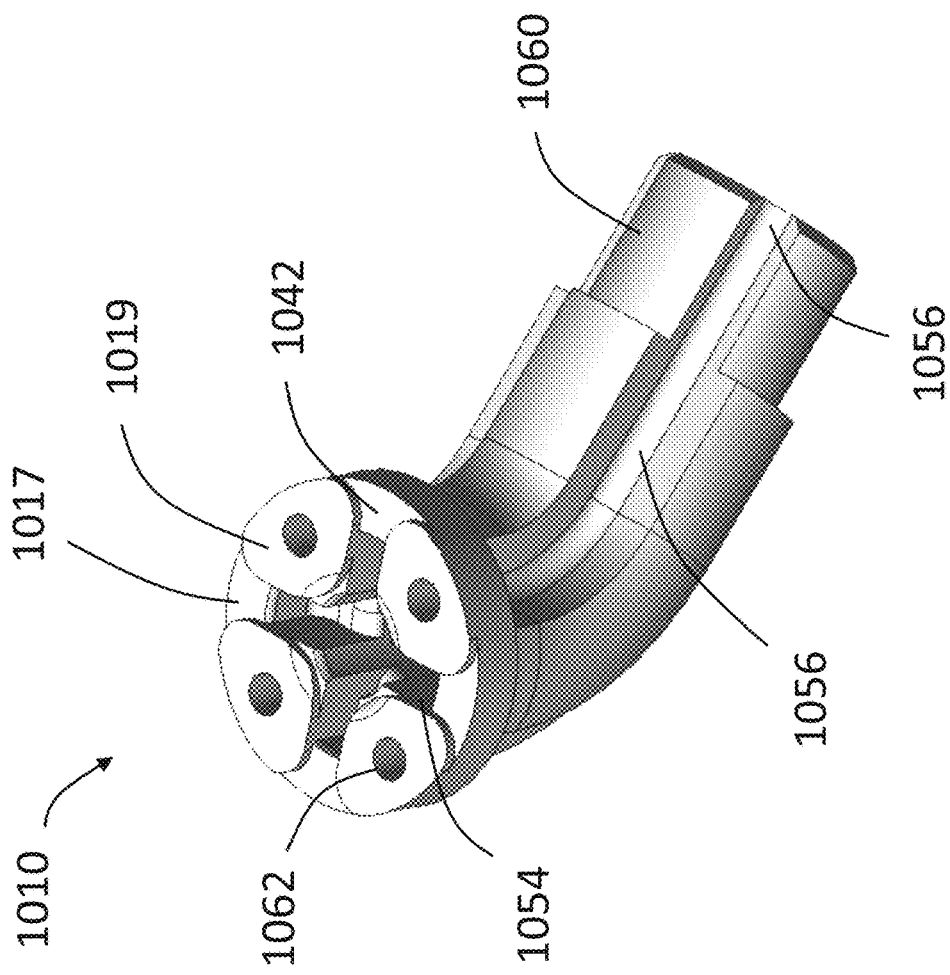
FIG. 33 is a side perspective view of an insulator of the RF probe of FIG. 30.

Referring now to FIG. 30, there is shown an RF probe 1000 according to another embodiment of the present disclosure. RF probe 1000 is similar to RF probe 400, and therefore like elements are referred to with similar numerals within the 1000-series of numbers. For example, RF probe 1000 includes an outer body 1002, an insulator 1010 and a plate 1012. However, insulator 1010 of RF probe 1000 includes pads 1019 raised above distal surface 1042 as best shown in FIG. 33. The raised pads define inlet opening 1017 for fluid flow path 1025 as shown in FIGS. 31 and 32. A central opening 1054 of insulator 1010 in conjunction with inlet opening 1017 channel fluid flow into RF probe 1000 as depicted in FIG. 33. Therefore, fluid inlet for fluid flow path 1025 can be configured almost exclusively by the shape of the insulator requiring a simplified plate 1012 structure as shown in FIG. 34.

Figure 35:
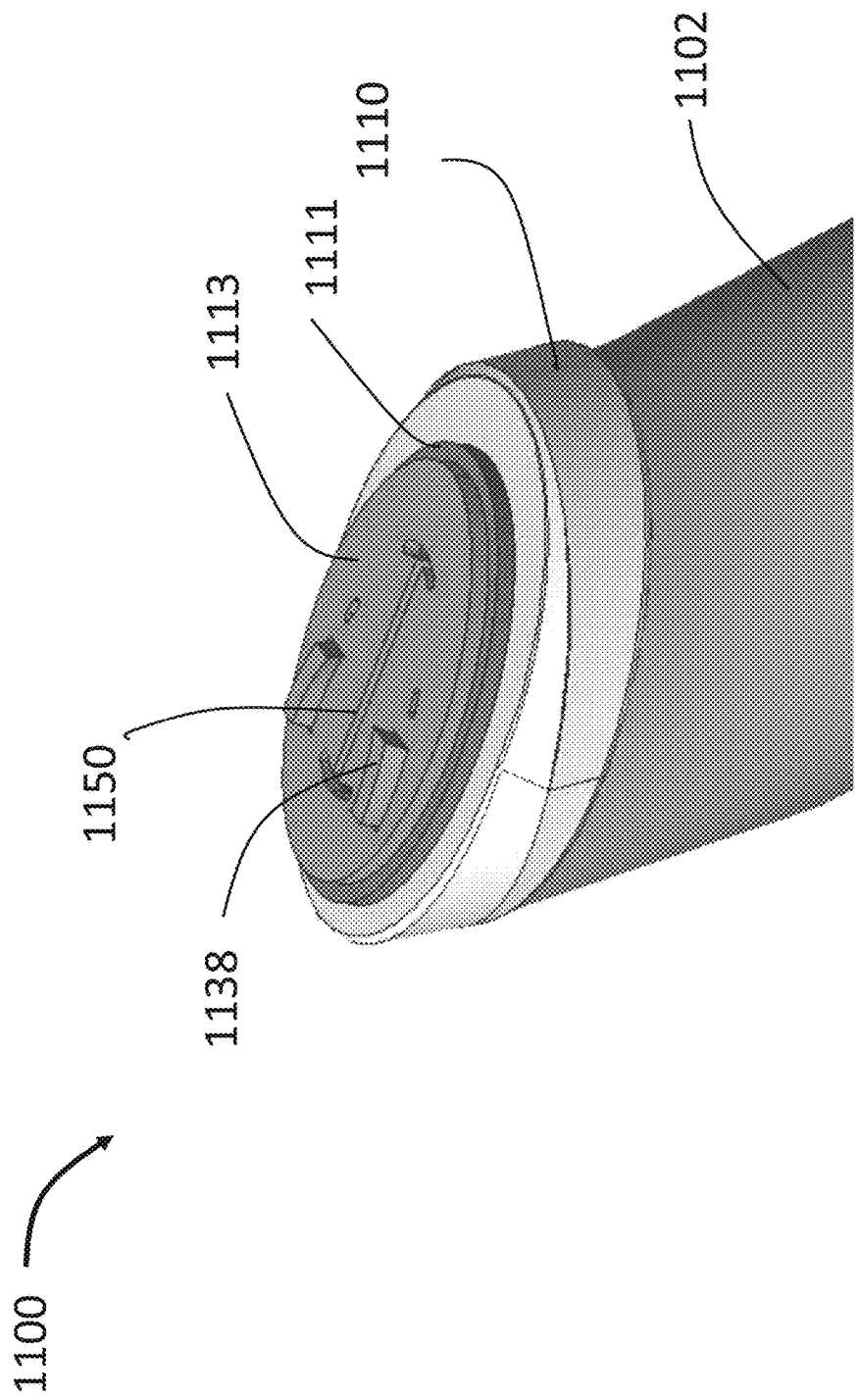
FIG. 35 is a side perspective view of an RF probe according to another embodiment of the present disclosure.
Figure 36:
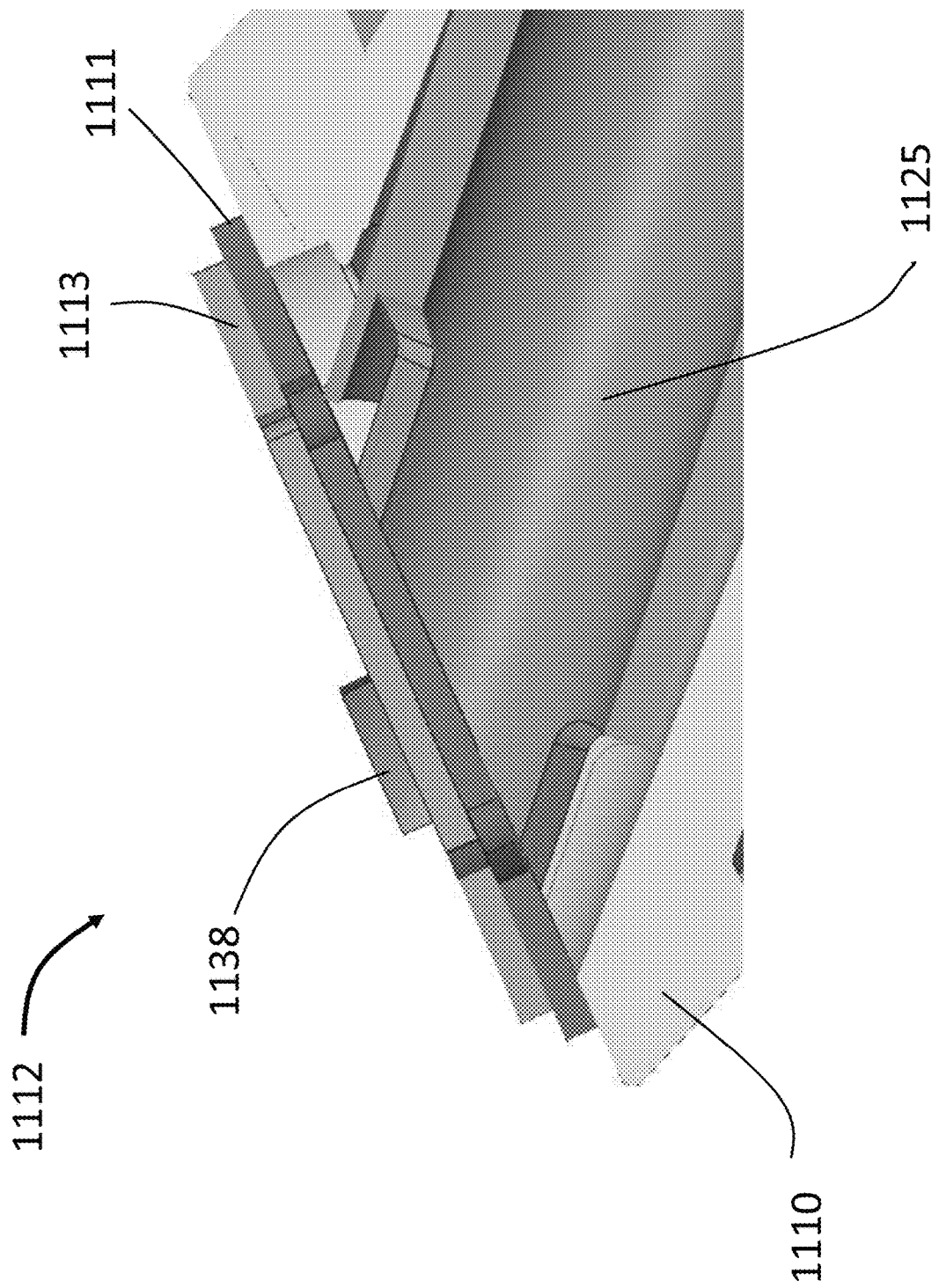
FIG. 36 is a side cross-section view of the RF probe of FIG. 35.

FIGS. 35 and 36 show an RF probe 1100 according to another embodiment of the present disclosure. RF probe 1100 is similar to RF probe 100, and therefore like elements are referred to with similar numerals within the 1100-series of numbers. For example, RF probe 1100 includes an outer body 1102, an insulator 1110 and a plate 1112. However, plate 1112 includes a first plate 1111 and a second plate 1113 place over the first plate. First and second plates can be made of different materials to provide improved functionality of plate 1112 over a plate made of a single material. For example, first plate 1111 can be made of tungsten and second plate 1113 can be made of stainless steel in RF probe 1100. While tungsten is more erosion-resistant than stainless steel, fabricating complex shapes with tungsten is more difficult than stainless steel. Therefore, this embodiment allows for the tungsten layer to be formed as a simple plate which can improve erosion resistance while maintaining a relatively simplified manufacturing process with ready attachment of the inner body to the stainless plate 1112. Attaching a tungsten plate to a stainless steel inner body may not provide the required bonding between these different materials in comparison to attaching the stainless steel plate to the stainless steel inner body. Further, the stainless steel plate 1112 can be shaped with more complex features to accomplish other functions, if desired. Furthermore, the stainless steel prongs 1138 of inner body 1124 are attached by welding or other means to the stainless steel second plate 1112 requiring no fabrication of tungsten first plate 1111 (e.g., no need for direct welding of tungsten plate to steel prongs) for assembly of RF probe 1100. Thus, the welding of the stainless steel prongs 1138 to the stainless steel plate 1113 sandwiches the tungsten plate 1111 in between the plate 1113 and the insulator 1110. Alternatively, additional welding, brazing, adhesive, or the like may be used to further secure the tungsten plate 1111 in position.

Further, as best shown in FIG. 36, tungsten first plate 1111 may have a larger footprint than stainless steel second plate 1113 with the edge of first plate 1111 extending beyond the edge of second plate 1113. This may allow the more erosion-resistant tungsten plate 1111 to slow down the erosion of the overall plate 1112 during RF probe 1100 use. While plate 1112 described here includes a tungsten first plate 1111 and a stainless steel plate 1113, other embodiments can include plates made of various other materials configured for specific applications of the RF probes. In one embodiment, more than 50% of the exterior perimeter edge of first plate 1111 can extend beyond the exterior perimeter edge of second plate 1113. In another embodiment, more than 75% of the exterior perimeter edge of first plate 1111 can extend beyond the exterior perimeter edge of second plate 1113. In yet another embodiment, substantially all of exterior perimeter edge of first plate 1111 can extend beyond the exterior perimeter edge of second plate 1113.

Figure 37:
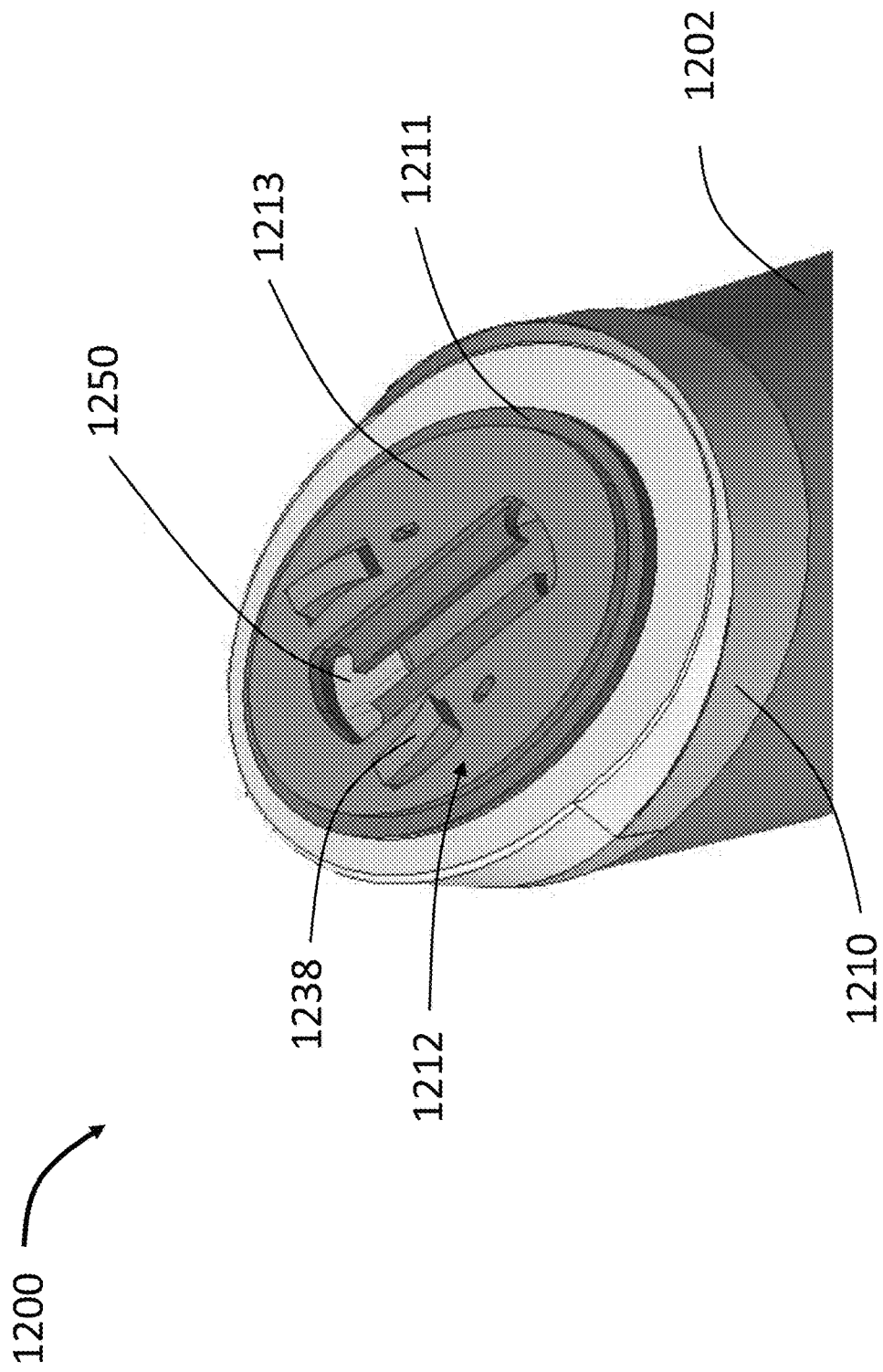
FIG. 37 is a side perspective view of an RF probe according to another embodiment of the present disclosure.

FIG. 37 shows an RF probe 1200 according to another embodiment of the present disclosure. RF probe 1200 is similar to RF probe 1100, and therefore like elements are referred to with similar numerals within the 1200-series of numbers. For example, RF probe 1200 includes an outer body 1202, an insulator 1210 and a plate 1212 with a first plate 1211 and a second plate 1213. However, second plate 1213 includes a larger central aperture 1250 in this embodiment, relative to the I-shaped central aperture (similar to central aperture 150 of FIG. 7) of the first plate 1211 to reduce plate mass while simultaneously providing for proper mechanical and electrical connectivity between the inner body and the plate. Furthermore, the central aperture in RF probe 1200 is defined by tungsten first plate 1211 thereby limiting contact of inlet fluid with only the tungsten first plate to decrease erosion of plate 1212. Further, the interior edge of central aperture 1250 of tungsten first plate 1211 can extend further inboard to the interior edge of I-shaped central aperture 1250. In one embodiment, more than 50% of the interior edge of central aperture 1250 of tungsten first plate 1211 can extend further inboard to the interior edge of the I-shaped central aperture. In another embodiment, substantially all of the interior edge of central aperture 1250 of tungsten first plate 1211 can extend further inboard to the interior edge of the I-shaped central aperture. Similar to the exterior perimeter edges, this may allow the more erosion-resistant tungsten plate 1111 to slow down the erosion of the overall plate 1112 during RF probe 1100 use.

Figure 38:
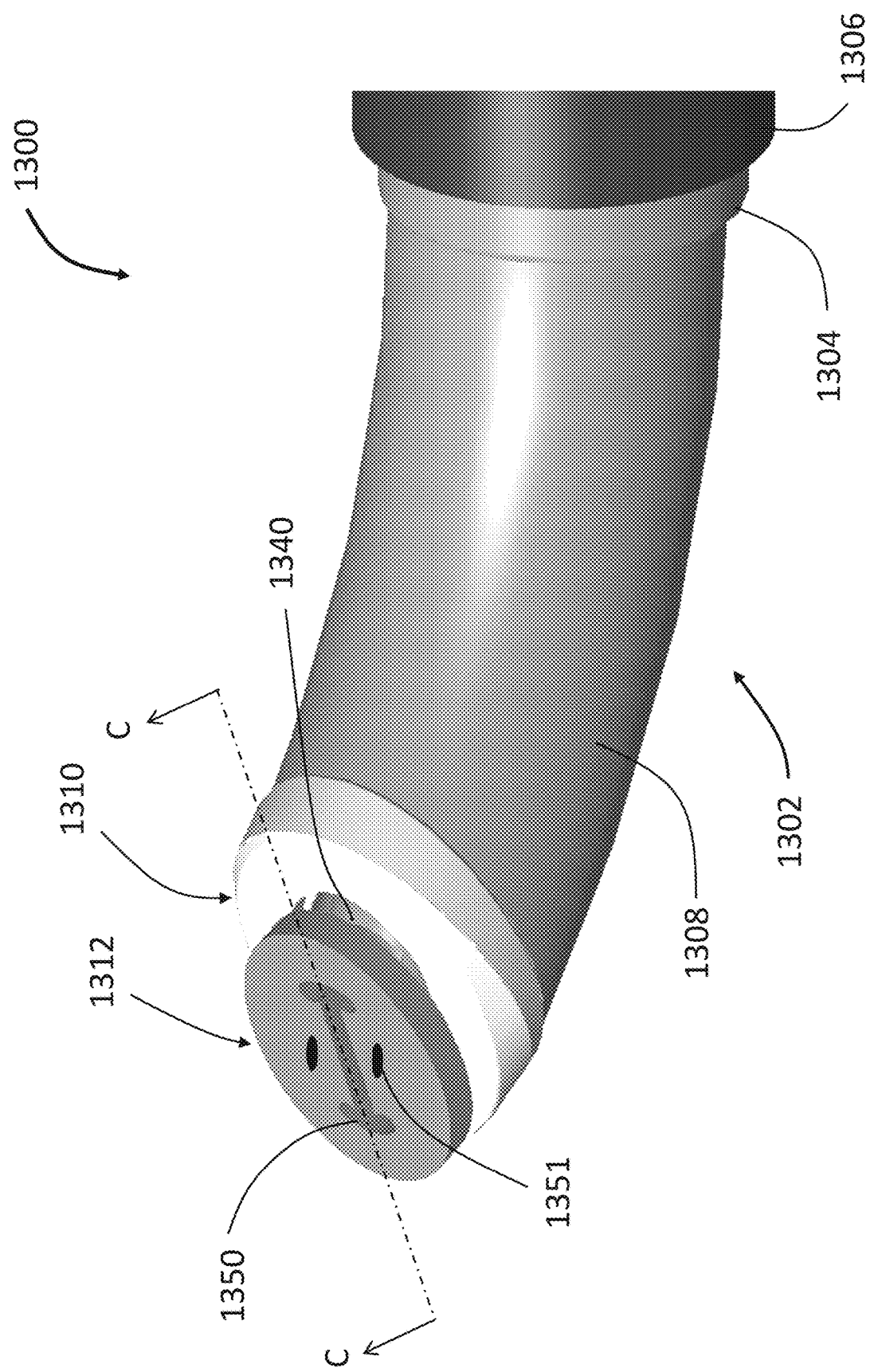
FIG. 38 is side perspective view of an RF probe according to another embodiment of the present disclosure.
Figure 39:
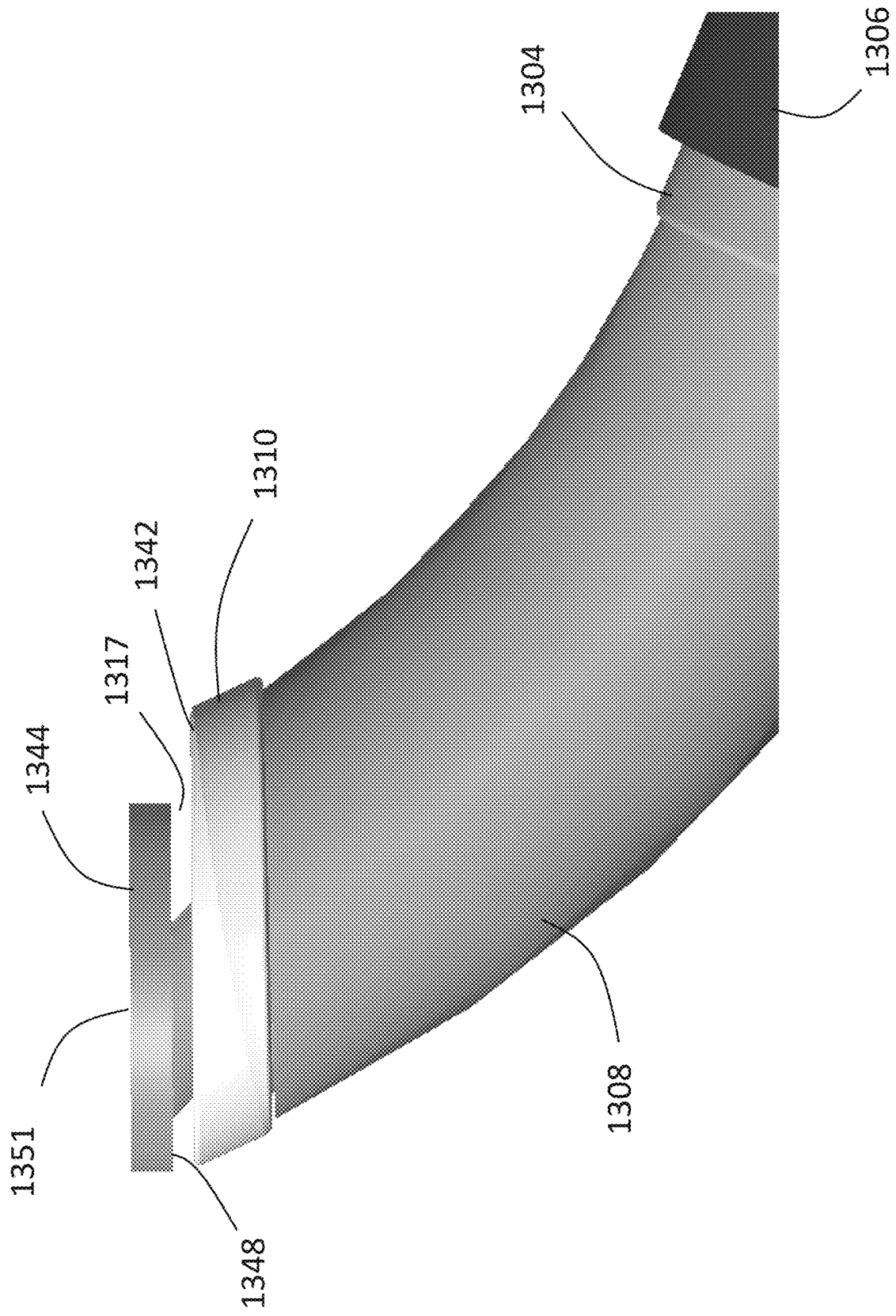
FIG. 39 is a side view of the RF probe of FIG. 38.

FIGS. 38 and 39 show an RF probe 1300 according to another embodiment of the present disclosure. RF probe 1300 is similar to RF probe 100, and therefore like elements are referred to with similar numerals within the 1300-series of numbers. For example, RF probe 1300 includes an outer body 1302, an insulator 1310 and a plate 1312. However, in this embodiment, plate 1312 does not contact insulator 1310, and as such, RF probe 1300 includes an aperture or side inlet 1317 in addition to the central aperture 1350 to remove ablated tissue, working fluid, gas bubbles and/or debris from the surgical site, any of which may be formed during use of RF probe 1300. Side inlet 1317 is formed by a gap having a dimension L1 between proximal surface 1348 of plate 1312 and distal face 1342 of insulator 1310 as best shown in the cross-section of FIG. 40. Proximal surface 1348 of plate 1312 does not contact distal surface 1342 of insulator 1310 in this embodiment, but instead, the plate 1312 is held in a spaced relation relative to insulator 1310 by the at least one prong 1338 of the inner body 1324, as discussed in depth above. As such, the electrical connection between inner body 1324 and plate 1312 is maintained, but the plate 1312 is spaced apart from the insulator to provide for the additional flow path through side inlet 1317. As best shown in FIGS. 38 and 39, this embodiment illustrates one embodiment of a completed RF probe 1300, whereby the projections are already welded to hole the plate in place. As such, as illustrated, the at least one prong 1338 do not extend through weld slots 1351 and past the plate surface 1312, but instead the prongs are melted during welding to a position generally flush with distal surface 1344 in this embodiment. Indeed, such a structure would be the result of welding any of the other embodiments discussed herein where a projection or prong extends through a passage in a plate, in that upon welding the projection or prong would be subjected to at least partial melting such that the resulting prong or projection sits generally flush with the distal surface of the plate (or outer plate if multiple plates). By "generally flush," the prong or projection, and weld material, would be flush with the distal surface of the plate (or outer plate if multiple plates) or would be partially extending distally past the distal surface or extending almost to but not to the distal surface, and thus would remain still within the passage of the plate (or passages through multiple plates).

Gap dimension L1 can be varied to increase the side inlet 1317 size. For example, increasing the size of L1 will result in a larger side inlet 1317 which may lead to greater suction rates from the surgical site. Side inlet 1317 provides a secondary suction inlet in addition to aperture 1350 and thereby increases fluid removal from the surgical site and also provides an alternate means for suction flow if the central aperture 1340 is blocked during the ablation procedure. Aperture 1350 and side inlet 1317 are sized to limit intake of certain sizes of ablated tissue and debris particles to prevent blockage of fluid flow path 1325. At least one opening dimension of aperture 1350 and side inlet 1317 is sized to be substantially less than a diameter of fluid flow path 1325 to prevent ablated tissue and debris particles larger than the fluid flow path 1325 from entering through the suction inlets. For example, gap dimension L1 is sized to be substantially less than the diameter of fluid flow path 1325. It should be noted that the total suction intake area— i.e., the addition of aperture 1350 and side inlet 1317, can as a combined intake area be the same, greater or less than the intake area (i.e., cross-sectional diameter) of the fluid flow path 1325. It should also be noted that aperture 1350 can have an opening area which is the same, greater or less than the opening area of side inlet 1317. In one embodiment, opening area of aperture 1350 can be greater than opening area of side inlet 1317.

Figure 40:
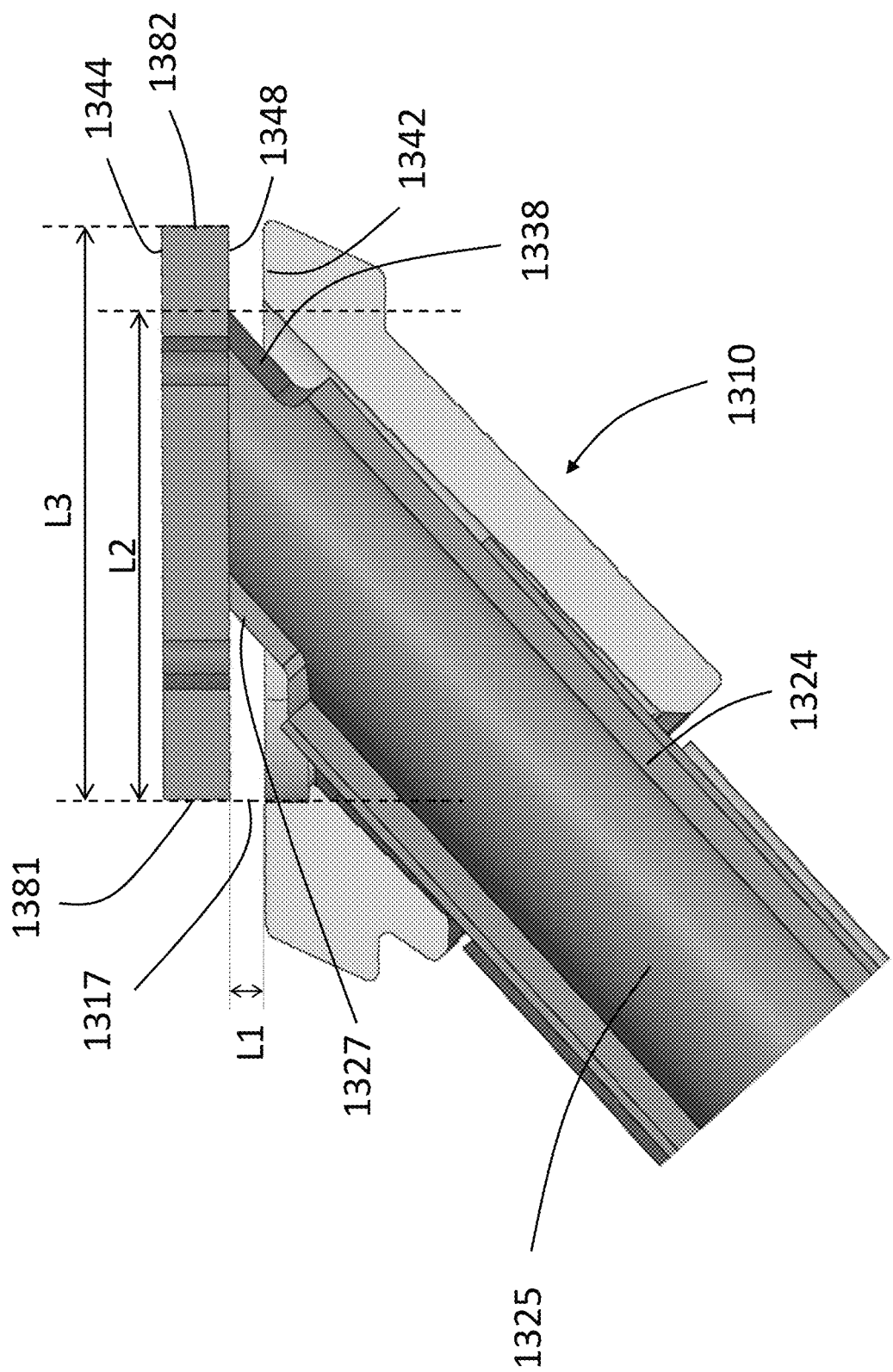
FIG. 40 is a side cross-sectional view of the RF probe of FIG. 38 along line C-C including inner body prongs according to one embodiment.

A second dimension L2 depicts a major diameter of insulator aperture 1340, and a third dimension L3 depicts a major diameter of plate 1312 as best shown in FIG. 40. Plate 1312 can be sized and positioned to align with insulator aperture 1340, or can be positioned offset to the insulator aperture 1340 a desired amount. As shown in FIG. 40, a first end 1381 aligns with insulator aperture 1340, whereas a second end 1382 extends laterally relative to insulator aperture 1340. Various sizes and positioning of plate 1312 and insulator aperture 1340 can be provided to control the suction functionality of RF probe 1300. For example, a plate extending over an insulator aperture will create more resistance to flow through the side inlet due to a more tortuous pathway for the fluid, and thus a higher pressure drop, whereas an insulator aperture extending past the plate will offer lower resistance to flow through the side inlet.

Further, while the opposing surfaces of plate 1312 and insulator 1310 are generally parallel to one another, these surfaces may be any shape desired. For instance, the distal surface of insulator leading to the opening of insulator aperture 1340 can be chamfered to further reduce fluid flow resistance. Flow features can be provided at the insulator aperture and/or plate surface to induce specific fluid flow dynamics to the fluid being removed from the surgical site. For example, ribs, grooves, or baffles can be provided on the insulator aperture and/or plate surface to induce a swirl flow pattern to improve fluid flow suction of the RF probe, to prevent build-up of tissue material which could cause clogs, or the like.

Figure 41:
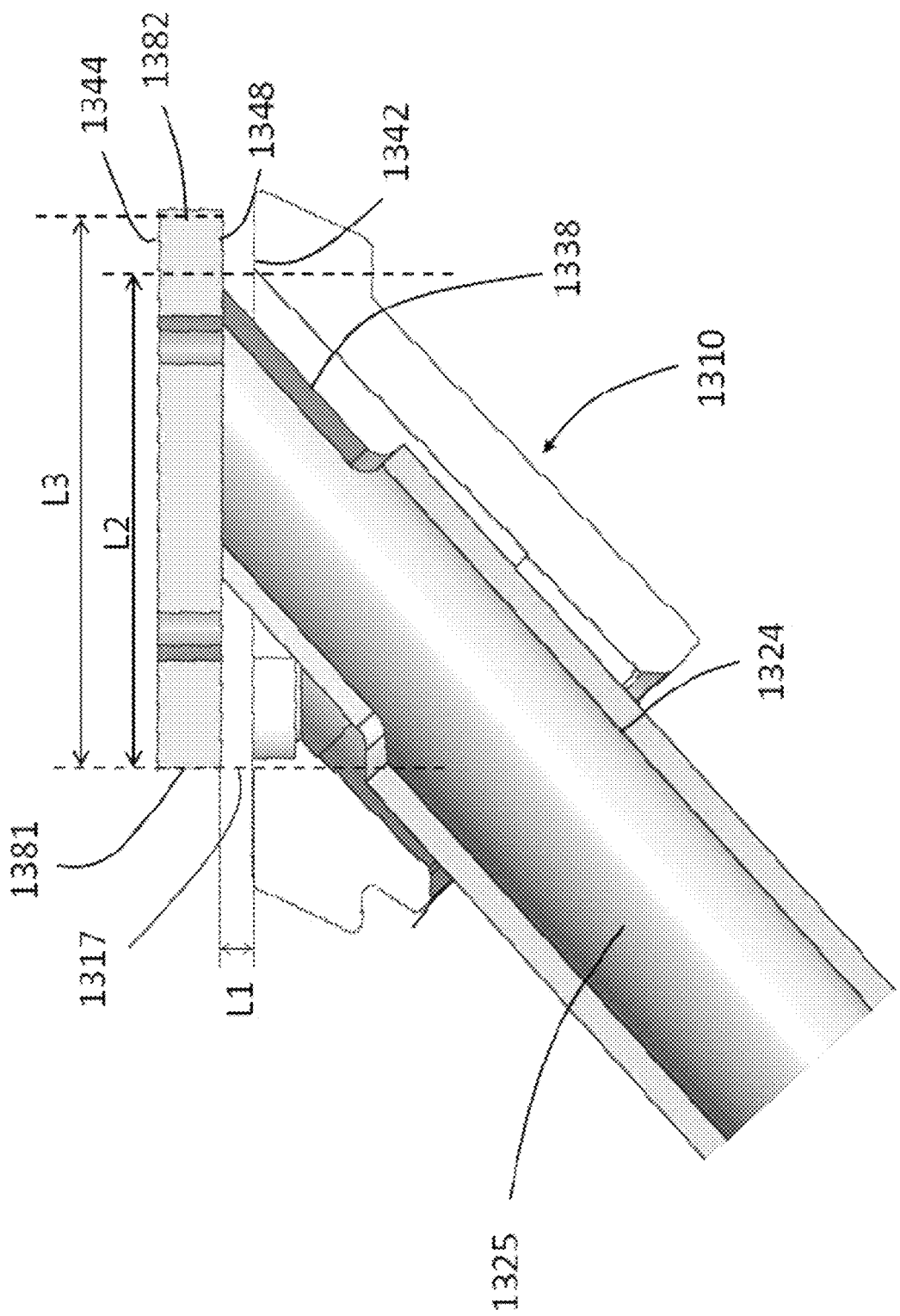
FIG. 41 is a side cross-sectional view of the RF probe of FIG. 38 along line C-C including inner body prongs according to another embodiment.

The interface between inner body 1324 and plate 1312 can be varied adjacent to side inlet 1317 in other embodiments. For example, prongs 1338 of inner body 1324 extend proximally to minimize flow obstruction of fluid being drawn through side inlet 1317 as best shown in FIG. 41. Side slots 1327 formed between prongs 1338 provide additional fluid pathways to remove fluid from the surgical site through side inlets 1317.

Figure 42:
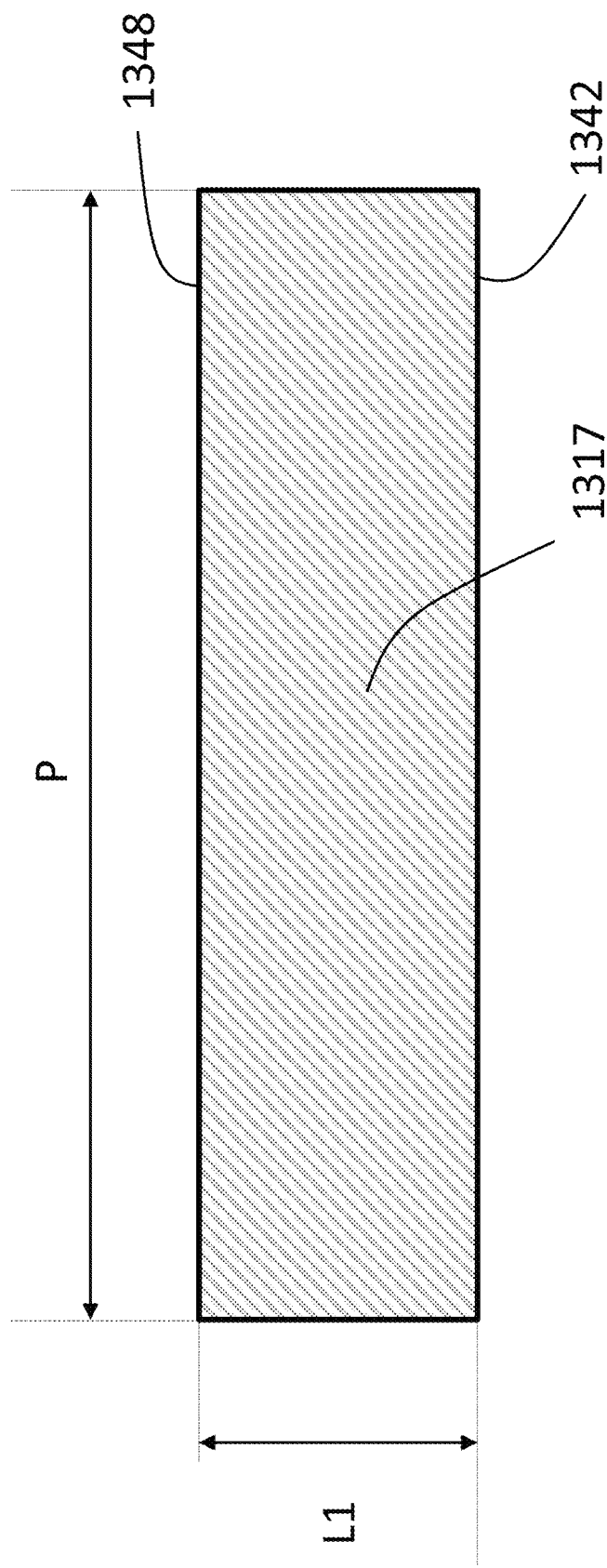
FIG. 42 is a schematic projection of a side inlet of the RF probe of FIG. 40.

Referring now to FIG. 42, there is shown a schematic projection of side inlet 1317 depicting a projected inlet area 1319 on a plane transverse to distal/proximal surface of plate 1312. As is evident from FIG. 42, projected inlet area 1319 can be increased or decreased by adjusting gap dimension L1 (i.e., the amount of separation between the plate and insulator) and/or a perimeter P of the plate 1312 or aperture 1340 to control suction flow rate for RF probe 1300.

Figure 43:
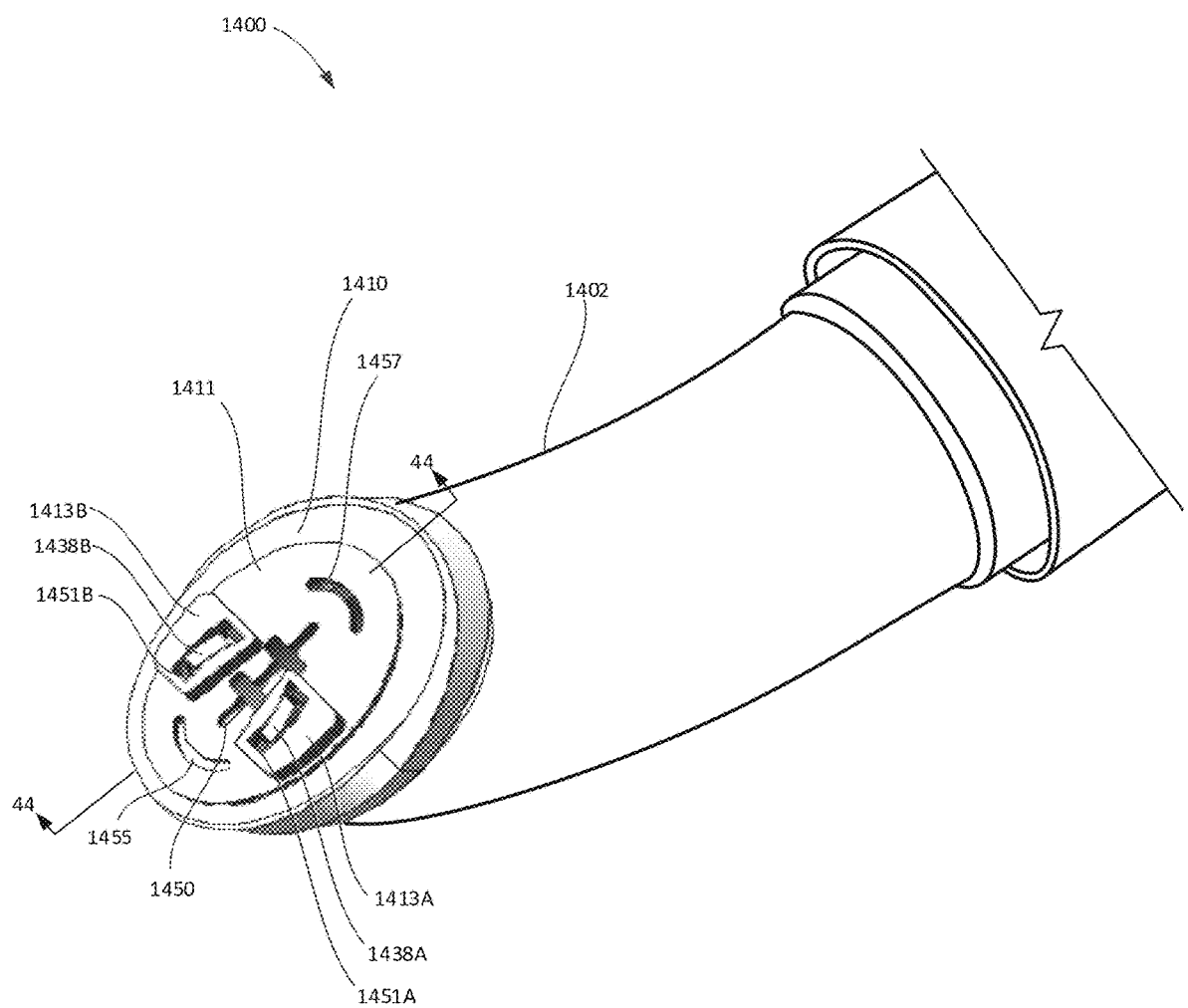
FIG. 43 is a perspective view of an RF probe according to another embodiment of the present disclosure.
Figure 44:
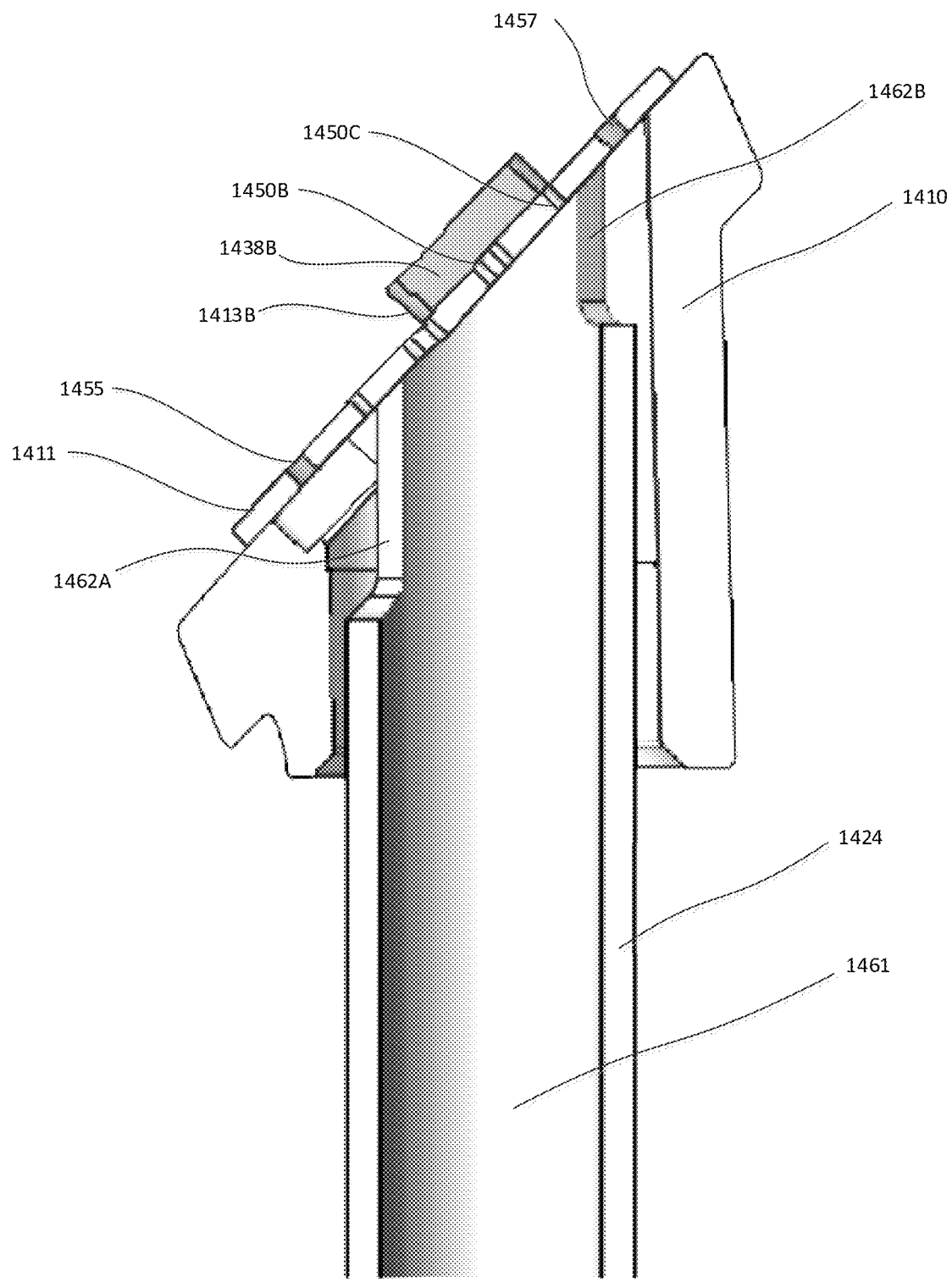
FIG. 44 is a side cross-sectional view of the RF probe of FIG. 43.
Figure 45:
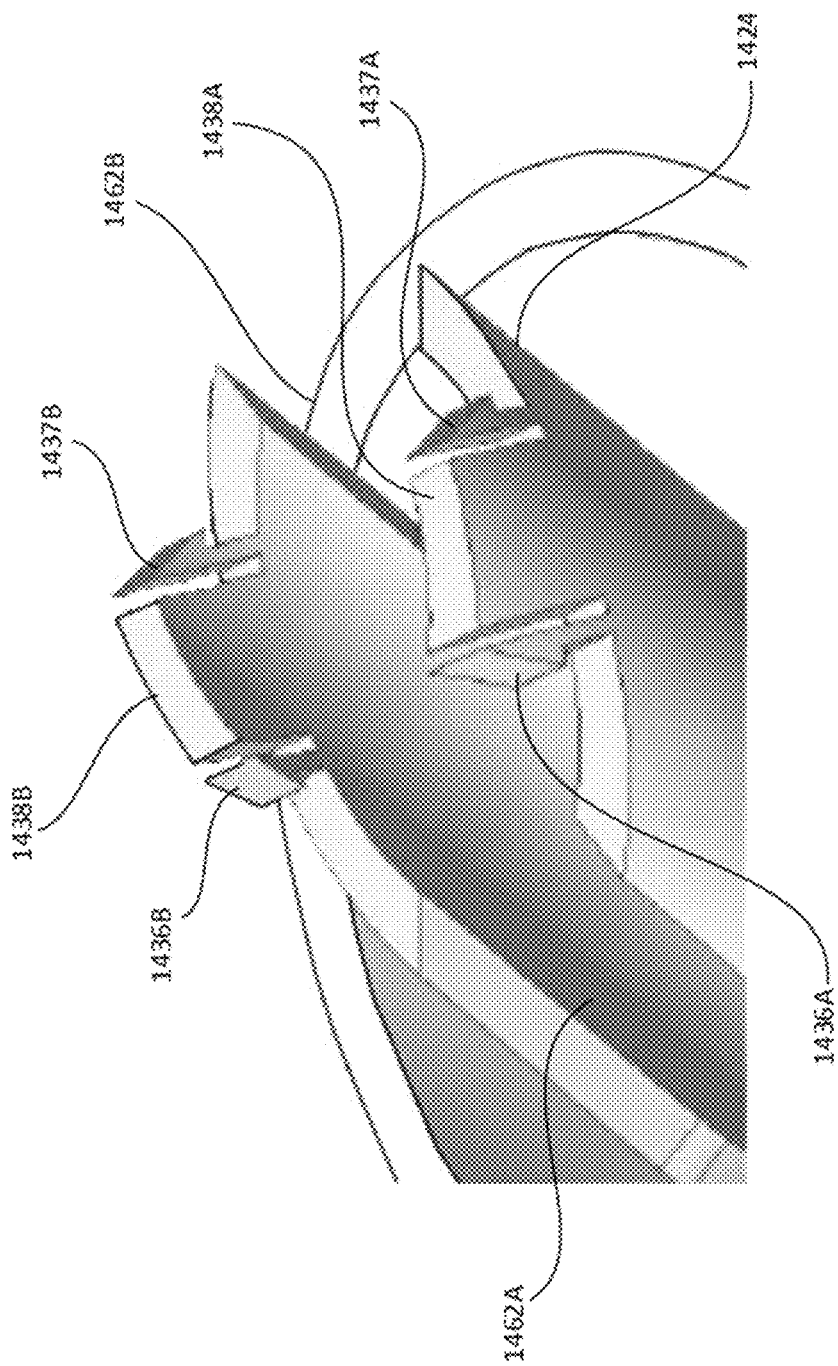
FIG. 45 is a close up partial perspective view of the RF probe of FIG. 43.
Figure 46A:
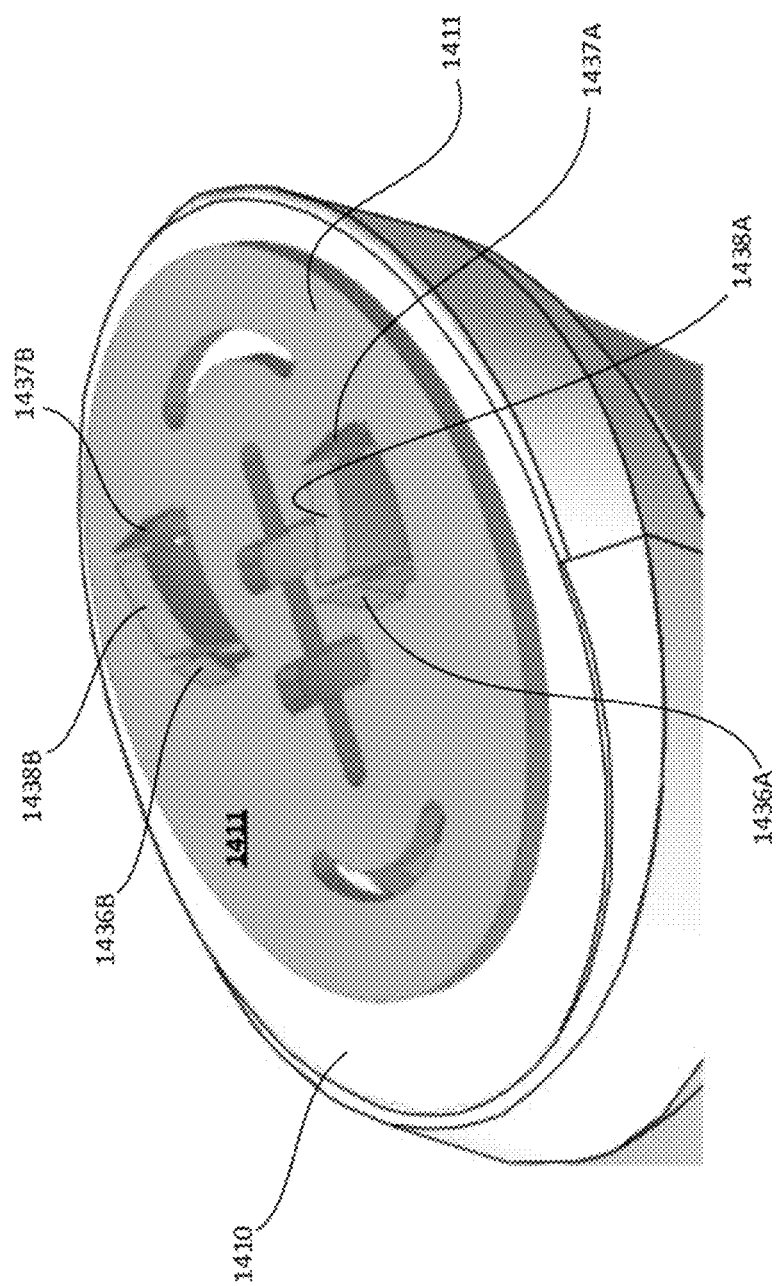

Yet another embodiment of the RF probe of the present disclosure is shown in FIGS. 43-47. RF probe 1400 is similar to RF probe 1100, and therefore like elements are referred to with similar numerals but within the 1400-series of numbers. Elongate inner body 1424 includes a lumen 1461, i.e., cannulation, and a distal end with cut outs 1462A-B in the structure, as shown in FIG. 44. As depicted, each cut out is opposite the other and is located so that apertures 1455, 1457, described in greater detail below, are in communication with lumen 1461. Extending from a distal end of inner body 1424 are two projections 1438A-B. Also extending from the distal end of inner body 1424 are flexible arrow shaped projections 1436A-B, 1437A-B, best shown in FIGS. 45 and 46A, each of which extend from the inner body parallel to and immediately adjacent to projections 1438A-B so that there are two arrow shaped projections for each projection 1438A-B. In alternative arrangements, such projections may have a shape other than an arrow, or the inner body may exclude such projections altogether, arrow shaped or otherwise. FIG. 46A illustrates projections 1438A-B and arrow heads of arrow shaped projections 1436A, 1437A, 1436B, 1437B extending past the proximal surface of plate 1411 prior to welding. Once welding is performed, projections 1438A-B and arrow heads of arrow shaped projections 1436A, 1437A, 1436B, 1437B are melted on the distal surface of plate 1411 such that these projection are generally flush with the plate surface of a fully assembled RF probe 1400. Surrounding inner body 1424 is insulator 1410, which is positioned adjacent to and connected with outer body 1402. Insulator 1410 is hollow and forms an enclosure around an outer surface of inner body 1424, as best shown in FIG. 44. A proximal end of an interior surface of insulator 1410 seals against inner body 1424 so that the hollow cavity of the insulator is closed at its proximal end. This seal may be in the form of a rubber gasket (not shown) or other similar airtight structure. In this manner, any fluids passing into the cavity of insulator from its distal end will be directed into lumen 1461 and will not leak into a space between the inner and outer bodies. FIG. 46B illustrates plate 1411 in see-through such that the distal end of inner body 1424 can be viewed. As illustrated in this embodiment, cutouts 1462A-B of elongate inner body 1424 may communicate with apertures 1455, 1457, respectively, to provide a flow path through the plate and into the central lumen 1461. As best shown in FIGS. 44 and 46B, second aperture 1455 and third aperture 1457 allow fluid from the surgical site to flow through plate 1411 via these apertures and through cutouts 1462A and 1462B, respectively. First aperture 1450 allows fluid to pass through the plate and directly into lumen 1461. Thus, RF probe 1400 allows for two different fluid paths through the plate: a first fluid path passing through the plate (via first aperture 1450) and directly into lumen 1461, and a second fluid path passing through the plate (via second aperture 1455 and third aperture 1457) and entering the lumen through the cutouts. In another embodiment, rather than having multiple apertures, plate 1411 can have a single aperture extending over the lumen and the cutouts to allow for these two fluid paths via this single aperture.

Distal end surfaces of both inner body 1424 and insulator 1410 are flush with a proximally facing side of a first plate 1411, as best shown in FIG. 44. Positioned directly on a distal surface of first plate 1411 are second plate 1413A and third plate 1413B, as best shown in FIG. 43. Slots 1451A-B are located through first plate 1411 and one of second plate 1413A and third plate 1413B, respectively. Slots 1451A-B facilitate securing the first, second and third plate with inner body by welding, heat staking or any other method as more fully explained below. Each projection 1438A-B extends through a respective slot 1451A-B. As shown, free ends of each projection 1438A-B are generally flush with a top surface of a respective plate 1413A-B, however, it should be appreciated that free ends of one or both projections 1438A-B may stand proud of a top surface of the second and/or third plates or may even be located below the top surface. Additionally, each of the projections 1438A-B is fixed, e.g., welded, brazed or soldered, to one of the second plate 1413A and the third plate 1413B, thereby electrically connecting the inner body with the outer body (e.g., as the return electrode) via the plates and an additional conductor, e.g., saline or the like, used during operation of the device. In this arrangement, the first plate may be held in place through its position in between the insulator and the second and third plates fixed to the projections above the first plate. Additionally, the insulator may also be held in place through its position in between the outer shaft and the first plate. In some examples, the first plate is not fixed to either projection.

In another embodiment, thermal staking can be used to secure the first plate to the inner body by melting each of the projections 1438A-B, where second and third plates are not present. In such an arrangement, the melted projections will fill and extend past slots 1451A-B over the first plate. Upon solidification, the melted portion will have larger surface area than the slot to prevent pullout of the first plate from the inner body.

Figure 47:
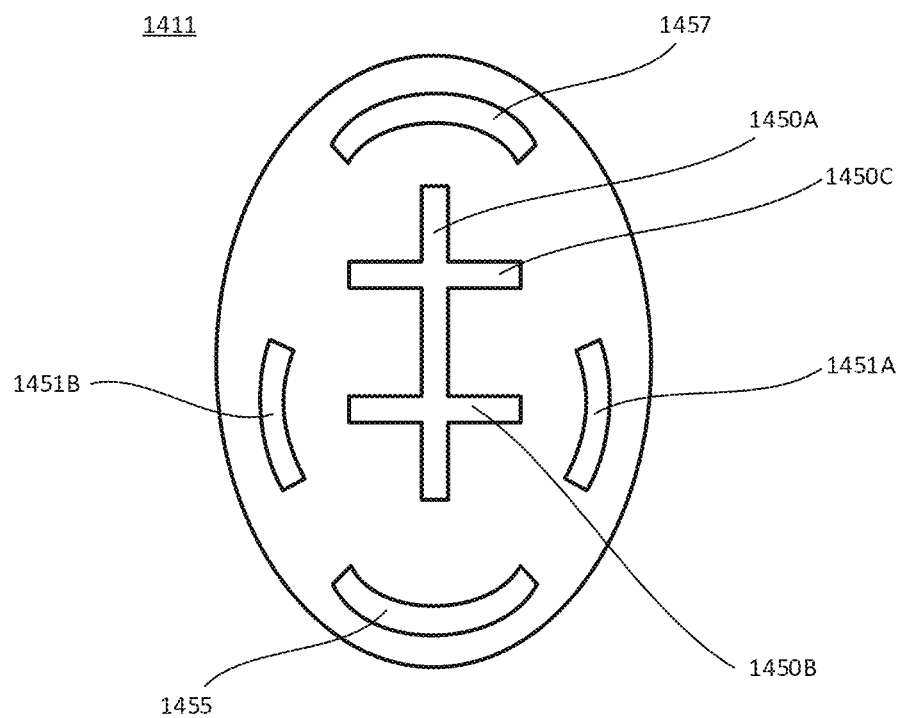
FIG. 47 is a close up top view of a plate in the RF probe of FIG. 43.

Continuing with this illustrated embodiment, first plate 1411 is ovular in shape and includes a plurality of passages in the form of apertures to provide an inlet for fluids collected via suction during an ablation procedure. Although shown in FIGS. 43-44 as apertures, the passages may also be slits extending inward from a perimeter of the plate. In addition to slots 1451A-B, first plate includes first aperture 1450, second aperture 1455 and third aperture 1457. As shown in FIGS. 43 and 47, first aperture 1450 is a single opening and includes three segments 1450A-C, the first 1450A being the longest and the second and third 1450B, 1450C crossing the first in an approximately perpendicular manner Each segment 1450A-C is entirely linear, though in some examples, the exact alignment and size of each segment may vary over its length, and the exact number of such segments may differ. First aperture 1450 is positioned partially in between second and third plates 1413A-B. As shown, first aperture 1450 does not directly abut either the second or the third plate, although it may do so in some examples. Second and third apertures 1455, 1457 are symmetrical and mirror opposites of one another about a central axis oriented laterally across the RF probe end face. Each of second and third apertures 1455, 1457 is a single arcuate shaped segment that resembles a partial circle. As shown, the segments of the various apertures in the first plate each have a generally uniform width along their respective lengths. Relative to lumen 1461 below first plate 1411, first aperture 1450 is in direct communication with lumen 1461, while second and third apertures 1455, 1457 are in direct communication with the cavity of insulator 1410, but are also, through the cavity, in communication with lumen 1461. Although first plate 1411 has a particular arrangement of passages therethrough, it should be appreciated that such arrangement is not limiting.

Both second plate 1413A and third plate 1413B are positioned over and directly abut a distal facing surface of first plate 1411. Second plate 1413A is spaced apart from the third plate 1413B on the surface of first plate 1411. In some examples, the second plate and the third plate are spaced apart such that an internal edge of the first plate that defines the first aperture is spaced apart from both the second plate and the third plate. In some alternative variations, the second plate and the third plate may be a monolithic structure. In the depicted arrangement, each of the second plate and the third plate have four sides and are generally symmetrical with respect to one another about a central longitudinal axis through the first plate. Each of the second plate and the third plate have a proximal surface with a perimeter that abuts the first plate in its entirety. A distally facing surface area of each of the second plate and the third plate is less than 50% of a distally facing surface area of the first plate. In some examples, the distally facing surface area of the second plate may be an amount from 5-25% of the distally facing surface area of the first plate. In other examples, the distally facing surface area of the second plate may be an amount from 5-15% of the distally facing surface area of the first plate. The same variations possible for the second plate are also possible for the third plate. Further to the above examples, it should be appreciated that the size of a second plate or third plate above the first plate may be determined with a view to avoiding reduced electrode functionality by ensuring that the size of the plate is not too large. Similarly, the size may also be determined with a view to avoiding a shortened operational lifespan of the device that may result if the size of the plate is too small. Other considerations for determining a size of the second and third plates include the minimization of clogging while suction occurs. Again, extremely small or large plate sizes relative to the first plate are generally avoided for this reason.

The arrangement of the three plates over the insulator is advantageous in that the raised second and third plates help to prevent tissue from fully engaging the surface of the first plate during use of the device in an ablation procedure. This, in turn, helps to prevent the apertures in the first plate from being blocked, or at minimum, limits the blockage of the apertures. Accordingly, blockage of suction flow during operation of the RF probe is minimized, or at the least, reduced, through the design of RF probe 1400.

Continuing with this illustrated embodiment, first plate 1411 is a tungsten material while second plate 1413A and third plate 1413B are stainless steel. As discussed above, this choice of materials is advantageous in that the use of tungsten improves erosion resistance. Thus, the benefit of reduced erosion of the electrode due to operation of the RF probe over a long duration of time is realized while simplicity and ease of fabrication are preserved. Further, the use of stainless steel for the second and third plates is also advantageous as it renders it easier to fix plates 1413A, 1413B to projections 1438A-B of the stainless steel inner body 1424, e.g., by welding, brazing or soldering.

In yet another embodiment, the RF probe of FIGS. 43-44 may be varied in the following respect. Unless otherwise noted, the features of the RF probe may be the same as those described for RF probe 1400. Here, the first plate is positioned over the elongate inner body and includes a passage through its depth so that at least one projection from the elongate inner body passes through the passage. The first plate is positioned so that it lies flush against the insulator. Adjacent to a portion of the at least one projection that stands proud of the first plate is a second plate. The second plate may be a metal, such as steel, and may have any shape. In this arrangement, the second plate is solid without any apertures, slits or other passages therethrough. To fix the second plate to the projection, a weld or other fixation technique is used. Any suitable outer surface of the second plate may be welded to the portion of the projection that stands proud of the first plate. In some examples, the first plate may include two passages, one for each of two projections extending from a cannulated body of the elongate inner body. In such examples, the RF probe may include second and third plates, both solid without passages therethrough, each welded to a side of a respective projection proud of the first plate. In further examples, a second plate may be welded to a projection on a side of the second plate while a third plate may include a weld slot to receive a projection, with the third plate welded to the projection within the weld slot.

In yet another embodiment, the RF probe may include one or more projections that extend to an outer perimeter edge of a first plate so that the projection does not pass through the first plate. In this arrangement, the projection is welded to an outer surface of the first plate. The first plate includes at least one passage, such as a slit or aperture, for suction intake. As with other embodiments, the insulator surrounds the inner body. Through this assembly, no additional plates are required. In some examples, the inner body including projection and the first plate are tantalum material. In some alternatives, the inner body may have two projections, each extending to opposite outer edges of the first plate. In further alternatives, one projection may extend to a location adjacent to an outer surface of the first plate while a second projection may extend through the first plate to be welded to a second plate above the first plate.

The RF probe 1400 may be varied in many other ways. In some examples, the elongate inner body may have a single projection extending from the cannulated portion. In other examples, the inner body may have one or more projections but no arrow shaped projections to complement the primary projections. In still further examples, the inner body may have two projections with one side of the inner body having an arrow shaped projection on each side of the primary projection, and the second projection on an opposite side of the body not being adjacent to any arrow shaped projections. In other examples, the elongate inner body may have a single cut out at its distal end or no cut outs at all in place of opposing cut outs.

Figure 48:
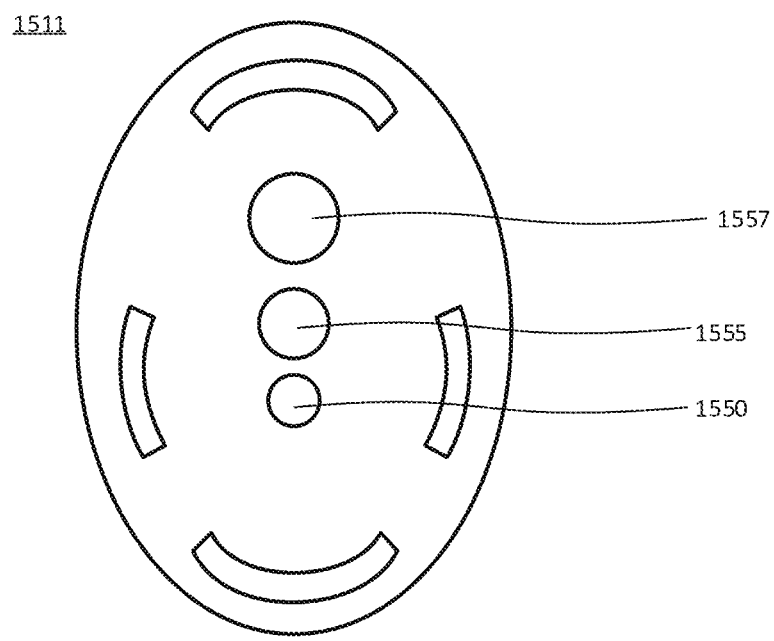
FIG. 48 is a close up top view of a plate of an RF probe according to one embodiment of the present disclosure.

In some examples, the first plate may include a plurality of apertures 1550, 1555, 1557 that are a series of circles having increasing size in one direction, as shown in FIG. 48. In other examples, the apertures through the first plate may be greater or lesser in number and/or have other shapes, while the remaining features of RF probe 1400 are preserved. In some examples, one or both of the second and third plate may include apertures in addition to the weld slots shown. In other examples, a shape of one or both of the second and third plate may vary from that shown and may occupy a greater or lesser share of the first plate distal surface area. In some examples, the second plate may have a different shape than the third plate.

In other examples, the first plate may be thicker or thinner relative to the second and third plates than shown in FIG. 43 for RF probe 1400. In still further examples, the second plate may be thinner or thicker than the third plate. In some examples, the inner body may include three or more projections. In these instances, three or more upper plates may be positioned over the lower, i.e., first plate, each upper plate having a weld slot for a corresponding projection, though one or more of the upper plates may accommodate more than one of the projections from the inner body. The layout of the upper plates over the lower plate may be symmetrical and/or it may involve positioning the upper plates along the periphery of the lower plate.

In some examples, the materials of the first plate and second and/or third plates may be chosen based on their properties relative to one another. For instance, if the second plate is steel, then the first plate may be a material with a melting temperature and corrosion resistance higher than steel. Steel in this example may be substituted with another material to establish other material combinations based on the above described relationship. In other examples, the first plate may be steel, e.g., stainless steel, so that all plates of the RF probe are steel. In these examples, one or more of the first, second and third plates may be welded to a projection of the inner body. In other examples, the elongate inner body and the first plate may be tantalum. In some variations of these examples, the inner body may be welded directly to the first plate so that no additional plates are required. In other examples, materials as described for any embodiment of the present disclosure, such as one or more of steel, tungsten and tantalum, may be used for one or more of the plates included as part of the device. In some examples, fixation techniques other than welding may be used in place of welding to fix the projections of the inner body to plates, such as brazing or soldering. In some examples, the plate or plates of a device may include any type of passage for suction intake into the inner body, such as but not limited to slits, slots and channels.

Figure 49:
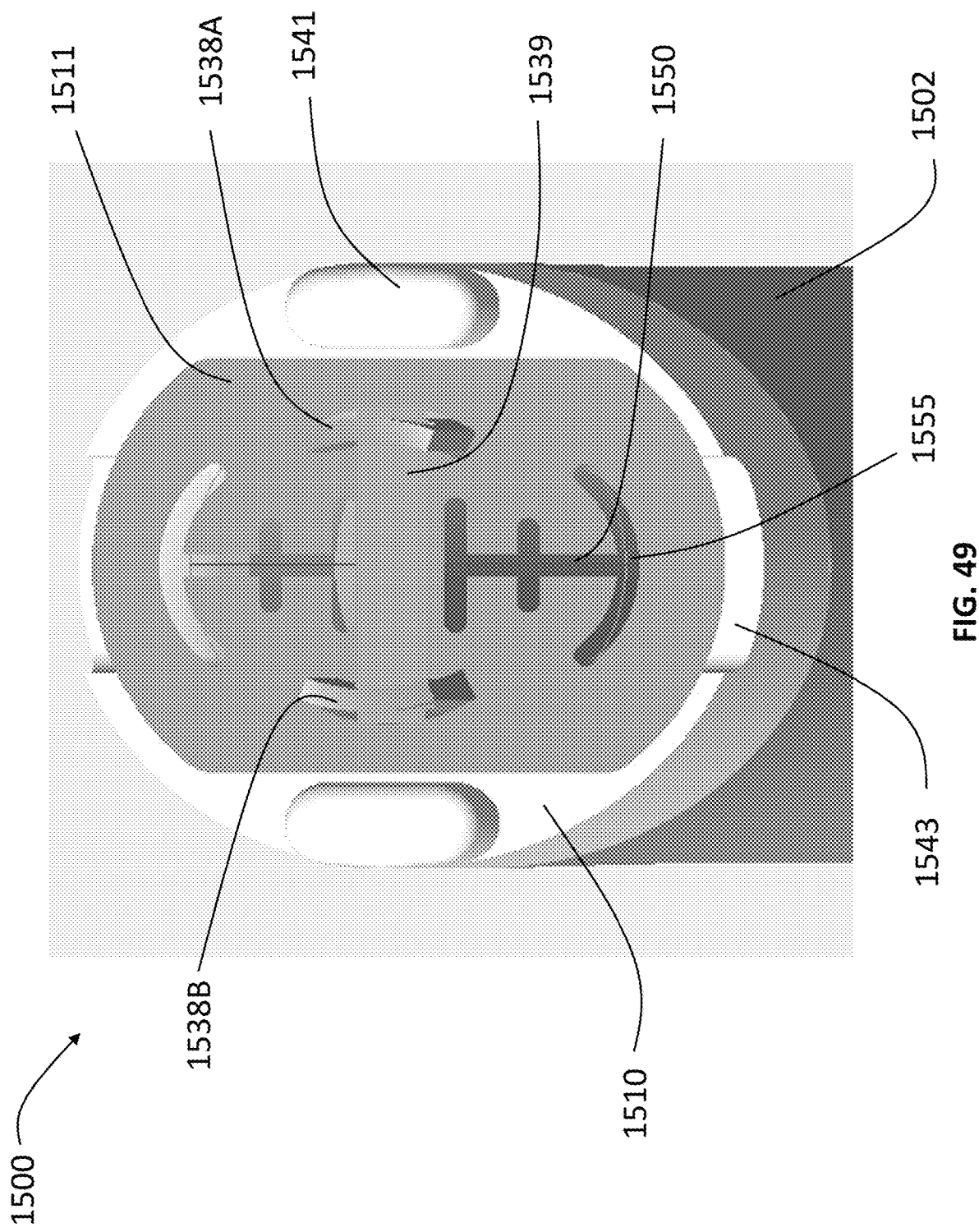
FIG. 49 is a top perspective view of an RF probe according to another embodiment of the present disclosure.

Referring to FIG. 49, there is shown an RF probe 1500 according to another embodiment of the present disclosure. RF probe 1500 is similar to RF probe 1400, and therefore like elements are referred to with similar numerals but within the 1500-series of numbers. For example, RF probe 1500 includes an outer body 1502, an insulator 1510 and a first plate 1511. However, RF probe 1500 also includes a second plate 1539, in this embodiment, shaped as bar 1539 extending between projections 1538A and 1538B. Bar 1539 bolsters the attachment of plate 1511 to the inner body of RF probe 1500 by, for example, being welded to at least one of the projections 1538A, 1538B. While a bar 1539 is illustrated, such a structure may be any other shape desired. RF probe 1500 includes raised bumps 1541 to maintain adequate separation between the surgical site—i.e., tissue and plate 1511 to prevent or minimize clogging during operation. Additional fluid pathways 1555 are also provided to enhance fluid flow from the surgical site to the inner body. Additionally, in this embodiment, while the projections are shown as passing through passages in the plate, any embodiment may include projections extending lateral to the plate, such that the bar extends from at least one of the projections and overtop of the plate.

A method for ablating tissue with an RF probe is described according to another embodiment of the present disclosure. An RF probe having an electrode plate embedded within an insulator as shown in RF probe 600 is utilized for this method. As shown in FIG. 19, raised offsets 674 project distally past plate 612 and thereby prevent direct contact of plate 612 during RF probe use. RF probe 600 is positioned at a surgical site and ablative energy is delivered to the target tissue without contacting plate 612 with the target tissue. Raised offsets 674 prevent direct contact with the target tissue ensuring that only the insulator is in contact with the target tissue to prevent any unintended tissue damage. While RF probe 600 is described in this embodiment, other RF probes having electrodes embedded or placed away from the tissue contacting surfaces of the RF probe can be used in accordance with other embodiments of this method.

A method for ablating tissue with an RF probe to ensure a constant suction flow rate through the RF probe during the ablation procedure is described according to another embodiment of the present disclosure. A method in accordance with this embodiment utilizes an RF probe with a fluid inlet area configured to remain constant during the ablation process to ensure constant fluid flow rate through the RF probe. For example, RF probe 400 shown in FIG. 13 can be utilized for this method. As described above, erosion of plate 412 from the outer periphery of plate 412 towards the center during the ablation process does not change inlet area of inlet 417. Therefore, for a given suction force acting within fluid flow path 425, the suction flow rate remains constant during the ablation process because the area of inlet 417 remains constant. While RF probe 400 is described in this embodiment, other RF probes having electrodes configured to erode in a manner that does that not change the inlet area can be used in accordance with other embodiments of this method.

In another embodiment, a method of ablating tissue involves use of RF probe 1400 shown in FIGS. 43-44. During one exemplary procedure, the RF probe is placed in position at a target site and saline is supplied to the site. When electricity is supplied to the RF probe, it flows through inner body 1424 to projections 1438A-B, first plate 1411 and second and third plates 1413A, 1413B, collectively, the input electrode. Via saline supplied to the target site as noted above, electrical current is carried from the input electrode over the insulator to outer body 1402, the return electrode, to close the circuit. To ablate tissue, a user directs RF probe 1400 so that raised second and third plates 1413A-B are adjacent to or contact the target tissue. The probe may be held in this position for a duration of time sufficient to ablate the tissue without blocking apertures 1450, 1455, 1457 drawing tissue and other fluids into lumen 1461, since the apertures are recessed relative to the raised plates. Materials suctioned through apertures 1455, 1457 travel through a space between insulator and inner body before reaching lumen 1461, the insulator acting as a funnel to direct intake into the lumen, while intake through aperture 1450 is received directly in lumen 1461. Further, the apertures are of sufficient size to handle expected volumes of fluid as part of the suction process. The use of tungsten for plate 1411 minimizes erosion thereby allowing RF probe 1400 to be used for longer durations and for a greater total number of procedures than device configurations that incorporate other electrode materials.

In another embodiment, the present disclosure relates to assembly of the plates for RF probe 1400. In particular, with inner body 1424 disposed within outer body 1402 and insulator 1410 disposed over inner body 1424, first plate 1411 is snapped onto inner body 1424 by pushing slots 1451A-B of first plate 1411 through projections 1436A-1438A, 1436B-1438B, the arrow heads of arrow shaped projections 1436A, 1437A, 1436B, 1437B bending inward during advancement of the first plate and then snapping outward once a top surface of first plate 1411 passes the widest point on the arrowhead projections. The structure of inner body 1424 including arrow shaped projections is advantageous in that it allows first plate to be held with respect to projections 1438A-B until fixation of the plates to the inner body is completed, e.g., via welding.

While various RF probes having varying features are described above, it should be understood that any of these features can be combined in other embodiments in accordance with the present disclosure.

Furthermore, various electrode coatings can be applied to RF probes described herein to facilitate the manufacturing process of the RF probes. The use of coatings over the electrode allows for selection of base materials which are easier to work with as the coatings reduce the electrode erosion. Further, this allows for more traditional methods of bonding the plate with the inner body using processes such as welding or threading. Typically, electrodes are thickened by adding mass to extend the life of the RF probe. However, this reduces efficiency of the electrode as the additional mass must also be heated during the ablation process. Instead, applying coatings such as diamond-like carbon ("DLC") or tungsten to a stainless steel electrode can increase the life of the electrode and make the electrode more workable. Further, the electrode design can be optimized by controlling the layer of the coating to facilitate more rapid joule heating of the electrode surface for more rapid vapor layer generation during the ablation procedure. Likewise, using such coatings can provide for a smaller size second (and third) plate as the coatings can provide increased wear resistance of the second (and third) plate.

It should be noted that any of the devices and methods disclosed herein can be used in conjunction with robotic technology. For example, any of the RF probes described herein can be used with robotic surgical systems to perform an ablation procedure. The RF probes can be manipulated with a robotic system or a robotic arm to rotate, position, and supply ablative energy during a procedure. Further, any or all of the steps described in the methods for performing an ablative procedure of the present disclosure may be performed using a robotic system.

The electrosurgical devices for use in arthroscopic procedures described herein in various embodiments may be used in combination with tissue imaging procedures. An example of a tissue imaging procedure is fluorescence imaging, white light imaging, or a combination thereof. Fluorescence imaging technologies typically employ the use of a fluorescence imaging agent or a dye such as, for example, indocyanine green ("ICG") dye. ICG, when administered to the subject (e.g., intravenously) circulates with the blood in the tissue.

In some variations, the fluorescence imaging agent (e.g., ICG) may be administered to the subject (e.g., into a vein, an artery, or other tissue) as a bolus injection, in a suitable concentration for imaging and for use in arthroscopic procedures. In some variations where the method is performed to assess tissue perfusion and/or vascularization of the tissue, the fluorescence imaging agent may be administered to the subject by injection into a vein or artery of the subject such that the dye bolus circulates in the vasculature and traverses the microvasculature. In some variations in which multiple fluorescence imaging agents are used, such agents may be administered simultaneously (e.g., in a single bolus), or sequentially (e.g., in separate boluses). In some variations, the fluorescence imaging agent may be administered by a catheter. In some variations, the fluorescence imaging agent may be administered to the subject less than an hour in advance of performing the arthroscopic procedure in combination with imaging. For example, the fluorescence imaging agent may be administered to the subject less than 30 minutes in advance of the procedure. In other variations, the fluorescence imaging agent may be administered at least 30 seconds in advance of performing the procedure. In some variations, the fluorescence imaging agent may be administered contemporaneously with performing the procedure.

In some variations, the fluorescence imaging agent may be administered in various concentrations to achieve a desired circulating concentration in the blood. For example, in some variations for tissue perfusion assessment and/or vascularization of the tissue where the fluorescence imaging agent is ICG, the fluorescence imaging agent may be administered at a concentration of about 2.5 mg/mL to achieve a circulating concentration of about 5 µM to about 10 µM in blood. In some variations, the upper concentration limit for the administration of the fluorescence imaging agent is the concentration at which the fluorescence imaging agent becomes clinically toxic in circulating blood, and the lower concentration limit is the limit for instruments used to acquire fluorescence images of the tissue that detect the fluorescence imaging agent circulating in blood. In some variations, the upper concentration limit for the administration of the fluorescence imaging agent is the concentration at which the fluorescence imaging agent becomes self-quenching. For example, the circulating concentration of ICG may range from about 2 µM to about 10 mM.

Thus, in a variation, the electrosurgical device according to various embodiments for use in arthroscopic procedures may be used in combination with or during an imaging procedure such as fluorescence imaging which may comprise administration of a fluorescence imaging agent or other imaging agent to the subject, and generation or acquisition of fluorescence images of the tissue over time. In another variation, the use of the electrosurgical device in combination with an imaging procedure according to various embodiments may exclude any step of administering the fluorescence imaging agent or other imaging agent to the subject. For instance, fluorescence images (video) of the tissue may be based on measurements of a fluorescence imaging agent such as, for example, indocyanine green (ICG) dye that is already present in the subject and/or based on autofluorescence response (e.g., native tissue autofluorescence or induced tissue autofluorescence), or measurements of a combination of autofluorescence and exogenous fluorescence arising from a fluorescence imaging agent. Where possible, in some embodiments, the imaging agent, such as a fluorescence imaging agent, may be delivered to the tissue enterally, intraperitoneally, transdermally or via inhalation.

In some variations, a suitable fluorescence imaging agent comprises an agent which can circulate with the blood and which fluoresces when exposed to appropriate excitation light energy. The fluorescence imaging agent may comprise a fluorescence dye, an analogue thereof, a derivative thereof, or a combination of these. A fluorescence dye may include any non-toxic fluorescence dye. In some variations, the fluorescence imaging agent optimally emits fluorescence in the near-infrared spectrum. In some variations, the fluorescence imaging agent is or comprises a tricarbocyanine dye such as, for example, indocyanine green (ICG). In other variations, the fluorescence imaging agent is or comprises fluorescein isothiocyanate, rhodamine, phycoerythrin, phycocyanin, allophycocyanin, o-phthaldehyde, fluorescamine, rose Bengal, trypan blue, fluoro-gold, green fluorescence protein, flavins (e.g., riboflavin, etc.), methylene blue, porphysomes, cyanine dyes (e.g., cathepsin-activated Cy5 combined with a targeting ligand, Cy5.5, etc.), IRDye800CW, CLR 1502 combined with a targeting ligand, OTL38 combined with a targeting ligand, methylene blue or a combination thereof, which is excitable using excitation light wavelengths appropriate to each imaging agent. In some variations, the fluorescence imaging agent is or comprises methylene blue, ICG, or a combination thereof. In some variations, an analogue or a derivative of the fluorescence imaging agent may be used. For example, a fluorescence dye analogue or a derivative may include a fluorescence dye that has been chemically modified, but still retains its ability to fluoresce when exposed to light energy of an appropriate wavelength. In variations in which some or all of the fluorescence is derived from autofluorescence, one or more of the fluorophores giving rise to the autofluorescence may be an endogenous tissue fluorophore (e.g., collagen, elastin, NADH, etc.), 5-aminolevulinic acid (5-ALA), or a combination thereof.

In some variations, the fluorescence imaging agent may be provided as a lyophilized powder, solid, or liquid. The fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. Any diluent or carrier which will maintain the fluorescence imaging agent in solution may be used. As an example, ICG may be reconstituted with water. In some variations, once the fluorescence imaging agent is reconstituted, it may be mixed with additional diluents and carriers. In some variations, the fluorescence imaging agent may be conjugated to another molecule, (e.g., a protein, a peptide, an amino acid, a synthetic polymer, or a sugar) so as to enhance solubility, stability, imaging properties or a combination thereof. Additional buffering agents may optionally be added including Tris, HCl, NaOH, phosphate buffer, HEPES.

In some variations, upon intravascular administration, fluorescence imaging agent, e.g., ICG, may be used for fluorescence imaging of blood flow and tissue perfusion before, during, and after invasive and minimally invasive surgical procedures. The fluorescence imaging agent, e.g., ICG, may be used, for example, with the electrosurgical devices describe herein in combination with a fluorescence imaging system such as, for example, the SPY® Elite, LUNA, SPY-PHI and PINPOINT® fluorescence imaging systems (available from Stryker Corp.) to perform preoperative tissue assessment/imaging, intraoperative fluorescence imaging, and post-operative assessment/imaging.

One or more embodiments are directed to a fluorescence imaging agent for use in the arthroscopic and imaging devices, systems and methods as described herein. In one or more embodiments, the use in combination with an orthopaedic procedure (e.g., an arthroscopic procedure) may comprise blood flow imaging, tissue perfusion imaging, vascularization assessment, or a combination thereof, which may occur during an invasive surgical procedure, a minimally invasive surgical procedure, a non-invasive surgical procedure, or a combination thereof. The fluorescence agent may be included in a kit comprising the electrosurgical device described herein.

Although the invention disclosed herein has been described with reference to particular features, it is to be understood that these features are merely illustrative of the principles and applications of the present disclosure. It is therefore to be understood that numerous modifications, including changes in the sizes of the various features described herein, may be made to the illustrative embodiments and that other arrangements may be devised without departing from the spirit and scope of the present disclosure. In this regard, the present disclosure encompasses numerous additional features in addition to those specific features set forth in the paragraphs below. Moreover, the foregoing disclosure should be taken by way of illustration rather than by way of limitation.

For the purpose of clarity and a concise description, features are described herein as part of the same or separate embodiments; however, it will be appreciated that the scope of the disclosure includes embodiments having combinations of all or some of the features described.

The invention claimed is:

1. An electrosurgical device for use in arthroscopic procedures comprising:
   an elongate outer body;
   an elongate inner body having a cannulated portion extending from a proximal end to a distal end, the elongate inner body including first and second projections extending distally from the distal end of the cannulated portion, the elongate inner body disposed partially within the elongate outer body;
   a first plate having a plurality of passages including first and second passages therethrough, the first plate being positioned such that the first projection extends through the first passage and the second projection extends through the second passage of the first plate;
   a second plate disposed on the first plate, the second plate including a third passage extending therethrough to receive and fix the first projection to the second plate;
   a third plate disposed on the first plate, the third plate including a fourth passage extending therethrough to receive and fix the second projection to the third plate; and
   an insulator disposed around the elongate inner body, the insulator abutting the elongate outer body at a first end and abutting the first plate at a second end opposite the first end, wherein when electricity is supplied to the elongate inner body and a conductor is present at a distal end of the electrosurgical device, a closed circuit is formed and the first, second and third plates collectively form a first electrode and the elongate outer body is a second electrode of the electrosurgical device.

2. The electrosurgical device of claim 1, wherein the plurality of passages of the first plate include a first aperture, a second aperture and a third aperture between the first and second apertures.

3. The electrosurgical device of claim 2, wherein the plurality of passages of the first plate further includes at least a fourth aperture, wherein at least a portion of the third aperture extends beyond an inner diameter of the elongated inner body and at least a portion of the fourth aperture is within the inner diameter of the elongated inner body.

4. The electrosurgical device of claim 1, wherein the first plate is a first material and the second and third plates are a second material with a melting temperature and corrosion resistance lower than that of the first material.

5. The electrosurgical device of claim 4, wherein the first material is tungsten and the second material is stainless steel.

6. The electrosurgical device of claim 1, wherein the first plate, the second plate and the third plate are steel.

7. The electrosurgical device of claim 1, wherein first and second projections are welded, brazed or soldered to the second plate and the third plate respectively, and the first plate is held in place by its position in between the second plate and the insulator.

8. The electrosurgical device of claim 1, wherein the second plate includes a weld slot to receive the second projection therein.

9. The electrosurgical device of claim 1, wherein each of the second plate and the third plate have a first distally facing surface area and the first plate has a second distally facing surface area, the first distally facing surface area being less than 25% of the second distally facing surface area.

10. The electrosurgical device of claim 1, wherein the second plate and the third plate are physically separated by a space therebetween.

11. An electrosurgical device for use in arthroscopic procedures comprising:
    an elongate outer body;
    an elongate inner body having a cannulated portion extending from a proximal end to a distal end and a projection extending distally from the distal end of the cannulated portion, the elongate inner body disposed partially within the elongate outer body;
    a first plate having a first passage and a second passage therethrough, the first plate being positioned such that the projection extends through the first passage of the first plate;
    a second plate disposed on the first plate, the second plate including a third passage extending therethrough to receive and fix the projection to the second plate; and
    an insulator disposed around the elongate inner body, the insulator positioned such that the insulator and the elongate inner body are on a single side of the first plate,
    wherein the first plate is a material with a higher melting temperature and a higher corrosion resistance than steel and the second plate is steel, and
    wherein when electricity is supplied to the elongate inner body and a conductor is present at a distal end of the electrosurgical device, a closed circuit is formed and the first and second plates collectively form a first electrode and the elongate outer body is a second electrode of the electrosurgical device.

12. The electrosurgical device of claim 11, wherein the material of the first plate is tungsten.

* * * * *